(12) United States Patent
Cheline et al.

(10) Patent No.: US 11,864,870 B2
(45) Date of Patent: Jan. 9, 2024

(54) SYSTEM AND METHOD FOR INSTANT AND AUTOMATIC BORDER DETECTION

(71) Applicant: PHILIPS IMAGE GUIDED THERAPY CORPORATION, San Diego, CA (US)

(72) Inventors: A J Cheline, Sacramento, CA (US); Fergus Merritt, El Dorado Hills, CA (US); Asher Cohen, Sacramento, CA (US); Elizabeth Begin, Bellerica, MA (US); Nathaniel J. Kemp, Concord, MA (US); Jason Sproul, Watertown, MA (US); Badr Elmaanaoui, Billerica, MA (US)

(73) Assignee: PHILIPS IMAGE GUIDED THERAPY CORPORATION, San Diego, CA (US)

( * ) Notice: Subject to any disclaimer, the term of this patent is extended or adjusted under 35 U.S.C. 154(b) by 142 days.

(21) Appl. No.: 17/668,693

(22) Filed: Feb. 10, 2022

(65) Prior Publication Data
US 2022/0233081 A1    Jul. 28, 2022

Related U.S. Application Data

(63) Continuation of application No. 14/047,119, filed on Oct. 7, 2013, now Pat. No. 11,272,845.
(Continued)

(51) Int. Cl.
*A61B 5/02*     (2006.01)
*A61B 8/12*     (2006.01)
(Continued)

(52) U.S. Cl.
CPC ........ *A61B 5/02007* (2013.01); *A61B 5/0066* (2013.01); *A61B 5/0086* (2013.01);
(Continued)

(58) Field of Classification Search
None
See application file for complete search history.

(56) References Cited

U.S. PATENT DOCUMENTS 3,301,258 A    1/1967    Werner
3,617,880 A    11/1971   Cormack et al.
(Continued)

FOREIGN PATENT DOCUMENTS

EP    1041373 A2    10/2000
EP    01172637 A1    1/2002
(Continued)

OTHER PUBLICATIONS

International Search Report and Written Opinion dated Nov. 2, 2012, for International Patent Application No. PCT/US12/53168, filed Aug. 30, 2013 (8 pages).
(Continued)

*Primary Examiner* — Colin T. Sakamoto

(57) ABSTRACT

The invention generally relates to medical imaging systems that instantly and/or automatically detect borders. Embodiments of the invention provide an imaging system that automatically detects a border at a location within a vessel in response only to navigational input moving the image to that location. In some embodiments, systems and methods of the invention operate such that when a doctor moves an imaging catheter to a new location with in tissue, the system essentially instantly finds, and optionally displays, the border(s), calculates an occlusion, or both.

10 Claims, 52 Drawing Sheets

Related U.S. Application Data

(60) Provisional application No. 61/739,920, filed on Dec. 20, 2012, provisional application No. 61/710,401, filed on Oct. 5, 2012.

(51) Int. Cl.

| | | |
|---|---|---|
| *A61B 5/00* | (2006.01) | |
| *A61B 8/08* | (2006.01) | |
| *A61B 6/00* | (2006.01) | |
| *G06T 7/13* | (2017.01) | |
| *A61B 8/00* | (2006.01) | |
| *A61B 6/03* | (2006.01) | |

(52) U.S. Cl.
CPC .......... *A61B 5/6852* (2013.01); *A61B 6/5217* (2013.01); *A61B 8/12* (2013.01); *A61B 8/5223* (2013.01); *G06T 7/13* (2017.01); *A61B 6/03* (2013.01); *A61B 6/469* (2013.01); *A61B 6/487* (2013.01); *A61B 6/504* (2013.01); *A61B 8/0858* (2013.01); *A61B 8/0891* (2013.01); *A61B 8/469* (2013.01); *A61B 8/483* (2013.01); *A61B 2576/02* (2013.01); *G06T 2207/10136* (2013.01); *G06T 2207/30101* (2013.01)

(56) References Cited

U.S. PATENT DOCUMENTS

| | | |
|---|---|---|
| 3,789,841 A | 2/1974 | Antoshkiw |
| 3,841,308 A | 10/1974 | Tate |
| 4,140,364 A | 2/1979 | Yamashita et al. |
| 4,274,423 A | 6/1981 | Mizuno et al. |
| 4,344,438 A | 8/1982 | Schultz |
| 4,398,791 A | 8/1983 | Dorsey |
| 4,432,370 A | 2/1984 | Hughes et al. |
| 4,552,554 A | 11/1985 | Gould et al. |
| 4,577,543 A | 3/1986 | Wilson |
| 4,676,980 A | 6/1987 | Segal et al. |
| 4,682,895 A | 7/1987 | Costello |
| 4,733,665 A | 3/1988 | Palmaz |
| 4,744,619 A | 5/1988 | Cameron |
| 4,762,129 A | 8/1988 | Bonzel |
| 4,766,386 A | 8/1988 | Oliver et al. |
| 4,771,774 A | 9/1988 | Simpson et al. |
| 4,794,931 A | 1/1989 | Yock |
| 4,800,886 A | 1/1989 | Nestor |
| 4,803,639 A | 2/1989 | Steele et al. |
| 4,816,567 A | 3/1989 | Cabilly et al. |
| 4,819,740 A | 4/1989 | Warrington |
| 4,821,731 A | 4/1989 | Martinelli et al. |
| 4,824,435 A | 4/1989 | Giesy et al. |
| 4,830,023 A | 5/1989 | de Toledo et al. |
| 4,834,093 A | 5/1989 | Littleford et al. |
| 4,841,977 A | 6/1989 | Griffith et al. |
| 4,864,578 A | 9/1989 | Proffitt et al. |
| 4,873,690 A | 10/1989 | Adams |
| 4,877,314 A | 10/1989 | Kanamori |
| 4,887,606 A | 12/1989 | Yock et al. |
| 4,917,085 A | 4/1990 | Smith |
| 4,917,097 A | 4/1990 | Proudian et al. |
| 4,928,693 A | 5/1990 | Goodin et al. |
| 4,932,413 A | 6/1990 | Shockey et al. |
| 4,932,419 A | 6/1990 | de Toledo |
| 4,948,229 A | 8/1990 | Soref |
| 4,951,677 A | 8/1990 | Crowley et al. |
| 4,969,742 A | 11/1990 | Falk et al. |
| 4,987,412 A | 1/1991 | Vaitekunas et al. |
| 4,993,412 A | 2/1991 | Murphy-Chutorian |
| 4,998,972 A | 3/1991 | Chin et al. |
| 5,000,185 A | 3/1991 | Yock |
| 5,024,234 A | 6/1991 | Leary et al. |
| 5,025,445 A | 6/1991 | Anderson et al. |
| 5,032,123 A | 7/1991 | Katz et al. |
| 5,037,169 A | 8/1991 | Chun |
| 5,039,193 A | 8/1991 | Snow et al. |
| 5,040,548 A | 8/1991 | Yock |
| 5,041,108 A | 8/1991 | Fox et al. |
| 5,054,492 A | 10/1991 | Scribner et al. |
| 5,065,010 A | 11/1991 | Knute |
| 5,065,769 A | 11/1991 | de Toledo |
| 5,085,221 A | 2/1992 | Ingebrigtsen et al. |
| 5,095,911 A | 3/1992 | Pomeranz |
| 5,100,424 A | 3/1992 | Jang et al. |
| 5,120,308 A | 6/1992 | Hess |
| 5,125,137 A | 6/1992 | Corl et al. |
| 5,135,486 A | 8/1992 | Eberle et al. |
| 5,135,516 A | 8/1992 | Sahatjian et al. |
| 5,155,439 A | 10/1992 | Holmbo et al. |
| 5,158,548 A | 10/1992 | Lau et al. |
| 5,163,445 A | 11/1992 | Christian et al. |
| 5,167,233 A | 12/1992 | Eberle et al. |
| 5,174,295 A | 12/1992 | Christian et al. |
| 5,176,141 A | 1/1993 | Bom et al. |
| 5,176,674 A | 1/1993 | Hofmann |
| 5,178,159 A | 1/1993 | Christian |
| 5,183,048 A | 2/1993 | Eberle |
| 5,188,632 A | 2/1993 | Goldenberg |
| 5,201,316 A | 4/1993 | Pomeranz et al. |
| 5,202,745 A | 4/1993 | Sorin et al. |
| 5,203,779 A | 4/1993 | Muller et al. |
| 5,220,922 A | 6/1993 | Barany |
| 5,224,953 A | 7/1993 | Morgentaler |
| 5,226,421 A | 7/1993 | Frisbie et al. |
| 5,240,003 A | 8/1993 | Lancee et al. |
| 5,240,437 A | 8/1993 | Christian |
| 5,242,460 A | 9/1993 | Klein et al. |
| 5,243,988 A | 9/1993 | Sieben et al. |
| 5,257,974 A | 11/1993 | Cox |
| 5,266,302 A | 11/1993 | Peyman et al. |
| 5,267,954 A | 12/1993 | Nita |
| 5,301,001 A | 4/1994 | Murphy et al. |
| 5,312,425 A | 5/1994 | Evans et al. |
| 5,313,949 A | 5/1994 | Yock |
| 5,313,957 A | 5/1994 | Little |
| 5,319,492 A | 6/1994 | Dorn et al. |
| 5,321,501 A | 6/1994 | Swanson et al. |
| 5,325,198 A | 6/1994 | Hartley et al. |
| 5,336,178 A | 8/1994 | Kaplan et al. |
| 5,346,689 A | 9/1994 | Peyman et al. |
| 5,348,017 A | 9/1994 | Thornton et al. |
| 5,348,481 A | 9/1994 | Ortiz |
| 5,353,798 A | 10/1994 | Sieben |
| 5,358,409 A | 10/1994 | Obara |
| 5,358,478 A | 10/1994 | Thompson et al. |
| 5,368,037 A | 11/1994 | Eberle et al. |
| 5,373,845 A | 12/1994 | Gardineer et al. |
| 5,373,849 A | 12/1994 | Maroney et al. |
| 5,375,602 A | 12/1994 | Lancee et al. |
| 5,377,682 A | 1/1995 | Ueno et al. |
| 5,383,853 A | 1/1995 | Jung et al. |
| 5,387,193 A | 2/1995 | Miraki |
| 5,396,328 A | 3/1995 | Jestel et al. |
| 5,397,355 A | 3/1995 | Marin et al. |
| 5,405,377 A | 4/1995 | Cragg |
| 5,411,016 A | 5/1995 | Kume et al. |
| 5,419,777 A | 5/1995 | Hofling |
| 5,421,338 A | 6/1995 | Crowley et al. |
| 5,423,806 A | 6/1995 | Dale et al. |
| 5,427,118 A | 6/1995 | Nita et al. |
| 5,431,673 A | 7/1995 | Summers et al. |
| 5,436,759 A | 7/1995 | Dijaili et al. |
| 5,439,139 A | 8/1995 | Brovelli |
| 5,443,457 A | 8/1995 | Ginn et al. |
| 5,453,575 A | 9/1995 | O'Donnell et al. |
| 5,456,693 A | 10/1995 | Conston et al. |
| 5,459,570 A | 10/1995 | Swanson et al. |
| 5,480,388 A | 1/1996 | Zadini et al. |
| 5,485,845 A | 1/1996 | Verdonk et al. |
| 5,492,125 A | 2/1996 | Kim et al. |
| 5,496,997 A | 3/1996 | Pope |
| 5,507,761 A | 4/1996 | Duer |
| 5,512,044 A | 4/1996 | Duer |
| 5,514,128 A | 5/1996 | Hillsman et al. |
| 5,529,674 A | 6/1996 | Hedgcoth |

(56) References Cited

U.S. PATENT DOCUMENTS

| | | |
|---|---|---|
| 5,541,730 A | 7/1996 | Chaney |
| 5,546,717 A | 8/1996 | Penczak et al. |
| 5,546,948 A | 8/1996 | Hamm et al. |
| 5,565,332 A | 10/1996 | Hoogenboom et al. |
| 5,573,520 A | 11/1996 | Schwartz et al. |
| 5,581,638 A | 12/1996 | Givens et al. |
| 5,586,054 A | 12/1996 | Jensen et al. |
| 5,592,939 A | 1/1997 | Martinelli |
| 5,596,079 A | 1/1997 | Smith et al. |
| 5,598,844 A | 2/1997 | Diaz et al. |
| 5,609,606 A | 3/1997 | O'Boyle |
| 5,630,806 A | 5/1997 | Inagaki et al. |
| 5,651,366 A | 7/1997 | Liang et al. |
| 5,660,180 A | 8/1997 | Malinowski et al. |
| 5,667,499 A | 9/1997 | Welch et al. |
| 5,667,521 A | 9/1997 | Keown |
| 5,672,877 A | 9/1997 | Liebig et al. |
| 5,674,232 A | 10/1997 | Halliburton |
| 5,693,015 A | 12/1997 | Walker et al. |
| 5,713,848 A | 2/1998 | Dubrul et al. |
| 5,745,634 A | 4/1998 | Garrett et al. |
| 5,771,895 A | 6/1998 | Slager |
| 5,779,731 A | 7/1998 | Leavitt |
| 5,780,958 A | 7/1998 | Strugach et al. |
| 5,798,521 A | 8/1998 | Froggatt |
| 5,800,450 A | 9/1998 | Lary et al. |
| 5,803,083 A | 9/1998 | Buck et al. |
| 5,814,061 A | 9/1998 | Osborne et al. |
| 5,817,025 A | 10/1998 | Alekseev et al. |
| 5,820,594 A | 10/1998 | Fontirroche et al. |
| 5,824,520 A | 10/1998 | Mulligan-Kehoe |
| 5,827,313 A | 10/1998 | Ream |
| 5,830,222 A | 11/1998 | Makower |
| 5,848,121 A | 12/1998 | Gupta et al. |
| 5,851,464 A | 12/1998 | Davila et al. |
| 5,857,974 A | 1/1999 | Eberle et al. |
| 5,872,829 A | 2/1999 | Wischmann et al. |
| 5,873,835 A | 2/1999 | Hastings et al. |
| 5,882,722 A | 3/1999 | Kydd |
| 5,912,764 A | 6/1999 | Togino |
| 5,916,194 A | 6/1999 | Jacobsen et al. |
| 5,921,931 A | 7/1999 | O'Donnell et al. |
| 5,925,055 A | 7/1999 | Adrian et al. |
| 5,949,929 A | 9/1999 | Hamm |
| 5,951,586 A | 9/1999 | Berg et al. |
| 5,974,521 A | 10/1999 | Akerib |
| 5,976,120 A | 11/1999 | Chow et al. |
| 5,978,391 A | 11/1999 | Das et al. |
| 5,997,523 A | 12/1999 | Jang |
| 6,021,240 A | 2/2000 | Murphy et al. |
| 6,022,319 A | 2/2000 | Willard et al. |
| 6,031,071 A | 2/2000 | Mandeville et al. |
| 6,036,889 A | 3/2000 | Kydd |
| 6,043,883 A | 3/2000 | Leckel et al. |
| 6,050,949 A | 4/2000 | White et al. |
| 6,059,738 A | 5/2000 | Stoltze et al. |
| 6,068,638 A | 5/2000 | Makower |
| 6,074,362 A | 6/2000 | Jang et al. |
| 6,078,831 A | 6/2000 | Belef et al. |
| 6,080,109 A | 6/2000 | Baker et al. |
| 6,091,496 A | 7/2000 | Hill |
| 6,094,591 A | 7/2000 | Foltz et al. |
| 6,095,976 A | 8/2000 | Nachtomy et al. |
| 6,097,755 A | 8/2000 | Guenther, Jr. et al. |
| 6,099,471 A | 8/2000 | Torp et al. |
| 6,099,549 A | 8/2000 | Bosma et al. |
| 6,102,938 A | 8/2000 | Evans et al. |
| 6,106,476 A | 8/2000 | Corl et al. |
| 6,120,445 A | 9/2000 | Grunwald |
| 6,123,673 A | 9/2000 | Eberle et al. |
| 6,134,003 A | 10/2000 | Tearney et al. |
| 6,139,510 A | 10/2000 | Palermo |
| 6,141,089 A | 10/2000 | Thoma et al. |
| 6,146,328 A | 11/2000 | Chiao et al. |
| 6,148,095 A | 11/2000 | Prause et al. |
| 6,151,433 A | 11/2000 | Dower et al. |
| 6,152,877 A | 11/2000 | Masters |
| 6,152,878 A | 11/2000 | Nachtomy et al. |
| 6,159,225 A | 12/2000 | Makower |
| 6,165,127 A | 12/2000 | Crowley |
| 6,176,842 B1 | 1/2001 | Tachibana et al. |
| 6,179,809 B1 | 1/2001 | Khairkhahan et al. |
| 6,186,949 B1 | 2/2001 | Hatfield et al. |
| 6,190,353 B1 | 2/2001 | Makower et al. |
| 6,200,266 B1 | 3/2001 | Shokrollahi et al. |
| 6,200,268 B1 | 3/2001 | Vince et al. |
| 6,203,537 B1 | 3/2001 | Adrian |
| 6,208,415 B1 | 3/2001 | De Boer et al. |
| 6,210,332 B1 | 4/2001 | Chiao et al. |
| 6,210,339 B1 | 4/2001 | Kiepen et al. |
| 6,212,308 B1 | 4/2001 | Donald |
| 6,231,518 B1 | 5/2001 | Grabek et al. |
| 6,245,066 B1 | 6/2001 | Morgan et al. |
| 6,249,076 B1 | 6/2001 | Madden et al. |
| 6,254,543 B1 | 7/2001 | Grunwald et al. |
| 6,256,090 B1 | 7/2001 | Chen et al. |
| 6,258,052 B1 | 7/2001 | Milo |
| 6,261,246 B1 | 7/2001 | Pantages et al. |
| 6,275,628 B1 | 8/2001 | Jones et al. |
| 6,275,724 B1 | 8/2001 | Dickinson |
| 6,283,921 B1 | 9/2001 | Nix et al. |
| 6,283,951 B1 | 9/2001 | Flaherty et al. |
| 6,295,308 B1 | 9/2001 | Zah |
| 6,299,622 B1 | 10/2001 | Snow et al. |
| 6,312,384 B1 | 11/2001 | Chiao |
| 6,325,797 B1 | 12/2001 | Stewart et al. |
| 6,328,696 B1 | 12/2001 | Fraser |
| 6,343,168 B1 | 1/2002 | Murphy et al. |
| 6,343,178 B1 | 1/2002 | Burns et al. |
| 6,350,240 B1 | 2/2002 | Song et al. |
| 6,364,841 B1 | 4/2002 | White et al. |
| 6,366,722 B1 | 4/2002 | Murphy et al. |
| 6,367,984 B1 | 4/2002 | Stephenson et al. |
| 6,373,970 B1 | 4/2002 | Dong et al. |
| 6,375,615 B1 | 4/2002 | Flaherty et al. |
| 6,375,618 B1 | 4/2002 | Chiao et al. |
| 6,375,628 B1 | 4/2002 | Zadno-Azizi et al. |
| 6,376,830 B1 | 4/2002 | Froggatt et al. |
| 6,379,352 B1 | 4/2002 | Reynolds et al. |
| 6,381,350 B1 | 4/2002 | Klingensmith et al. |
| 6,387,124 B1 | 5/2002 | Buscemi et al. |
| 6,396,976 B1 | 5/2002 | Little et al. |
| 6,398,792 B1 | 6/2002 | O'Connor |
| 6,417,948 B1 | 7/2002 | Chowdhury et al. |
| 6,419,644 B1 | 7/2002 | White et al. |
| 6,421,164 B2 | 7/2002 | Tearney et al. |
| 6,423,012 B1 | 7/2002 | Kato et al. |
| 6,426,796 B1 | 7/2002 | Pulliam et al. |
| 6,428,041 B1 | 8/2002 | Wohllebe et al. |
| 6,428,498 B2 | 8/2002 | Uflacker |
| 6,429,421 B1 | 8/2002 | Meller et al. |
| 6,440,077 B1 | 8/2002 | Jung et al. |
| 6,443,903 B1 | 9/2002 | White et al. |
| 6,450,964 B1 | 9/2002 | Webler |
| 6,457,365 B1 | 10/2002 | Stephens et al. |
| 6,459,844 B1 | 10/2002 | Pan |
| 6,468,290 B1 | 10/2002 | Weldon et al. |
| 6,475,149 B1 | 11/2002 | Sumanaweera |
| 6,480,285 B1 | 11/2002 | Hill |
| 6,491,631 B2 | 12/2002 | Chiao et al. |
| 6,491,636 B2 | 12/2002 | Chenal et al. |
| 6,501,551 B1 | 12/2002 | Tearney et al. |
| 6,504,286 B1 | 1/2003 | Porat et al. |
| 6,508,824 B1 | 1/2003 | Flaherty et al. |
| 6,514,237 B1 | 2/2003 | Maseda |
| 6,520,269 B2 | 2/2003 | Geiger et al. |
| 6,520,677 B2 | 2/2003 | Iizuka |
| 6,535,764 B2 | 3/2003 | Imran et al. |
| 6,538,778 B1 | 3/2003 | Leckel et al. |
| 6,544,217 B1 | 4/2003 | Gulachenski |
| 6,544,230 B1 | 4/2003 | Flaherty et al. |
| 6,545,760 B1 | 4/2003 | Froggatt et al. |
| 6,546,272 B1 | 4/2003 | MacKinnon et al. |
| 6,551,250 B2 | 4/2003 | Khalil |

(56) References Cited

U.S. PATENT DOCUMENTS

| | | |
|---|---|---|
| 6,566,648 B1 | 5/2003 | Froggatt |
| 6,570,894 B2 | 5/2003 | Anderson |
| 6,572,555 B2 | 6/2003 | White et al. |
| 6,579,311 B1 | 6/2003 | Makower |
| 6,584,335 B1 | 6/2003 | Haar et al. |
| 6,592,612 B1 | 7/2003 | Samson et al. |
| 6,594,448 B2 | 7/2003 | Herman et al. |
| 6,602,241 B2 | 8/2003 | Makower et al. |
| 6,611,322 B1 | 8/2003 | Nakayama et al. |
| 6,611,720 B2 | 8/2003 | Hata et al. |
| 6,612,992 B1 | 9/2003 | Hossack et al. |
| 6,615,062 B2 | 9/2003 | Ryan et al. |
| 6,615,072 B1 | 9/2003 | Izatt et al. |
| 6,621,562 B2 | 9/2003 | Durston |
| 6,631,284 B2 | 10/2003 | Nutt et al. |
| 6,638,227 B2 | 10/2003 | Bae |
| 6,645,152 B1 | 11/2003 | Jung et al. |
| 6,646,745 B2 | 11/2003 | Verma et al. |
| 6,655,386 B1 | 12/2003 | Makower et al. |
| 6,659,957 B1 | 12/2003 | Vardi et al. |
| 6,660,024 B1 | 12/2003 | Flaherty et al. |
| 6,663,565 B2 | 12/2003 | Kawagishi et al. |
| 6,665,456 B2 | 12/2003 | Dave et al. |
| 6,669,716 B1 | 12/2003 | Gilson et al. |
| 6,671,055 B1 | 12/2003 | Wavering et al. |
| 6,673,015 B1 | 1/2004 | Glover et al. |
| 6,673,064 B1 | 1/2004 | Rentrop |
| 6,685,648 B2 | 2/2004 | Flaherty et al. |
| 6,689,056 B1 | 2/2004 | Kilcoyne et al. |
| 6,689,144 B2 | 2/2004 | Gerberding |
| 6,696,173 B1 | 2/2004 | Naundorf et al. |
| 6,701,044 B2 | 3/2004 | Arbore et al. |
| 6,701,176 B1 | 3/2004 | Halperin et al. |
| 6,709,444 B1 | 3/2004 | Makower |
| 6,712,836 B1 | 3/2004 | Berg et al. |
| 6,714,703 B2 | 3/2004 | Lee et al. |
| 6,719,717 B1 | 4/2004 | Johnson et al. |
| 6,725,073 B1 | 4/2004 | Motamedi et al. |
| 6,726,677 B1 | 4/2004 | Flaherty et al. |
| 6,730,107 B2 | 5/2004 | Kelley et al. |
| 6,733,474 B2 | 5/2004 | Kusleika |
| 6,738,144 B1 | 5/2004 | Dogariu |
| 6,740,113 B2 | 5/2004 | Vrba |
| 6,746,464 B1 | 6/2004 | Makower |
| 6,780,157 B2 | 8/2004 | Stephens et al. |
| 6,795,188 B2 | 9/2004 | Ruck et al. |
| 6,795,196 B2 | 9/2004 | Funakawa |
| 6,798,522 B2 | 9/2004 | Stolte et al. |
| 6,822,798 B2 | 11/2004 | Wu et al. |
| 6,830,559 B2 | 12/2004 | Schock |
| 6,832,024 B2 | 12/2004 | Gerstenberger et al. |
| 6,842,639 B1 | 1/2005 | Winston et al. |
| 6,847,449 B2 | 1/2005 | Bashkansky et al. |
| 6,855,115 B2 | 2/2005 | Fonseca et al. |
| 6,856,138 B2 | 2/2005 | Bohley |
| 6,856,400 B1 | 2/2005 | Froggatt |
| 6,856,472 B2 | 2/2005 | Herman et al. |
| 6,860,867 B2 | 3/2005 | Seward et al. |
| 6,866,670 B2 | 3/2005 | Rabiner et al. |
| 6,878,113 B2 | 4/2005 | Miwa et al. |
| 6,886,411 B2 | 5/2005 | Kjellman et al. |
| 6,891,984 B2 | 5/2005 | Petersen et al. |
| 6,895,106 B2 | 5/2005 | Wang et al. |
| 6,898,337 B2 | 5/2005 | Averett et al. |
| 6,900,897 B2 | 5/2005 | Froggatt |
| 6,912,051 B2 | 6/2005 | Jensen |
| 6,916,329 B1 | 7/2005 | Zhao |
| 6,922,498 B2 | 7/2005 | Shah |
| 6,937,346 B2 | 8/2005 | Nebendahl et al. |
| 6,937,696 B1 | 8/2005 | Mostafavi |
| 6,943,939 B1 | 9/2005 | DiJaili et al. |
| 6,947,147 B2 | 9/2005 | Motamedi et al. |
| 6,947,787 B2 | 9/2005 | Webler |
| 6,949,094 B2 | 9/2005 | Yaron |
| 6,952,603 B2 | 10/2005 | Gerber et al. |
| 6,954,737 B2 | 10/2005 | Kalantar et al. |
| 6,958,042 B2 | 10/2005 | Honda |
| 6,961,123 B1 | 11/2005 | Wang et al. |
| 6,966,891 B2 | 11/2005 | Ookubo et al. |
| 6,969,293 B2 | 11/2005 | Thai |
| 6,969,395 B2 | 11/2005 | Eskuri |
| 6,985,234 B2 | 1/2006 | Anderson |
| 7,004,963 B2 | 2/2006 | Wang et al. |
| 7,006,231 B2 | 2/2006 | Ostrovsky et al. |
| 7,010,458 B2 | 3/2006 | Wilt |
| 7,024,025 B2 | 4/2006 | Sathyanarayana |
| 7,027,211 B1 | 4/2006 | Ruffa |
| 7,027,743 B1 | 4/2006 | Tucker et al. |
| 7,033,347 B2 | 4/2006 | Appling |
| 7,035,484 B2 | 4/2006 | Silberberg et al. |
| 7,037,269 B2 | 5/2006 | Nix et al. |
| 7,042,573 B2 | 5/2006 | Froggatt |
| 7,044,915 B2 | 5/2006 | White et al. |
| 7,044,964 B2 | 5/2006 | Jang et al. |
| 7,048,711 B2 | 5/2006 | Rosenman et al. |
| 7,049,306 B2 | 5/2006 | Konradi et al. |
| 7,058,239 B2 | 6/2006 | Singh et al. |
| 7,060,033 B2 | 6/2006 | White et al. |
| 7,060,421 B2 | 6/2006 | Naundorf et al. |
| 7,063,679 B2 | 6/2006 | Maguire et al. |
| 7,068,852 B2 | 6/2006 | Braica |
| 7,074,188 B2 | 7/2006 | Nair et al. |
| 7,095,493 B2 | 8/2006 | Harres |
| 7,110,119 B2 | 9/2006 | Maestle |
| 7,113,875 B2 | 9/2006 | Terashima et al. |
| 7,123,777 B2 | 10/2006 | Rondinelli et al. |
| 7,130,054 B2 | 10/2006 | Ostrovsky et al. |
| 7,139,440 B2 | 11/2006 | Rondinelli et al. |
| 7,153,299 B1 | 12/2006 | Tu et al. |
| 7,171,078 B2 | 1/2007 | Sasaki et al. |
| 7,175,597 B2 | 2/2007 | Vince et al. |
| 7,177,491 B2 | 2/2007 | Dave et al. |
| 7,190,464 B2 | 3/2007 | Alphonse |
| 7,215,802 B2 | 5/2007 | Klingensmith et al. |
| 7,218,811 B2 | 5/2007 | Shigenaga et al. |
| 7,236,812 B1 | 6/2007 | Ballerstadt et al. |
| 7,245,125 B2 | 7/2007 | Harer et al. |
| 7,245,789 B2 | 7/2007 | Bates et al. |
| 7,249,357 B2 | 7/2007 | Landman et al. |
| 7,291,146 B2 | 11/2007 | Steinke et al. |
| 7,292,715 B2 | 11/2007 | Furnish |
| 7,292,885 B2 | 11/2007 | Scott et al. |
| 7,294,124 B2 | 11/2007 | Eidenschink |
| 7,300,460 B2 | 11/2007 | Levine et al. |
| 7,335,161 B2 | 2/2008 | Von Arx et al. |
| 7,337,079 B2 | 2/2008 | Park et al. |
| 7,355,716 B2 | 4/2008 | de Boer et al. |
| 7,356,367 B2 | 4/2008 | Liang et al. |
| 7,358,921 B2 | 4/2008 | Snyder et al. |
| 7,359,062 B2 | 4/2008 | Chen et al. |
| 7,359,554 B2 | 4/2008 | Klingensmith et al. |
| 7,363,927 B2 | 4/2008 | Ravikumar |
| 7,366,376 B2 | 4/2008 | Shishkov et al. |
| 7,382,949 B2 | 6/2008 | Bouma et al. |
| 7,387,636 B2 | 6/2008 | Cohn et al. |
| 7,391,520 B2 | 6/2008 | Zhou et al. |
| 7,397,935 B2 | 7/2008 | Kimmel et al. |
| 7,399,095 B2 | 7/2008 | Rondinelli |
| 7,408,648 B2 | 8/2008 | Kleen et al. |
| 7,414,779 B2 | 8/2008 | Huber et al. |
| 7,440,087 B2 | 10/2008 | Froggatt et al. |
| 7,447,388 B2 | 11/2008 | Bates et al. |
| 7,449,821 B2 | 11/2008 | Dausch |
| 7,450,165 B2 | 11/2008 | Ahiska |
| RE40,608 E | 12/2008 | Glover et al. |
| 7,458,967 B2 | 12/2008 | Appling et al. |
| 7,463,362 B2 | 12/2008 | Lasker et al. |
| 7,463,759 B2 | 12/2008 | Klingensmith et al. |
| 7,491,226 B2 | 2/2009 | Palmaz et al. |
| 7,515,276 B2 | 4/2009 | Froggatt et al. |
| 7,527,594 B2 | 5/2009 | Vardi et al. |
| 7,534,251 B2 | 5/2009 | WasDyke |
| 7,535,797 B2 | 5/2009 | Peng et al. |
| 7,547,304 B2 | 6/2009 | Johnson |

(56) References Cited

U.S. PATENT DOCUMENTS

| | | |
|---|---|---|
| 7,564,949 B2 | 7/2009 | Sattler et al. |
| 7,577,471 B2 | 8/2009 | Camus et al. |
| 7,583,857 B2 | 9/2009 | Xu et al. |
| 7,603,165 B2 | 10/2009 | Townsend et al. |
| 7,612,773 B2 | 11/2009 | Magnin et al. |
| 7,633,627 B2 | 12/2009 | Choma et al. |
| 7,645,229 B2 | 1/2010 | Armstrong |
| 7,658,715 B2 | 2/2010 | Park et al. |
| 7,660,452 B2 | 2/2010 | Zwirn et al. |
| 7,660,492 B2 | 2/2010 | Bates et al. |
| 7,666,204 B2 | 2/2010 | Thornton et al. |
| 7,672,790 B2 | 3/2010 | McGraw et al. |
| 7,680,247 B2 | 3/2010 | Atzinger et al. |
| 7,684,991 B2 | 3/2010 | Stohr et al. |
| 7,711,413 B2 | 5/2010 | Feldman et al. |
| 7,720,322 B2 | 5/2010 | Prisco |
| 7,728,986 B2 | 6/2010 | Lasker et al. |
| 7,734,009 B2 | 6/2010 | Brunner et al. |
| 7,736,317 B2 | 6/2010 | Stephens et al. |
| 7,742,795 B2 | 6/2010 | Stone et al. |
| 7,743,189 B2 | 6/2010 | Brown et al. |
| 7,762,954 B2 | 7/2010 | Nix et al. |
| 7,766,896 B2 | 8/2010 | Kornkven Volk et al. |
| 7,773,792 B2 | 8/2010 | Kimmel et al. |
| 7,775,981 B1 | 8/2010 | Guracar et al. |
| 7,777,399 B2 | 8/2010 | Eidenschink et al. |
| 7,781,724 B2 | 8/2010 | Childers et al. |
| 7,783,337 B2 | 8/2010 | Feldman et al. |
| 7,787,127 B2 | 8/2010 | Galle et al. |
| 7,792,342 B2 | 9/2010 | Barbu et al. |
| 7,801,343 B2 | 9/2010 | Unal et al. |
| 7,801,590 B2 | 9/2010 | Feldman et al. |
| 7,813,609 B2 | 10/2010 | Petersen et al. |
| 7,831,081 B2 | 11/2010 | Li |
| 7,846,101 B2 | 12/2010 | Eberle et al. |
| 7,853,104 B2 | 12/2010 | Oota et al. |
| 7,853,316 B2 | 12/2010 | Milner et al. |
| 7,860,555 B2 | 12/2010 | Saadat |
| 7,862,508 B2 | 1/2011 | Davies et al. |
| 7,872,759 B2 | 1/2011 | Tearney et al. |
| 7,880,868 B2 | 2/2011 | Aoki |
| 7,881,763 B2 | 2/2011 | Brauker et al. |
| 7,909,844 B2 | 3/2011 | Alkhatib et al. |
| 7,921,854 B2 | 4/2011 | Hennings et al. |
| 7,927,784 B2 | 4/2011 | Simpson |
| 7,929,148 B2 | 4/2011 | Kemp |
| 7,930,014 B2 | 4/2011 | Huennekens et al. |
| 7,930,104 B2 | 4/2011 | Baker et al. |
| 7,936,462 B2 | 5/2011 | Jiang et al. |
| 7,942,852 B2 | 5/2011 | Mas et al. |
| 7,947,012 B2 | 5/2011 | Spurchise et al. |
| 7,951,186 B2 | 5/2011 | Eidenschink et al. |
| 7,952,719 B2 | 5/2011 | Brennan, III |
| 7,972,353 B2 | 7/2011 | Hendriksen et al. |
| 7,976,492 B2 | 7/2011 | Brauker et al. |
| 7,977,950 B2 | 7/2011 | Maslen |
| 7,978,916 B2 | 7/2011 | Klingensmith et al. |
| 7,981,041 B2 | 7/2011 | McGahan |
| 7,981,151 B2 | 7/2011 | Rowe |
| 7,983,737 B2 | 7/2011 | Feldman et al. |
| 7,993,333 B2 | 8/2011 | Oral et al. |
| 7,995,210 B2 | 8/2011 | Tearney et al. |
| 7,996,060 B2 | 8/2011 | Trofimov et al. |
| 7,999,938 B2 | 8/2011 | Wang |
| 8,021,377 B2 | 9/2011 | Eskuri |
| 8,021,420 B2 | 9/2011 | Dolan |
| 8,036,732 B2 | 10/2011 | Milner |
| 8,040,586 B2 | 10/2011 | Smith et al. |
| 8,047,996 B2 | 11/2011 | Goodnow et al. |
| 8,049,900 B2 | 11/2011 | Kemp et al. |
| 8,050,478 B2 | 11/2011 | Li et al. |
| 8,050,523 B2 | 11/2011 | Younge et al. |
| 8,052,605 B2 | 11/2011 | Muller et al. |
| 8,057,394 B2 | 11/2011 | Dala-Krishna |
| 8,059,923 B2 | 11/2011 | Bates et al. |
| 8,070,800 B2 | 12/2011 | Lock et al. |
| 8,080,800 B2 | 12/2011 | Hoctor et al. |
| 8,088,102 B2 | 1/2012 | Adams et al. |
| 8,100,838 B2 | 1/2012 | Wright et al. |
| 8,104,479 B2 | 1/2012 | Glynn et al. |
| 8,108,030 B2 | 1/2012 | Castella et al. |
| 8,114,102 B2 | 2/2012 | Galdonik et al. |
| 8,116,605 B2 | 2/2012 | Petersen et al. |
| 8,125,648 B2 | 2/2012 | Milner et al. |
| 8,126,239 B2 | 2/2012 | Sun et al. |
| 8,133,199 B2 | 3/2012 | Weber et al. |
| 8,133,269 B2 | 3/2012 | Flechsenhar et al. |
| 8,140,708 B2 | 3/2012 | Zaharia et al. |
| 8,148,877 B2 | 4/2012 | Jiang et al. |
| 8,167,932 B2 | 5/2012 | Bourang et al. |
| 8,172,757 B2 | 5/2012 | Jaffe et al. |
| 8,177,809 B2 | 5/2012 | Mavani et al. |
| 8,187,191 B2 | 5/2012 | Hancock et al. |
| 8,187,267 B2 | 5/2012 | Pappone et al. |
| 8,187,830 B2 | 5/2012 | Hu et al. |
| 8,199,218 B2 | 6/2012 | Lee et al. |
| 8,206,429 B2 | 6/2012 | Gregorich et al. |
| 8,208,995 B2 | 6/2012 | Tearney et al. |
| 8,222,906 B2 | 7/2012 | Wyar et al. |
| 8,233,681 B2 | 7/2012 | Aylward et al. |
| 8,233,718 B2 | 7/2012 | Klingensmith et al. |
| 8,238,624 B2 | 8/2012 | Doi et al. |
| 8,239,938 B2 | 8/2012 | Simeral et al. |
| 8,277,386 B2 | 10/2012 | Ahmed et al. |
| 8,280,470 B2 | 10/2012 | Milner et al. |
| 8,289,284 B2 | 10/2012 | Glynn et al. |
| 8,289,522 B2 | 10/2012 | Tearney et al. |
| 8,298,147 B2 | 10/2012 | Huennekens et al. |
| 8,298,149 B2 | 10/2012 | Hastings et al. |
| 8,301,000 B2 | 10/2012 | Sillard et al. |
| 8,309,428 B2 | 11/2012 | Lemmerhirt et al. |
| 8,317,713 B2 | 11/2012 | Davies et al. |
| 8,323,201 B2 | 12/2012 | Towfiq et al. |
| 8,329,053 B2 | 12/2012 | Martin et al. |
| 8,336,643 B2 | 12/2012 | Harleman |
| 8,349,000 B2 | 1/2013 | Schreck |
| 8,353,945 B2 | 1/2013 | Andreas et al. |
| 8,353,954 B2 | 1/2013 | Cai et al. |
| 8,357,981 B2 | 1/2013 | Martin et al. |
| 8,361,097 B2 | 1/2013 | Patel et al. |
| 8,386,560 B2 | 2/2013 | Ma et al. |
| 8,398,591 B2 | 3/2013 | Mas et al. |
| 8,412,312 B2 | 4/2013 | Judell et al. |
| 8,417,491 B2 | 4/2013 | Trovato et al. |
| 8,449,465 B2 | 5/2013 | Nair et al. |
| 8,454,685 B2 | 6/2013 | Hariton et al. |
| 8,454,686 B2 | 6/2013 | Alkhatib |
| 8,475,522 B2 | 7/2013 | Jimenez et al. |
| 8,478,384 B2 | 7/2013 | Schmitt et al. |
| 8,486,062 B2 | 7/2013 | Belhe et al. |
| 8,486,063 B2 | 7/2013 | Werneth et al. |
| 8,491,567 B2 | 7/2013 | Magnin et al. |
| 8,500,798 B2 | 8/2013 | Rowe et al. |
| 8,550,911 B2 | 10/2013 | Sylla |
| 8,594,757 B2 | 11/2013 | Boppart et al. |
| 8,597,349 B2 | 12/2013 | Alkhatib |
| 8,600,477 B2 | 12/2013 | Beyar et al. |
| 8,600,917 B1 | 12/2013 | Schimert et al. |
| 8,601,056 B2 | 12/2013 | Lauwers et al. |
| 8,620,055 B2 | 12/2013 | Barratt et al. |
| 8,644,910 B2 | 2/2014 | Rousso et al. |
| 2001/0007940 A1 | 7/2001 | Tu et al. |
| 2001/0029337 A1 | 10/2001 | Pantages et al. |
| 2001/0037073 A1 | 11/2001 | White et al. |
| 2001/0046345 A1 | 11/2001 | Snyder et al. |
| 2001/0049548 A1 | 12/2001 | Vardi et al. |
| 2002/0034276 A1 | 3/2002 | Hu et al. |
| 2002/0041723 A1 | 4/2002 | Ronnekleiv et al. |
| 2002/0069676 A1 | 6/2002 | Kopp et al. |
| 2002/0089335 A1 | 7/2002 | Williams |
| 2002/0099289 A1 | 7/2002 | Crowley |
| 2002/0163646 A1 | 11/2002 | Anderson |
| 2002/0186818 A1 | 12/2002 | Arnaud et al. |
| 2002/0196446 A1 | 12/2002 | Roth et al. |

(56) References Cited

U.S. PATENT DOCUMENTS

| | | |
|---|---|---|
| 2002/0197456 A1 | 12/2002 | Pope |
| 2003/0004412 A1 | 1/2003 | Izatt et al. |
| 2003/0016604 A1 | 1/2003 | Hanes |
| 2003/0018273 A1 | 1/2003 | Corl et al. |
| 2003/0023153 A1 | 1/2003 | Izatt et al. |
| 2003/0032886 A1 | 2/2003 | Dgany et al. |
| 2003/0050871 A1 | 3/2003 | Broughton |
| 2003/0065371 A1 | 4/2003 | Satake |
| 2003/0069723 A1 | 4/2003 | Hegde |
| 2003/0077043 A1 | 4/2003 | Hamm et al. |
| 2003/0085635 A1 | 5/2003 | Davidsen |
| 2003/0090753 A1 | 5/2003 | Takeyama et al. |
| 2003/0092995 A1 | 5/2003 | Thompson |
| 2003/0093059 A1 | 5/2003 | Griffin et al. |
| 2003/0103212 A1 | 6/2003 | Westphal et al. |
| 2003/0152259 A1 | 8/2003 | Belykh et al. |
| 2003/0181802 A1 | 9/2003 | Ogawa |
| 2003/0187369 A1 | 10/2003 | Lewis et al. |
| 2003/0194165 A1 | 10/2003 | Silberberg et al. |
| 2003/0195419 A1 | 10/2003 | Harada |
| 2003/0208116 A1 | 11/2003 | Liang et al. |
| 2003/0212491 A1 | 11/2003 | Mitchell et al. |
| 2003/0219202 A1 | 11/2003 | Loeb et al. |
| 2003/0220749 A1 | 11/2003 | Chen et al. |
| 2003/0228039 A1 | 12/2003 | Green |
| 2004/0015065 A1 | 1/2004 | Panescu et al. |
| 2004/0023317 A1 | 2/2004 | Motamedi et al. |
| 2004/0028333 A1 | 2/2004 | Lomas |
| 2004/0037742 A1 | 2/2004 | Jen et al. |
| 2004/0042066 A1 | 3/2004 | Kinoshita et al. |
| 2004/0054287 A1 | 3/2004 | Stephens |
| 2004/0067000 A1 | 4/2004 | Bates et al. |
| 2004/0068161 A1 | 4/2004 | Couvillon |
| 2004/0082844 A1 | 4/2004 | Vardi et al. |
| 2004/0092830 A1 | 5/2004 | Scott et al. |
| 2004/0106853 A1 | 6/2004 | Moriyama |
| 2004/0111552 A1 | 6/2004 | Arimilli et al. |
| 2004/0126048 A1 | 7/2004 | Dave et al. |
| 2004/0143160 A1 | 7/2004 | Couvillon |
| 2004/0146546 A1 | 7/2004 | Gravett et al. |
| 2004/0186369 A1 | 9/2004 | Lam |
| 2004/0186558 A1 | 9/2004 | Pavcnik et al. |
| 2004/0195512 A1 | 10/2004 | Crosetto |
| 2004/0220606 A1 | 11/2004 | Goshgarian |
| 2004/0225220 A1 | 11/2004 | Rich |
| 2004/0239938 A1 | 12/2004 | Izatt |
| 2004/0242990 A1 | 12/2004 | Brister et al. |
| 2004/0248439 A1 | 12/2004 | Gernhardt et al. |
| 2004/0260236 A1 | 12/2004 | Manning et al. |
| 2005/0013778 A1 | 1/2005 | Green et al. |
| 2005/0031176 A1 | 2/2005 | Hertel et al. |
| 2005/0036150 A1 | 2/2005 | Izatt et al. |
| 2005/0078317 A1 | 4/2005 | Law et al. |
| 2005/0101859 A1 | 5/2005 | Maschke |
| 2005/0140582 A1 | 6/2005 | Lee et al. |
| 2005/0140682 A1 | 6/2005 | Sumanaweera et al. |
| 2005/0140981 A1 | 6/2005 | Waelti |
| 2005/0140984 A1 | 6/2005 | Hitzenberger |
| 2005/0147303 A1 | 7/2005 | Zhou et al. |
| 2005/0165439 A1 | 7/2005 | Weber et al. |
| 2005/0171433 A1 | 8/2005 | Boppart et al. |
| 2005/0171438 A1 | 8/2005 | Chen et al. |
| 2005/0182297 A1 | 8/2005 | Gravenstein et al. |
| 2005/0196028 A1 | 9/2005 | Kleen et al. |
| 2005/0197585 A1 | 9/2005 | Brockway et al. |
| 2005/0213103 A1 | 9/2005 | Everett et al. |
| 2005/0215942 A1 | 9/2005 | Abrahamson et al. |
| 2005/0234445 A1 | 10/2005 | Conquergood et al. |
| 2005/0243322 A1 | 11/2005 | Lasker et al. |
| 2005/0249391 A1 | 11/2005 | Kimmel et al. |
| 2005/0251567 A1 | 11/2005 | Ballew et al. |
| 2005/0254059 A1 | 11/2005 | Alphonse |
| 2005/0264823 A1 | 12/2005 | Zhu et al. |
| 2006/0013523 A1 | 1/2006 | Childers et al. |
| 2006/0015126 A1 | 1/2006 | Sher |
| 2006/0029634 A1 | 2/2006 | Berg et al. |
| 2006/0036167 A1 | 2/2006 | Shina |
| 2006/0038115 A1 | 2/2006 | Maas |
| 2006/0039004 A1 | 2/2006 | de Boer et al. |
| 2006/0041180 A1 | 2/2006 | Viswanathan et al. |
| 2006/0045536 A1 | 3/2006 | Arahira |
| 2006/0055936 A1 | 3/2006 | Yun et al. |
| 2006/0058622 A1 | 3/2006 | Tearney et al. |
| 2006/0064009 A1 | 3/2006 | Webler et al. |
| 2006/0067620 A1 | 3/2006 | Shishkov et al. |
| 2006/0072808 A1 | 4/2006 | Grimm et al. |
| 2006/0074442 A1 | 4/2006 | Noriega et al. |
| 2006/0098927 A1 | 5/2006 | Schmidt et al. |
| 2006/0100694 A1 | 5/2006 | Globerman |
| 2006/0106375 A1 | 5/2006 | Werneth et al. |
| 2006/0132790 A1 | 6/2006 | Gutin |
| 2006/0135870 A1 | 6/2006 | Webler |
| 2006/0142703 A1 | 6/2006 | Carter et al. |
| 2006/0142733 A1 | 6/2006 | Forsberg |
| 2006/0173299 A1 | 8/2006 | Romley et al. |
| 2006/0179255 A1 | 8/2006 | Yamazaki |
| 2006/0184048 A1 | 8/2006 | Saadat |
| 2006/0187537 A1 | 8/2006 | Huber et al. |
| 2006/0195269 A1 | 8/2006 | Yeatman et al. |
| 2006/0204119 A1 | 9/2006 | Feng et al. |
| 2006/0229591 A1 | 10/2006 | Lee |
| 2006/0239312 A1 | 10/2006 | Kewitsch et al. |
| 2006/0241342 A1 | 10/2006 | Macaulay et al. |
| 2006/0241465 A1 | 10/2006 | Huennekens et al. |
| 2006/0241503 A1 | 10/2006 | Schmitt et al. |
| 2006/0244973 A1 | 11/2006 | Yun et al. |
| 2006/0258895 A1 | 11/2006 | Maschke |
| 2006/0264743 A1 | 11/2006 | Kleen et al. |
| 2006/0267756 A1 | 11/2006 | Kates |
| 2006/0270976 A1 | 11/2006 | Savage et al. |
| 2006/0276709 A1 | 12/2006 | Khamene et al. |
| 2006/0279742 A1 | 12/2006 | Tearney et al. |
| 2006/0279743 A1 | 12/2006 | Boesser et al. |
| 2006/0285638 A1 | 12/2006 | Boese et al. |
| 2006/0287595 A1 | 12/2006 | Maschke |
| 2006/0293597 A1 | 12/2006 | Johnson et al. |
| 2007/0015969 A1 | 1/2007 | Feldman et al. |
| 2007/0016029 A1 | 1/2007 | Donaldson et al. |
| 2007/0016034 A1 | 1/2007 | Donaldson |
| 2007/0016062 A1 | 1/2007 | Park et al. |
| 2007/0027390 A1 | 2/2007 | Maschke et al. |
| 2007/0036417 A1 | 2/2007 | Argiro et al. |
| 2007/0038061 A1 | 2/2007 | Huennekens et al. |
| 2007/0038121 A1 | 2/2007 | Feldman et al. |
| 2007/0038125 A1 | 2/2007 | Kleen et al. |
| 2007/0043292 A1 | 2/2007 | Camus et al. |
| 2007/0043597 A1 | 2/2007 | Donaldson |
| 2007/0049847 A1 | 3/2007 | Osborne |
| 2007/0060973 A1 | 3/2007 | Ludvig et al. |
| 2007/0065077 A1 | 3/2007 | Childers et al. |
| 2007/0066888 A1 | 3/2007 | Maschke |
| 2007/0066890 A1 | 3/2007 | Maschke |
| 2007/0066983 A1 | 3/2007 | Maschke |
| 2007/0084995 A1 | 4/2007 | Newton et al. |
| 2007/0100226 A1 | 5/2007 | Yankelevitz et al. |
| 2007/0135887 A1 | 6/2007 | Maschke |
| 2007/0142707 A1 | 6/2007 | Wiklof et al. |
| 2007/0156019 A1 | 7/2007 | Larkin et al. |
| 2007/0161893 A1 | 7/2007 | Milner et al. |
| 2007/0161896 A1 | 7/2007 | Adachi et al. |
| 2007/0161963 A1 | 7/2007 | Smalling |
| 2007/0162860 A1 | 7/2007 | Muralidharan et al. |
| 2007/0165141 A1 | 7/2007 | Srinivas et al. |
| 2007/0167710 A1 | 7/2007 | Unal et al. |
| 2007/0167804 A1 | 7/2007 | Park et al. |
| 2007/0191682 A1 | 8/2007 | Rolland et al. |
| 2007/0201736 A1 | 8/2007 | Klingensmith |
| 2007/0206193 A1 | 9/2007 | Pesach |
| 2007/0208276 A1 | 9/2007 | Kornkven Volk et al. |
| 2007/0225220 A1 | 9/2007 | Ming et al. |
| 2007/0225590 A1 | 9/2007 | Ramos |
| 2007/0229801 A1 | 10/2007 | Tearney et al. |
| 2007/0232872 A1 | 10/2007 | Prough et al. |
| 2007/0232874 A1 | 10/2007 | Ince |

(56) References Cited

U.S. PATENT DOCUMENTS

| | | |
|---|---|---|
| 2007/0232890 A1 | 10/2007 | Hirota |
| 2007/0232891 A1 | 10/2007 | Hirota |
| 2007/0232892 A1 | 10/2007 | Hirota |
| 2007/0232893 A1 | 10/2007 | Tanioka |
| 2007/0232933 A1 | 10/2007 | Gille et al. |
| 2007/0238957 A1 | 10/2007 | Yared |
| 2007/0247033 A1 | 10/2007 | Eidenschink et al. |
| 2007/0250000 A1 | 10/2007 | Magnin et al. |
| 2007/0250036 A1 | 10/2007 | Volk et al. |
| 2007/0258094 A1 | 11/2007 | Izatt et al. |
| 2007/0260138 A1 | 11/2007 | Feldman et al. |
| 2007/0278389 A1 | 12/2007 | Ajgaonkar et al. |
| 2007/0287914 A1 | 12/2007 | Cohen |
| 2008/0002183 A1 | 1/2008 | Yatagai et al. |
| 2008/0013093 A1 | 1/2008 | Izatt et al. |
| 2008/0021275 A1 | 1/2008 | Tearney et al. |
| 2008/0027481 A1 | 1/2008 | Gilson et al. |
| 2008/0043024 A1 | 2/2008 | Schiwietz et al. |
| 2008/0045842 A1 | 2/2008 | Furnish |
| 2008/0051660 A1 | 2/2008 | Kakadaris et al. |
| 2008/0063304 A1 | 3/2008 | Russak et al. |
| 2008/0085041 A1 | 4/2008 | Breeuwer |
| 2008/0095465 A1 | 4/2008 | Mullick et al. |
| 2008/0095714 A1 | 4/2008 | Castella et al. |
| 2008/0097194 A1 | 4/2008 | Milner |
| 2008/0101667 A1 | 5/2008 | Begelman et al. |
| 2008/0108867 A1 | 5/2008 | Zhou |
| 2008/0114254 A1 | 5/2008 | Matcovitch et al. |
| 2008/0119739 A1 | 5/2008 | Vardi et al. |
| 2008/0124495 A1 | 5/2008 | Horn et al. |
| 2008/0125772 A1 | 5/2008 | Stone et al. |
| 2008/0139897 A1 | 6/2008 | Ainsworth et al. |
| 2008/0143707 A1 | 6/2008 | Mitchell |
| 2008/0146941 A1 | 6/2008 | Dala-Krishna |
| 2008/0147111 A1 | 6/2008 | Johnson et al. |
| 2008/0154128 A1 | 6/2008 | Milner |
| 2008/0161696 A1 | 7/2008 | Schmitt et al. |
| 2008/0171944 A1 | 7/2008 | Brenneman et al. |
| 2008/0175465 A1 | 7/2008 | Jiang et al. |
| 2008/0177183 A1 | 7/2008 | Courtney et al. |
| 2008/0180683 A1 | 7/2008 | Kemp |
| 2008/0181477 A1 | 7/2008 | Izatt et al. |
| 2008/0187201 A1 | 8/2008 | Liang et al. |
| 2008/0228086 A1 | 9/2008 | Ilegbusi et al. |
| 2008/0247622 A1 | 10/2008 | Aylward et al. |
| 2008/0247716 A1 | 10/2008 | Thomas et al. |
| 2008/0262470 A1 | 10/2008 | Lee et al. |
| 2008/0262489 A1 | 10/2008 | Steinke |
| 2008/0269599 A1 | 10/2008 | Csavoy et al. |
| 2008/0281205 A1 | 11/2008 | Naghavi et al. |
| 2008/0281248 A1 | 11/2008 | Angheloiu et al. |
| 2008/0285043 A1 | 11/2008 | Fercher et al. |
| 2008/0287795 A1 | 11/2008 | Klingensmith et al. |
| 2008/0291463 A1 | 11/2008 | Milner et al. |
| 2008/0292173 A1 | 11/2008 | Hsieh et al. |
| 2008/0294034 A1 | 11/2008 | Krueger et al. |
| 2008/0298655 A1 | 12/2008 | Edwards |
| 2008/0306766 A1 | 12/2008 | Ozeki et al. |
| 2009/0009801 A1 | 1/2009 | Tabuki |
| 2009/0018393 A1 | 1/2009 | Dick et al. |
| 2009/0034813 A1 | 2/2009 | Dikmen et al. |
| 2009/0043191 A1 | 2/2009 | Castella et al. |
| 2009/0046295 A1 | 2/2009 | Kemp et al. |
| 2009/0052614 A1 | 2/2009 | Hempel et al. |
| 2009/0069843 A1 | 3/2009 | Agnew |
| 2009/0079993 A1 | 3/2009 | Yatagai et al. |
| 2009/0088650 A1 | 4/2009 | Corl |
| 2009/0093980 A1 | 4/2009 | Kemp et al. |
| 2009/0122320 A1 | 5/2009 | Petersen et al. |
| 2009/0138544 A1 | 5/2009 | Wegenkittl et al. |
| 2009/0149739 A9 | 6/2009 | Maschke |
| 2009/0156941 A1 | 6/2009 | Moore |
| 2009/0174886 A1 | 7/2009 | Inoue |
| 2009/0174931 A1 | 7/2009 | Huber et al. |
| 2009/0177090 A1 | 7/2009 | Grunwald et al. |
| 2009/0177183 A1 | 7/2009 | Pinkernell et al. |
| 2009/0195514 A1 | 8/2009 | Glynn et al. |
| 2009/0196470 A1 | 8/2009 | Carl et al. |
| 2009/0198125 A1 | 8/2009 | Nakabayashi et al. |
| 2009/0203991 A1 | 8/2009 | Papaioannou et al. |
| 2009/0264768 A1 | 10/2009 | Courtney et al. |
| 2009/0269014 A1 | 10/2009 | Winberg et al. |
| 2009/0270695 A1 | 10/2009 | McEowen |
| 2009/0284322 A1 | 11/2009 | Harrison et al. |
| 2009/0284332 A1 | 11/2009 | Moore et al. |
| 2009/0284749 A1 | 11/2009 | Johnson et al. |
| 2009/0290167 A1 | 11/2009 | Flanders et al. |
| 2009/0292048 A1 | 11/2009 | Li et al. |
| 2009/0299195 A1 | 12/2009 | Muller et al. |
| 2009/0299284 A1 | 12/2009 | Holman et al. |
| 2009/0318951 A1 | 12/2009 | Kashkarov et al. |
| 2009/0326634 A1 | 12/2009 | Vardi |
| 2010/0007669 A1 | 1/2010 | Bethune et al. |
| 2010/0030042 A1 | 2/2010 | Denninghoff et al. |
| 2010/0061611 A1 | 3/2010 | Xu et al. |
| 2010/0063400 A1 | 3/2010 | Hall et al. |
| 2010/0087732 A1 | 4/2010 | Eberle et al. |
| 2010/0094125 A1 | 4/2010 | Younge et al. |
| 2010/0094127 A1 | 4/2010 | Xu |
| 2010/0094135 A1 | 4/2010 | Fang-Yen et al. |
| 2010/0094143 A1 | 4/2010 | Mahapatra et al. |
| 2010/0113919 A1 | 5/2010 | Maschke |
| 2010/0125238 A1 | 5/2010 | Lye et al. |
| 2010/0125268 A1 | 5/2010 | Gustus et al. |
| 2010/0125648 A1 | 5/2010 | Zaharia et al. |
| 2010/0128348 A1 | 5/2010 | Taverner |
| 2010/0152717 A1 | 6/2010 | Keeler |
| 2010/0160788 A1 | 6/2010 | Davies et al. |
| 2010/0161023 A1 | 6/2010 | Cohen et al. |
| 2010/0168714 A1 | 7/2010 | Burke et al. |
| 2010/0179421 A1 | 7/2010 | Tupin |
| 2010/0179426 A1 | 7/2010 | Davies et al. |
| 2010/0220334 A1 | 9/2010 | Condit et al. |
| 2010/0226607 A1 | 9/2010 | Zhang et al. |
| 2010/0234736 A1 | 9/2010 | Corl |
| 2010/0249601 A1 | 9/2010 | Courtney |
| 2010/0256616 A1 | 10/2010 | Katoh et al. |
| 2010/0272432 A1 | 10/2010 | Johnson |
| 2010/0284590 A1 | 11/2010 | Peng et al. |
| 2010/0290693 A1 | 11/2010 | Cohen et al. |
| 2010/0331950 A1 | 12/2010 | Strommer |
| 2011/0010925 A1 | 1/2011 | Nix et al. |
| 2011/0021926 A1 | 1/2011 | Spencer et al. |
| 2011/0025853 A1 | 2/2011 | Richardson |
| 2011/0026797 A1 | 2/2011 | Declerck et al. |
| 2011/0032533 A1 | 2/2011 | Izatt et al. |
| 2011/0034801 A1 | 2/2011 | Baumgart |
| 2011/0044546 A1 | 2/2011 | Pan et al. |
| 2011/0066073 A1 | 3/2011 | Kuiper et al. |
| 2011/0071401 A1 | 3/2011 | Hastings et al. |
| 2011/0072405 A1 | 3/2011 | Chen et al. |
| 2011/0077528 A1 | 3/2011 | Kemp et al. |
| 2011/0080591 A1 | 4/2011 | Johnson et al. |
| 2011/0087104 A1 | 4/2011 | Moore et al. |
| 2011/0137140 A1 | 6/2011 | Tearney et al. |
| 2011/0144502 A1 | 6/2011 | Zhou et al. |
| 2011/0152771 A1 | 6/2011 | Milner et al. |
| 2011/0157597 A1 | 6/2011 | Lu et al. |
| 2011/0160586 A1 | 6/2011 | Li et al. |
| 2011/0178413 A1 | 7/2011 | Schmitt et al. |
| 2011/0190586 A1 | 8/2011 | Kemp |
| 2011/0216378 A1 | 9/2011 | Poon et al. |
| 2011/0220985 A1 | 9/2011 | Son et al. |
| 2011/0238061 A1 | 9/2011 | van der Weide et al. |
| 2011/0238083 A1 | 9/2011 | Moll et al. |
| 2011/0245669 A1 | 10/2011 | Zhang |
| 2011/0249094 A1 | 10/2011 | Wang et al. |
| 2011/0257545 A1 | 10/2011 | Suri |
| 2011/0264125 A1 | 10/2011 | Wilson et al. |
| 2011/0274329 A1 | 11/2011 | Mathew et al. |
| 2011/0282334 A1 | 11/2011 | Groenhoff |
| 2011/0301684 A1 | 12/2011 | Fischell et al. |
| 2011/0306995 A1 | 12/2011 | Moberg |
| 2011/0319752 A1 | 12/2011 | Steinberg |

(56) References Cited

U.S. PATENT DOCUMENTS

| | | |
|---|---|---|
| 2012/0004529 A1 | 1/2012 | Tolkowsky et al. |
| 2012/0004668 A1 | 1/2012 | Wallace et al. |
| 2012/0013914 A1 | 1/2012 | Kemp et al. |
| 2012/0016344 A1 | 1/2012 | Kusakabe |
| 2012/0016395 A1 | 1/2012 | Olson |
| 2012/0022360 A1 | 1/2012 | Kemp |
| 2012/0026503 A1 | 2/2012 | Lewandowski et al. |
| 2012/0029007 A1 | 2/2012 | Graham et al. |
| 2012/0033866 A1 | 2/2012 | Masumoto |
| 2012/0059253 A1 | 3/2012 | Wang et al. |
| 2012/0059368 A1 | 3/2012 | Takaoka et al. |
| 2012/0062843 A1 | 3/2012 | Ferguson et al. |
| 2012/0065481 A1 | 3/2012 | Hunter et al. |
| 2012/0065511 A1 | 3/2012 | Jamello |
| 2012/0071823 A1 | 3/2012 | Chen |
| 2012/0071838 A1 | 3/2012 | Fojtik |
| 2012/0075638 A1 | 3/2012 | Rollins et al. |
| 2012/0083696 A1 | 4/2012 | Kitamura |
| 2012/0095340 A1 | 4/2012 | Smith |
| 2012/0095372 A1 | 4/2012 | Sverdlik et al. |
| 2012/0108943 A1 | 5/2012 | Bates et al. |
| 2012/0113108 A1 | 5/2012 | Dala-Krishna |
| 2012/0116353 A1 | 5/2012 | Arnold et al. |
| 2012/0130243 A1 | 5/2012 | Balocco et al. |
| 2012/0130247 A1 | 5/2012 | Waters et al. |
| 2012/0136259 A1 | 5/2012 | Milner et al. |
| 2012/0136427 A1 | 5/2012 | Palmaz et al. |
| 2012/0137075 A1 | 5/2012 | Vorbach |
| 2012/0155734 A1 | 6/2012 | Barratt et al. |
| 2012/0158101 A1 | 6/2012 | Stone et al. |
| 2012/0162660 A1 | 6/2012 | Kemp |
| 2012/0165661 A1 | 6/2012 | Kemp et al. |
| 2012/0170848 A1 | 7/2012 | Kemp et al. |
| 2012/0172698 A1 | 7/2012 | Teo et al. |
| 2012/0176607 A1 | 7/2012 | Ott |
| 2012/0184853 A1 | 7/2012 | Waters |
| 2012/0184859 A1 | 7/2012 | Shah et al. |
| 2012/0184977 A1 | 7/2012 | Wolf |
| 2012/0215094 A1 | 8/2012 | Rahimian et al. |
| 2012/0220836 A1 | 8/2012 | Alpert et al. |
| 2012/0220851 A1 | 8/2012 | Razansky et al. |
| 2012/0220865 A1 | 8/2012 | Brown et al. |
| 2012/0220874 A1 | 8/2012 | Hancock et al. |
| 2012/0220883 A1 | 8/2012 | Manstrom et al. |
| 2012/0224751 A1 | 9/2012 | Kemp et al. |
| 2012/0226153 A1 | 9/2012 | Brown et al. |
| 2012/0230565 A1 | 9/2012 | Steinberg et al. |
| 2012/0232400 A1 | 9/2012 | Dickinson et al. |
| 2012/0238869 A1 | 9/2012 | Schmitt et al. |
| 2012/0238956 A1 | 9/2012 | Yamada et al. |
| 2012/0244043 A1 | 9/2012 | Leblanc et al. |
| 2012/0250028 A1 | 10/2012 | Schmitt et al. |
| 2012/0253186 A1 | 10/2012 | Simpson et al. |
| 2012/0253192 A1 | 10/2012 | Cressman |
| 2012/0253276 A1 | 10/2012 | Govari et al. |
| 2012/0257210 A1 | 10/2012 | Whitney et al. |
| 2012/0262720 A1 | 10/2012 | Brown et al. |
| 2012/0265077 A1 | 10/2012 | Gille et al. |
| 2012/0265268 A1 | 10/2012 | Blum et al. |
| 2012/0265296 A1 | 10/2012 | McNamara et al. |
| 2012/0271170 A1 | 10/2012 | Emelianov et al. |
| 2012/0271175 A1 | 10/2012 | Moore et al. |
| 2012/0271339 A1 | 10/2012 | O'Beirne et al. |
| 2012/0274338 A1 | 11/2012 | Baks et al. |
| 2012/0276390 A1 | 11/2012 | Ji et al. |
| 2012/0277722 A1 | 11/2012 | Gerber et al. |
| 2012/0279764 A1 | 11/2012 | Jiang et al. |
| 2012/0283758 A1 | 11/2012 | Miller et al. |
| 2012/0289987 A1 | 11/2012 | Wilson et al. |
| 2012/0299439 A1 | 11/2012 | Huang |
| 2012/0310081 A1 | 12/2012 | Adler et al. |
| 2012/0310332 A1 | 12/2012 | Murray et al. |
| 2012/0319535 A1 | 12/2012 | Dausch |
| 2012/0323075 A1 | 12/2012 | Younge et al. |
| 2012/0323127 A1 | 12/2012 | Boyden et al. |
| 2012/0330141 A1 | 12/2012 | Brown et al. |
| 2013/0015975 A1 | 1/2013 | Huennekens et al. |
| 2013/0023762 A1 | 1/2013 | Huennekens et al. |
| 2013/0023763 A1 | 1/2013 | Huennekens et al. |
| 2013/0026655 A1 | 1/2013 | Lee et al. |
| 2013/0030295 A1 | 1/2013 | Huennekens et al. |
| 2013/0030303 A1 | 1/2013 | Ahmed et al. |
| 2013/0030410 A1 | 1/2013 | Drasler et al. |
| 2013/0053949 A1 | 2/2013 | Pintor et al. |
| 2013/0109958 A1 | 5/2013 | Baumgart et al. |
| 2013/0109959 A1 | 5/2013 | Baumgart et al. |
| 2013/0137980 A1 | 5/2013 | Waters et al. |
| 2013/0150716 A1 | 6/2013 | Stigall et al. |
| 2013/0158594 A1 | 6/2013 | Carrison et al. |
| 2013/0218201 A1 | 8/2013 | Obermiller et al. |
| 2013/0218267 A1 | 8/2013 | Braido et al. |
| 2013/0223789 A1 | 8/2013 | Lee et al. |
| 2013/0223798 A1 | 8/2013 | Jenner et al. |
| 2013/0296704 A1 | 11/2013 | Magnin et al. |
| 2013/0303907 A1 | 11/2013 | Corl |
| 2013/0303920 A1 | 11/2013 | Corl |
| 2013/0310698 A1 | 11/2013 | Judell et al. |
| 2013/0331820 A1 | 12/2013 | Itou et al. |
| 2013/0338766 A1 | 12/2013 | Hastings et al. |
| 2013/0339958 A1 | 12/2013 | Droste et al. |
| 2014/0039294 A1 | 2/2014 | Jiang |
| 2014/0180067 A1 | 6/2014 | Stigall et al. |
| 2014/0180128 A1 | 6/2014 | Corl |
| 2014/0200438 A1 | 7/2014 | Millett et al. |

FOREIGN PATENT DOCUMENTS

| | | |
|---|---|---|
| EP | 2438877 A2 | 4/2012 |
| GB | 2280261 A | 1/1995 |
| JP | 2000-262461 A | 9/2000 |
| JP | 2000-292260 A | 10/2000 |
| JP | 2001-125009 A | 5/2001 |
| JP | 2001-272331 A | 10/2001 |
| JP | 2002-374034 A | 12/2002 |
| JP | 2003-143783 A | 5/2003 |
| JP | 2003-172690 A | 6/2003 |
| JP | 2003-256876 A | 9/2003 |
| JP | 2003-287534 A | 10/2003 |
| JP | 2005-274380 A | 10/2005 |
| JP | 2006-184284 A | 7/2006 |
| JP | 2006-266797 A | 10/2006 |
| JP | 2006-313158 A | 11/2006 |
| JP | 2007-024677 A | 2/2007 |
| JP | 2009-233001 A | 10/2009 |
| JP | 2011-56786 A | 3/2011 |
| WO | 91/01156 A1 | 2/1991 |
| WO | 92/16865 A1 | 10/1992 |
| WO | 93/06213 A1 | 4/1993 |
| WO | 93/08829 A1 | 5/1993 |
| WO | 98/38907 A | 9/1998 |
| WO | 98/57583 A1 | 12/1998 |
| WO | 00/11511 A1 | 3/2000 |
| WO | 00/044296 A1 | 8/2000 |
| WO | 01/11409 A2 | 2/2001 |
| WO | 03/062802 A2 | 7/2003 |
| WO | 03/073950 A1 | 9/2003 |
| WO | 2004/010856 A1 | 2/2004 |
| WO | 2004/023992 A1 | 3/2004 |
| WO | 2004/096049 A2 | 11/2004 |
| WO | 2005/047813 A1 | 5/2005 |
| WO | 2005/106695 A2 | 11/2005 |
| WO | 2006/029634 A2 | 3/2006 |
| WO | 2006/037132 A1 | 4/2006 |
| WO | 2006/039091 A2 | 4/2006 |
| WO | 2006/061829 A1 | 6/2006 |
| WO | 2006/068875 A2 | 6/2006 |
| WO | 2006/111704 A1 | 10/2006 |
| WO | 2006/119416 A2 | 11/2006 |
| WO | 2006/121851 A2 | 11/2006 |
| WO | 2006/130802 A2 | 12/2006 |
| WO | 2007/002685 A2 | 1/2007 |
| WO | 2007/025230 A2 | 3/2007 |
| WO | 2007/045690 A1 | 4/2007 |
| WO | 2007/058895 A2 | 5/2007 |

(56) References Cited

FOREIGN PATENT DOCUMENTS

| | | | |
|---|---|---|---|
| WO | 2007/067323 | A2 | 6/2007 |
| WO | 2007/084995 | A2 | 7/2007 |
| WO | 2008/058084 | A2 | 5/2008 |
| WO | 2008/069991 | A1 | 6/2008 |
| WO | 2008/107905 | A2 | 9/2008 |
| WO | 2009/009799 | A1 | 1/2009 |
| WO | 2009/009801 | A1 | 1/2009 |
| WO | 2009/046431 | A1 | 4/2009 |
| WO | 2009/121067 | A1 | 10/2009 |
| WO | 2009/137704 | A1 | 11/2009 |
| WO | 2011/06886 | A2 | 1/2011 |
| WO | 2011/038048 | A1 | 3/2011 |
| WO | 2011/081688 | A1 | 7/2011 |
| WO | 2012/003369 | A2 | 1/2012 |
| WO | 2012/061935 | A1 | 5/2012 |
| WO | 2012/071388 | A2 | 5/2012 |
| WO | 2012/087818 | A1 | 6/2012 |
| WO | 2012/098194 | A1 | 7/2012 |
| WO | 2012/109676 | A1 | 8/2012 |
| WO | 2012109676 | A1 | 8/2012 |
| WO | 2012/130289 | A1 | 10/2012 |
| WO | 2012/154767 | A2 | 11/2012 |
| WO | 2012/155040 | A1 | 11/2012 |
| WO | 2013/033414 | A1 | 3/2013 |
| WO | 2013/033415 | A2 | 3/2013 |
| WO | 2013/033418 | A1 | 3/2013 |
| WO | 2013/033489 | A1 | 3/2013 |
| WO | 2013/033490 | A1 | 3/2013 |
| WO | 2013/033592 | A1 | 3/2013 |
| WO | 2013/126390 | A1 | 8/2013 |
| WO | 2014/109879 | A1 | 7/2014 |

OTHER PUBLICATIONS

International Search Report and Written Opinion dated Apr. 14, 2014, for International Patent Application No. PCT/US2013/076148, filed Dec. 18, 2013 (8 pages).
International Search Report and Written Opinion dated Apr. 21, 2014, for International Patent Application No. PCT/US2013/076015, filed Dec. 18, 2013 (7 pages).
International Search Report and Written Opinion dated Apr. 23, 2014, for International Patent Application No. PCT/US2013/075328, filed Dec. 16, 2013 (8 pages).
International Search Report and Written Opinion dated Apr. 29, 2014, for International Patent Application No. PCT/US13/76093, filed Dec. 18, 2013 (6 pages).
International Search Report and Written Opinion dated Apr. 9, 2014, for International Patent Application No. PCT/US13/75089, filed Dec. 13, 2013 (7 pages).
International Search Report and Written Opinion dated Feb. 21, 2014, for International Patent Application No. PCT/US13/76053, filed Dec. 18, 2013 (9 pages).
International Search Report and Written Opinion dated Feb. 21, 2014, for International Patent Application No. PCT/US2013/076965, filed Dec. 20, 2013 (6 pages).
International Search Report and Written Opinion dated Feb. 27, 2014, for International Patent Application No. PCT/US13/75416, filed Dec. 16, 2013 (7 pages).
International Search Report and Written Opinion dated Feb. 28, 2014, for International Patent Application No. PCT/US13/75653, filed Dec. 17, 2013 (7 pages).
International Search Report and Written Opinion dated Feb. 28, 2014, for International Patent Application No. PCT/US13/75990, filed Dec. 18, 2013 (7 pages).
International Search Report and Written Opinion dated Jan. 16, 2009, for International Patent Application No. PCT/US08/78963 filed on Oct. 6, 2008 (7 Pages).
International Search Report and Written Opinion dated Jul. 30, 2014, for International Patent Application No. PCT/US14/21659, filed Mar. 7, 2014 (15 pages).
International Search Report and Written Opinion dated Mar. 10, 2014, for International Patent Application No. PCT/US2013/076212, filed Dec. 18, 2013 (8 pages).
International Search Report and Written Opinion dated Mar. 11, 2014, for International Patent Application No. PCT/US13/76173, filed Dec. 16, 2013 (9 pages).
International Search Report and Written Opinion dated Mar. 11, 2014, for International Patent Application No. PCT/US13/76449, filed Dec. 19, 2013 (9 pages).
International Search Report and Written Opinion dated Mar. 18, 2014, for International Patent Application No. PCT/US2013/076502, filed Dec. 19, 2013 (7 pages).
International Search Report and Written Opinion dated Mar. 18, 2014, for International Patent Application No. PCT/US2013/076788, filed Dec. 20, 2013 (7 pages).
International Search Report and Written Opinion dated Mar. 19, 2014, for International Patent Application No. PCT/US13/75349, filed Dec. 16, 2013 (10 pages).
International Search Report and Written Opinion dated Mar. 19, 2014, for International Patent Application No. PCT/US2013/076587, filed Dec. 19, 2013 (10 pages).
International Search Report and Written Opinion dated Mar. 19, 2014, for International Patent Application No. PCT/US2013/076909, filed Dec. 20, 2013 (7 pages).
International Search Report and Written Opinion dated Mar. 7, 2014, for International Patent Application No. PCT/US2013/076304, filed Dec. 18, 2013 (9 pages).
International Search Report and Written Opinion dated Mar. 7, 2014, for International Patent Application No. PCT/US2013/076480, filed Dec. 19, 2013 (8 pages).
International Search Report and Written Opinion dated Mar. 7, 2014, for International Patent Application No. PCT/US2013/076512, filed Dec. 19, 2013 (8 pages).
International Search Report and Written Opinion dated Mar. 7, 2014, for International Patent Application No. PCT/US2013/076531, filed Dec. 19, 2013 (10 pages).
Jakobovits et al., 1993, Analysis of homozygous mutant chimeric mice:deletion of the immunoglobulin heavy-chain joining region blocks B-cell development and antibody production, PNAS USA 90:2551-255.
Jakobovits et al., 1993, Germ-line transmission and expression of a human-derived yeast artificial chromosome, Nature 362:255-258.
Jang et al., 2002, Visualization of Coronary Atherosclerotic Plaques in Patients Using Optical Coherence Tomography: Comparison With Intravascular Ultrasound, Journal of the American College of Cardiology 39:604-609.
Jiang et al., 1992, Image registration of multimodality 3-D medical images by chamfer matching, Proc. SPIE 1660, Biomedical Image Processing and Three-Dimensional Microscopy, 356-366.
Johnson et al., 1993, Human antibody engineering: Current Opinion in Structural Biology, 3:564-571.
Jones et al., 1986, Replacing the complementarity-determining regions in a human antibody with those from a mouse, Nature, 321:522-525.
Juviler et al., 2008, Anorectal sepsis and fistula-in-ano, Surgical Technology International, 17:139-149.
Karapatis et al., 1998, Direct rapid tooling:a review of current research, Rapid Prototyping Journal, 4(2):77-89.
Karp et al., 2009, The benefit of time-of-flight in PET imaging, J Nucl Med 49:462-470.
Kelly et al., 2005, Detection of Vascular Adhesion Molecule-1 Expression Using a Novel Multimodal Nanoparticle, Circulation Research 96:327-336.
Kemp et al., 2005, Depth Resolved Optic Axis Orientation in Multiple Layered Anisotropic Tissues Measured with Enhanced Polarization Sensitive Optical Coherence Tomography, Optics Express 13(12):4507-4518.
Kersey et al., 1991, Polarization insensitive fiber optic Michelson interferometer, Electron. Lett. 27:518-520.
Kheir et al., 2012, Oxygen Gas-Filled Microparticles Provide Intravenous Oxygen Delivery, Science Translational Medicine 4(140):140ra88 (10 pages).

(56) References Cited

OTHER PUBLICATIONS

Khuri-Yakub et al., 2011, Capacitive micromachined ultrasonic transducers for medical imaging and therapy, J Micromech Microeng. 21(5):054004-054014.
Kirkman, 1991, Technique for flow reduction in dialysis access fistulas, Surg Gyn Obstet, 172(3):231-3.
Kohler et al., 1975, Continuous cultures of fused cells secreting antibody of predefined specificity, Nature, 256:495-7.
Koo et al., 2011, Diagnosis of IschemiaCausing Coronary Stenoses by Noninvasive Fractional Flow Reserve Computed From Coronary Computed Tomographic Angiograms, J Am Coll Cardiol 58(19):1989-1997.
Kozbor et al., 1984, A human hybrid myeloma for production of human monoclonal antibodies, J. Immunol., 133:3001-3005.
Kruth et al., 2003, Lasers and materials in selective laser sintering, Assembly Automation, 23(4):357-371.
Kumagai et al., 1994, Ablation of polymer films by a femtosecond high-peak-power Ti:sapphire laser at 798 nm, Applied Physics Letters, 65(14):1850-1852.
Larin et al., 2002, Noninvasive Blood Glucose Monitoring with Optical Coherence Tomography: a pilot study in human subjects, Diabetes Care, 25(12):2263-7.
Larin et al., 2004, Measurement of Refractive Index Variation of Physiological Analytes using Differential Phase OCT, Proc of SPIE 5325:31-34.
Laufer, 1996, Introduction to Optics and Lasers in Engineering, Cambridge University Press, Cambridge UK:156-162.
Lefevre et al., 2001, Stenting of bifurcation lesions:a rational approach, J. Interv. Cardiol., 14(6):573-585.
Li et al., 2000, Optical Coherence Tomography: Advanced Technology for the Endoscopic Imaging of Barrett's Esophagus, Endoscopy, 32(12):921-930.
Abdi et al., 2010, Principal component analysis, Wiley Interdisciplinary Reviews: Computational Statistics 2:433-459.
Adler et al., 2007, Phase-Sensitive Optical Coherence Tomography at up to 370,000 Lines Per Second Using Buffered Fourier Domain Mode-Locked Lasers, Optics Letters, 32(6):626-628.
Agresti, 1996, Models for Matched Pairs, Chapter 8, An Introduction to Categorical Data Analysis, Wiley-Interscience A John Wiley & Sons, Inc., Publication, Hoboken, New Jersey.
Akasheh et al., 2004, Development of piezoelectric micromachined ultrasonic transducers, Sensors and Actuators A Physical, 111:275-287.
Amini et al., 1990, Using dynamic programming for solving variational problems in vision, IEEE Transactions on Pattern Analysis and Machine Intelligence, 12(9):855-867.
Bail et al., 1996, Optical coherence tomography with the "Spectral Radar"-Fast optical analysis in volume scatterers by short coherence interferometry, Optics Letters 21(14):1087-1089.
Bain, 2011, Privacy protection and face recognition, Chapter 3, Handbook of Face Recognition, Stan et al., Springer-Verlag.
Barnea et al., 1972, A class of algorithms for fast digital image registration, IEEE Trans. Computers, 21(2):179-186.
Blanchet et al., 1993, Laser Ablation and the Production of Polymer Films, Science, 262(5134):719-721.
Bonnema, 2008, Imaging Tissue Engineered Blood Vessel Mimics with Optical Tomography, College of Optical Sciences dissertation, University of Arizona (252 pages).
Bouma et al., 1999, Power-efficient nonreciprocal interferometer and linear-scanning fiber-optic catheter for optical coherence tomography, Optics Letters, 24(8):531-533.
Breiman, 2001, Random forests, Machine Learning 45:5-32.
Brown, 1992, A survey of image registration techniques, ACM Computing Surveys 24(4):325-376.
Bruining et al., 2009, Intravascular Ultrasound Registration/Integration with Coronary Angiography, Cardiology Clinics, 27(3):531-540.

Brummer, 1997, An euclidean distance measure between covariance matrices of speechcepstra for text-independent speaker recognition, in Proc. South African Symp. Communications and Signal Processing:167-172.
Burr et al., 2005, Searching for the Center of an Ellipse in Proceedings of the 17th Canadian Conference on Computational Geometry:260-263.
Canny, 1986, A computational approach to edge detection, IEEE Trans. Pattern Anal. Mach. Intell. 8:679-698.
Cavalli et al., 2010, Nanosponge formulations as oxygen delivery systems, International Journal of Pharmaceutics 402:254-257.
Choma et al., 2003, Sensitivity Advantage of Swept Source and Fourier Domain Optical Coherence Tomography, Optics Express 11(18):2183-2189.
Clarke et al., 1995, Hypoxia and myocardial ischaemia during peripheral angioplasty, Clinical Radiology, 50(5):301-303.
Collins, 1993, Coronary flow reserve, British Heart Journal 69:279-281.
Communication Mechanisms for Distributed Real-Time Applications, NI Developer Zone, http://zone.ni.com/devzone/cda/tut/p/id/3105, accessed Jul. 23, 2007.
Cook, 2007, Use and misuse of receiver operating characteristic curve in risk prediction, Circulation 115(7):928-35.
D'Agostino et al., 2001, Validation of the Framingham coronary heart disease prediction score: results of a multiple ethnic group investigation, JAMA 286:180-187.
David et al., 1974, Protein iodination with solid-state lactoperoxidase, Biochemistry 13:1014-1021.
Davies et al., 1985, Plaque fissuring-the cause of acute myocardial infarction, sudden ischaemic death, and crescendo angina, British Heart Journal 53:363-373.
Davies et al., 1993, Risk of thrombosis in human atherosclerotic plaques: role of extracellular lipid, macrophage, and smooth muscle cell content, British Heart Journal 69:377-381.
Deterministic Data Streaming in Distributed Data Acquisition Systems, NI Developer Zone, "What is Developer Zone?", http://zone.ni.com/devzone/cda/tut/p/id/3105, accessed Jul. 23, 2007.
Eigenwillig, 2008, K-Space Linear Fourier Domain Mode Locked Laser and Applications for Optical Coherence Tomography, Optics Express 16(12):8916-8937.
Elghanian et al., 1997, Selective colorimetric detection of polynucleotides based on the distance-dependent optical properties of gold nanoparticles, Science, 277(5329):1078-1080.
Ergun et al., 2003, Capacitive Micromachined Ultrasonic Transducers: Theory and Technology, Journal of Aerospace Engineering, 16(2):76-84.
Evans et al., 2006, Optical coherence tomography to identify intramucosa carcinoma and high-grade dysplasia in Barrett's esophagus, Clin Gast Hepat 4(1):38-43.
Fatemi et al., 1999, Vibro-acoustography: an imaging modality based on ultrasound-stimulated acoustic emission, PNAS U.S.A., 96(12):6603-6608.
Felzenszwalb et al., 2005, Pictorial Structures for Object Recognition, International Journal of Computer Vision, 61(1):55-79.
Ferring et al., 2008, Vasculature ultrasound for the pre-operative evaluation prior to arteriovenous fistula formation for haemodialysis: review of the evidence, Nephrol. Dial. Transplant. 23(6):1809-1815.
Fischler et al., 1973, The representation and matching of pictorial structures, IEEE Transactions on Computer 22:67-92.
Fleming et al., 2010, Real-time monitoring of cardiac radiofrequency ablation lesion formation using an optical coherence tomography forward-imaging catheter, Journal of Biomedical Optics 15 (3):030516-1 (3 pages).
Fookes et al., 2002, Rigid and non-rigid image registration and its association with mutual information:A review, Technical Report ISBN:1 86435 569 7, RCCVA, QUT.
Forstner & Moonen, 1999, A metric for covariance matrices, In Technical Report of the Dpt of Geodesy and Geoinformatics, Stuttgart University, 113-128.
Goel et al., 2006, Minimally Invasive Limited Ligation Endoluminal-assisted Revision (MILLER) for treatment of dialysis access-associated steal syndrome, Kidney Int 70(4):765-70.

(56) References Cited

OTHER PUBLICATIONS

Gotzinger et al., 2005, High speed spectral domain polarization sensitive optical coherence tomography of the human retina, Optics Express 13(25):10217-10229.
Gould et al., 1974, Physiologic basis for assessing critical coronary stenosis, American Journal of Cardiology, 33:87-94.
Griffiths et al., 1993, Human anti-self antibodies with high specificity from phage display libraries, The EMBO Journal, 12:725-734.
Griffiths et al., 1994, Isolation of high affinity human antibodies directly from large synthetic repertoires, The EMBO Journal, 13(14):3245-3260.
Grund et al., 2010, Analysis of biomarker data:logs, odds, ratios and ROC curves, Curr Opin HIV AIDS 5(6):473-479.
Harrison et al., 2011, Guidewire Stiffness: What's in a name?, J Endovasc Ther, 18(6):797-801.
Huber et al., 2005, Amplified, Frequency Swept Lasers for Frequency Domain Reflectometry and OCT Imaging: Design and Scaling Principles, Optics Express 13(9):3513-3528.
Huber et al., 2006, Fourier Domain Mode Locking (FDML): A New Laser Operating Regime and Applications for Optical Coherence Tomography, Optics Express 14(8):3225-3237.
International Search Report and Written Opinion dated Mar. 11, 2014, for International Patent Application No. PCT/US13/75675, filed Dec. 17, 2013 (7 pages).
International Search Report and Written Opinion dated Mar. 19, 2014, for International Patent Application No. PCT/US13/075,353, filed Dec. 16, 2013 (8 pages).
Little et al., 1991, The underlying coronary lesion in myocardial infarction:implications for coronary angiography, Clinica Cardiology, 14(11):868-874.
Loo, 2004, Nanoshell Enabled Photonics-Based Imaging and Therapy of Cancer, Technology in Cancer Research & Treatment 3(1):33-40.
Machine translation of JP 2000-097846.
Machine translation of JP 2000-321034.
Machine translation of JP 2000-329534.
Machine translation of JP 2004-004080.
Maintz et al., 1998, An Overview of Medical Image Registration Methods, Technical Report UU-CS, (22 pages).
Mamas et al., 2010, Resting Pd/Pa measured with intracoronary pressure wire strongly predicts fractional flow reserve, Journal of Invasive Cardiology 22(6):260-265.
Marks et al., 1991, By-passing Immunization Human Antibodies from V-gene Libraries Displayed on Phage, J. Mol. Biol. 222:581-597.
Marks et al., 1992, By-Passing Immunization:Building High Affinity Human Antibodies by Chain Shuffling, BioTechnol., 10:779-783.
Maruno et al., 1991, Fluorine containing optical adhesives for optical communications systems, J. Appl. Polymer. Sci. 42:2141-2148.
McCafferty et al., 1990, Phage antibodies: filamentous phage displaying antibody variable domains, Nature 348:552-554.
Mendieta et al., 1996, Complementary sequence correlations with applications to reflectometry studies, Instrumentation and Development 3(6):37-46.
Mickley, 2008, Steal Syndrome-strategies to preserve vascular access and extremity, Nephrol Dial Transplant 23:19-24.
Miller et al., 2010, The MILLER banding procedure is an effective method for treating dialysis-associated steal syndrome, Kidney International 77:359-366.
Milstein et al., 1983, Hybrid hybridomas and their use in immunohistochemistry, Nature 305:537-540.
Mindlin et al., 1936, A force at a point of a semi-infinite solid, Physics, 7:195-202.
Morrison et al., 1984, Chimeric human antibody molecules: mouse antigen-binding domains with human constant region domains, PNAS 81:6851-6855.
Munson et al., 1980, Ligand: a versatile computerized approach for characterization of ligand-binding systems, Analytical Biochemistry, 107:220-239.

Nezam, 2008, High Speed Polygon-Scanner-Based Wavelength-Swept Laser Source in the Telescope-Less Configurations with Application in Optical Coherence Tomography, Optics Letters 33(15):1741-1743.
Nissen, 2001, Coronary Angiography and Intravascular Ultrasound, American Journal of Cardiology, 87(suppl):15A-20A.
Nitenberg et al., 1995, Coronary vascular reserve in humans: a critical review of methods of evaluation and of interpretation of the results, Eur Heart J. 16(Suppl 1):7-21.
Notice of Reason(s) for Refusal dated Apr. 30, 2013, for Japanese Patent Application No. 2011-508677 for Optical Imaging Catheter for Aberation Balancing to Volcano Corporation, which application is a Japanese national stage entry of PCT/US2009/043181 with international filing date May 7, 2009, of the same title, published on Nov. 12, 2009, as WO 2009/137704, and accompanying English translation of the Notice of Reason(s) for Refusal and machine translations of JP11-56786 and JP2004-290548 (56 pages).
Nygren, 1982, Conjugation of horseradish peroxidase to Fab fragments with different homobifunctional and heterobifunctional cross-linking reagents. A comparative study, J. Histochem. and Cytochem. 30:407-412.
Oesterle et al., 1986, Angioplasty at coronary bifurcations: single-guide, two-wire technique, Cathet Cardiovasc Diagn., 12:57-63.
Okuno et al., 2003, Recent Advances in Optical Switches Using Silica-based PLC Technology, NTT Technical Review 1(7):20-30.
Oldenburg et al., 1998, Nanoengineering of Optical Resonances, Chemical Physics Letters 288:243-247.
Oldenburg et al., 2003, Fast-Fourier-Domain Delay Line for In Vivo Optical Coherence Tomography with a Polygonal Scanner, Applied Optics, 42(22):4606-4611.
Othonios, 1997, Fiber Bragg gratings, Review of Scientific Instruments 68(12):4309-4341.
Owens et al., 2007, A Survey of General-Purpose Computation on Graphics Hardware, Computer Graphics Forum 26(1):80-113.
Pain et al., 1981, Preparation of protein A-peroxidase mono conjugate using a heterobifunctional reagent, and its use in enzyme immunoassays, J Immunol Methods, 40:219-30.
Park et al., 2005, Real-time fiber-based multi-functional spectral-domain optical coherence tomography at 1.3 um., Optics Express 13(11):3931-3944.
Pasquesi et al., 2006, In vivo detection of exercise induced ultrastructural changes in genetically-altered murine skeletal muscle using polarization-sensitive optical coherence tomography, Optics Express 14(4):1547-1556.
Pepe et al., 2004, Limitations of the odds ratio in gauging the performance of a diagnostic, prognostic, or screening marker, American Journal of Epidemiology 159(9):882-890.
Persson et al., 1985, Acoustic impedance matching of medical ultrasound transducers, Ultrasonics, 23(2):83-89.
Placht et al., 2012, Fast time-of-flight camera based surface registration for radiotherapy patient positioning, Medical Physics 39(1):4-17.
Rabbani et al., 1999, Review: Strategies to achieve coronary arterial plaque stabilization, Cardiovascular Research 41:402-417.
Radvany et al., 2008, Plaque Excision in Management of Lower Extremity Peripheral Arterial Disease with the SilverHawk Atherectomy Catheter, Seminars in Interventional Radiology, 25(1):11-19.
Reddy et al., 1996, An FFT-Based Technique for Translation, Rotation, and Scale-Invariant Image Registration, IEEE Transaction on Image Processing 5(8):1266-1271.
Riechmann et al., 1988, Reshaping human antibodies for therapy, Nature, 332:323-327.
Rivers et al., 1992, Correction of steal syndrome secondary to hemodialysis access fistulas: a simplified quantitative technique, Surgery, 112(3):593-7.
Robbin et al., 2002, Hemodialysis Arteriovenous Fistula Maturity: US Evaluation, Radiology 225:59-64.
Rollins et al., 1998, In vivo video rate optical coherence tomography, Optics Express 3:219-229.
Sarunic et al., 2005, Instantaneous Complex Conjugate Resolved Spectral Domain and Swept-Source OCT Using 3x3 Fiber Couplers, Optics Express 13(3):957-967.

(56) References Cited

OTHER PUBLICATIONS

Satiani et al., 2009, Predicted Shortage of Vascular Surgeons in the United States, J. Vascular Surgery 50:946-952.
Schneider et al., 2006, T-banding: A technique for flow reduction of a hyper-functioning arteriovenous fistula, J Vasc Surg. 43(2):402-405.
Sen et al., 2012, Development and validation of a new adenosine-independent index of stenosis severity from coronary wave-intensity analysis, Journal of the American College of Cardiology 59(15):1392-1402.
Setta et al., 2005, Soft versus firm embryo transfer catheters for assisted reproduction: a systematic review and meta-analysis, Human Reproduction, 20(11):3114-3121.
Seward et al., 1996, Ultrasound Cardioscopy: Embarking on New Journey, Mayo Clinic Proceedings 71(7):629-635.
Shen et al., 2006, Eigengene-based linear discriminant model for tumor classification using gene expression microarray data, Bioinformatics 22(21):2635-2642.
Sihan et al., 2008, A novel approach to quantitative analysis of intraluminal optical coherence tomography imaging, Comput. Cardiol: 1089-1092.
Siwy et al., 2003, Electro-responsive asymmetric nanopores in polyimide with stable ion-current signal, Applied Physics A: Materials Science & Processing 76:781-785.
Smith et al., 1989, Absolute displacement measurements using modulation of the spectrum of white light in a Michelsor interferometer, Applied Optics, 28(16):3339-3342.
Smith, 1997, The Scientist and Engineer's Guide to Digital Signal Processing, California Technical Publishing, San Diego, CA:432-436.
Soller, 2003, Polarization diverse optical frequency domain interferometry:All coupler implementation, Bragg Grating, Photosensitivity, and Poling in Glass Waveguides Conference MB4:30-32.
Song et al., 2012, Active tremor cancellation by a "Smart" handheld vitreoretinal microsurgical tool using swept source optical coherence tomography, Optics Express, 20(21):23414-23421.
Stenqvist et al., 1983, Stiffness of central venous catheters, Acta Anaesthesiol Scand., 2:153-157.
Strickland, 1970, Time-Domain Reflectometer Measurements, Tektronix, Beaverton, OR, (107 pages).
Strobl et al., 2009, An Introduction to Recursive Partitioning:Rationale, Application and Characteristics of Classification and Regression Trees, Bagging and Random Forests, Psychol Methods., 14(4):323-348.
Sutcliffe et al., 1986, Dynamics of UV laser ablation of organic polymer surfaces, Journal of Applied Physics, 60(9):3315-3322.
Suzuki, 2013, A novel guidewire approach for handling acute-angle bifurcations, J Inv Cardiol 25(1):48-54.
Tanimoto et al., 2008, A novel approach for quantitative analysis of intracoronary optical coherence tomography: high inter-observer agreement with computer-assisted contour detection, Cathet Cardiovascular Intervent., 72(2):228-235.
Teamey et al., 1997, In vivo Endoscopic Optical Biopsy with Optical Coherence Tomography, Science, 276:2037-2039.
Tonino et al., 2009, Fractional flow reserve versus angiography for guiding percutaneous coronary intervention, The New England Journal of Medicine, 360:213-224.
Toregeani et al., 2008, Evaluation of hemodialysis arteriovenous fistula maturation by color-flow Doppler ultrasound, J Vasc. Bras. 7(3):203-213.
Translation of Notice of Reason(s) for Refusal dated Apr. 30, 2014, for Japanese Patent Application No. 2011-508677, (5 pages).
Translation of Notice of Reason(s) for Refusal dated May 25, 2012, for Japanese Patent Application No. 2009-536425, (3 pages).
Translation of Notice of Reason(s) for Refusal dated Nov. 22, 2012, for Japanese Patent Application No. 2010-516304, (6 pages).
Traunecker et al., 1991, Bispecific single chain molecules (Janusins) target cytotoxic lymphocytes on HIV infected cells EMBO J., 10:3655-3659.
Trolier-McKinstry et. al., 2004, Thin Film Piezoelectric for MEMS, Journal of Electroceramics 12:7-17.
Tuniz et al., 2010, Weaving the invisible thread: design of an optically invisible metamaterial fibre, Optics Express 18(17):18095-18105.
Turk et al., 1991, Eigenfaces for Recognition, Journal of Cognitive Neuroscience 3(1):71-86.
Tuzel et al., 2006, Region Covariance: A Fast Descriptor for Detection and Classification, European Conference on Computer Vision (ECCV).
Urban et al., 2010, Design of a Pressure Sensor Based on Optical Bragg Grating Lateral Deformation, Sensors (Basel), 10(12):11212-11225.
Vakhtin et al., 2003, Common-path interferometer for frequency-domain optical coherence tomography, Applied Optics, 42(34):6953-6958.
Vakoc et al., 2005, Phase-Resolved Optical Frequency Domain Imaging, Optics Express 13(14):5483-5493.
Verhoeyen et al., 1988, Reshaping human antibodies: grafting an antilysozyme activity, Science, 239:1534-1536.
Villard et al., 2002, Use of a blood substitute to determine instantaneous murine right ventricular thickening with optical coherence tomography, Circulation, 105:1843-1849.
Wang et al., 2002, Optimizing the Beam Patten of a Forward-Viewing Ring-Annular Ultrasound Array for Intravascular Imaging, Transactions on Ultrasonics, Ferroelectrics, and Frequency Control, 49(12).
Wang et al., 2006, Multiple biomarkers for the prediction of first major cardiovascular events and death, The New England Journal of Medicine, 355(25):2631-2639.
Wang et al., 2009, Robust Guidewire Tracking in Fluoroscopy, IEEE Conference on Computer Vision and Pattern Recognition—CVPR 2009:691-698.
Wang et al., 2011, In vivo intracardiac optical coherence tomography imaging through percutaneous access: toward image-guided radio-frequency ablation, J. Biomed. Opt. 0001 16(11):110505-1 (3 pages).
Waterhouse et. al., 1993, Combinatorial infection and in vivo recombination: a strategy for making large phage antibody repertoires, Nucleic Acids Res., 21:2265-2266.
Wegener, 2011, 3D Photonic Metamaterials and Invisibility Cloaks: The Method of Making, MEMS 2011, Cancun, Mexico, Jan. 23-27, 2011.
West et al., 1991, Arterial insufficiency in hemodialysis access procedures: correction by banding technique, Transpl Proc 23(2):1838-40.
Wyawahare et al., 2009, Image registration techniques: an overview, International Journal of Signal Processing, Image Processing and Pattern Recognition, 2(3):11-28.
Yaqoob et al., 2006, Methods and application areas of endoscopic optical coherence tomography, J. Biomed. Opt., 11, 063001-1-063001-19.
Yasuno et al., 2004, Polarization-sensitive complex Fourier domain optical coherence tomography for Jones matrix imaging of biological samples, Applied Physics Letters 85(15):3023-3025.
Zhang et al., 2004, Full range polarization-sensitive Fourier domain optical coherence tomography, Optics Express, 12(24):6033-6039.
Zitova et al., 2003, Image registration methods: A survey. Image and Vision Computing, 21(11):977-1000.

SYSTEM AND METHOD FOR INSTANT AND AUTOMATIC BORDER DETECTION

CROSS-REFERENCE TO RELATED APPLICATIONS

This application is a continuation of U.S. application Ser. No. 14/047,119, filed Oct. 7, 2013, now U.S. Pat. No. 1,172,831, which claims priority to, and the benefit of, U.S. Provisional Application 61/710,401, filed Oct. 5, 2012, and U.S. Provisional Application 61/739,920, filed Dec. 20, 2021, the contents of each of which are incorporated by reference.

FIELD OF THE INVENTION

The invention generally relates to medical imaging systems that instantly and automatically detect borders.

BACKGROUND

Blood vessels include three layers—the intima surrounded by the media and then the adventitia. The intima includes an elastic lamina lined with the endothelium—a layer of endothelial cells in direct contact with circulating blood that aids in wound healing and immune function. The inner surface of the endothelium defines the luminal border—the passage through which blood can flow. The media is mostly smooth muscle with some other material. The adventitia is mostly collagen that anchors the blood vessel within its environment.

Debris such as macrophage cells, lipids, and cholesterol can accumulate between the endothelium and the smooth muscle of the media, causing plaques in the arteries surrounded by the medial border, a condition known as atherosclerosis. For many people, the first symptom of atherosclerosis is a heart attack.

Atherosclerosis can be deadly because the plaque can block the flow of blood through arteries. Using intravascular imaging systems, a physician can find the luminal border and the medial border. The space between these two borders gives a measurement of plaque thickness. The thicker the plaque, the smaller the passage defined by the luminal border, and the more severe the atherosclerosis.

Some imaging systems have tools to help locate the borders. These tools typically require moving the imaging tip into place and then switching from the positioning joystick to the computer stand to trigger a border-detection application and then back to the joystick to try for a better position. This leads to a back-and-forth workflow as the doctor tries to zero in on the most occluded part of the artery. The back-and-forth work pattern builds up the time the patient must have the catheter inserted into their body, bringing risks of medical complications. Due to the time required for switching back-and-forth between border detection and navigation, tensions among the doctors and attending staff can be inflamed. Particularly because the additional steps are imposed at a stage of the procedure that is so critical to preventing heart attacks, the inflamed tensions are aggravated and the procedure progresses slowly and imperfectly.

SUMMARY

The invention provides an imaging system that automatically detects a border at a location within a vessel in response only to navigational input. The invention allow near-instantaneous location of borders when a catheter is delivered to a location or to a new location.

Without removing his hands from the navigational controller, a doctor may move from location to location, detecting borders automatically at each location. The automatically detected border can be displayed, for example, as a line drawn over the tissue on the imaging system monitor. Additionally or alternatively, the border can be used in analysis. For example, a ratio of areas defined by the luminal and medial borders can be calculate and used to give a doctor a measure of occlusion in an artery. Since the measure of occlusion, based on the automatically detected border, is delivered to the doctor instantly as he navigates through the tissue, the doctor may smoothly navigate straight to the most severely affected spot in the arteries. The system's ease of use allows the doctor and staff to maintain calm and harmonious dispositions. This allows for a trouble-free imaging procedure which, in turn, allows the doctor and staff to give their full attention to the health of the patient.

In certain aspects, the invention provides a method for examining tissue that includes receiving data for a three-dimensional image of tissue and displaying an image of part of the tissue. An operator provides navigational input to direct the display to a selected portion of the tissue and the method includes responding solely to that navigational input by detecting a location of a border within the selected portion of the tissue and displaying the selected portion of the tissue. The data may be obtained by obtained by performing an intravascular imaging operation such as an intravascular ultrasound (IVUS) operation. The image can be displayed on a computer monitor, allowing the operator to navigate through the patient's vessel on-screen. Operator navigation can be performed using a controller device, such as a joystick, mouse, or other pointer, and the operator's gestures with the device provide both the navigational directions and the signal to provide a detected border. Preferably, the border is detected in response to the navigational input, more specifically, preferably in response to cessation of the navigational input. The border may be detected substantially instantly, e.g., within less than about a second from the cessation of navigation. This can be provided by a detection algorithm, such as a morphological image processing operation. The detected border or borders can be displayed as, for example, an overlay on the monitor for the user. The detected borders can also be used to calculate how occluded a vessel is by atheroma. For example, a ratio of areas associated with a luminal border of vessel and a medial-adventitial border of the vessel can be used to calculate a percent occlusion. In certain embodiments, detecting the location of the border includes approximating a border within a first frame of the three-dimensional image, identifying at least one control point on the border, extrapolating the at least one control point to approximate a second border in a second frame of the three-dimensional image and optionally adjusting the second border in accordance with a frequency factor.

In related aspects, the invention provides an intravascular imaging system that includes an imaging catheter with an image capture device such as a piezoelectric transducer at a distal portion of the imaging catheter and a processing system operably coupled to a proximal portion of the catheter. The processing system includes a memory and processor so that the system can be used to receive data for a three-dimensional image of tissue and display an image of part of the tissue. The system is operable to receive navigational input that directs the display to a selected portion of the tissue and to respond solely to the navigational input by detecting a location of a border within the selected portion of the tissue and displaying the selected portion of the tissue. Preferably the system includes one or more computer monitors for displaying the images, the detected borders, calculated values, other information, or combinations thereof.

In other aspects, the invention provides a method of examining tissue that includes performing an intravascular imaging operation to see a patient's vessel (e.g., on a monitor) and using a pointing device to change the view. When the operator stops the image at a certain spot within the vessel, a system provides, responsive only to the ceasing of the use of the pointing device, data that includes a location of an automatically detected feature within the selected portion of the vessel. In some embodiments, the system detects the border in response only to the cessation of navigation.

Other aspects of the invention generally provide systems and methods for the automatic detection of vessel lumen borders. The lumen border is calculated in a set of two dimensional images using three dimensional data, while a three dimensional image of the vessel is concurrently generated. The user is provided with a three dimensional vessel image in which the lumen border has already been determined, thus eliminating the need for a user to manually draw the lumen border of the vessel in the fully constructed image. Accordingly, systems and methods of the invention save clinician's time and eliminate intra- and inter-observer variability.

The systems and methods of the invention improve the speed at which users can analyze a data set due to the automation of the border detection. In some aspects, the systems and methods of the invention also provide annotation of important vessel metrics (e.g. the minimum and maximum diameter and total area measurements), allowing the clinician to rapidly identify a specific region of interest in the three dimensional image set.

The invention may be applicable to data from image gathering devices that acquire two dimensional data sets from which three dimensional image compositions are derived, for example any tomographic device such as optical coherence tomography (OCT), photo acoustic imaging devices and ultrasound devices, including, but not limited to, intravascular ultrasound spectroscopy (IVUS), and other catheter-based or rotational tomographic imaging technologies.

Through the use of the image processing techniques described herein, the vascular structure border for all imaging frames, or any subsets, in a recorded data set are detected and provided to the user. Corresponding diameter and area measurements are provided to the user in the three dimensional image by these methods. The resulting lumen border may be displayed as the final tomographic image, the image longitudinal display (ILD), splayed image and three dimensional image. User interface graphics provide input for other indicators on a monitor interface, such as a color bar indicating the size of the lumen. The method and system eliminates the need for a clinician to draw manually the border thereby reducing user error. Additionally, the minimum and maximum diameter and lumen area can be derived easily from these automatic detection methods.

In certain aspects, the invention described generally relates to a method for displaying a medical image, for example an optical coherence tomography image, of a lumen of a biological structure through the acquisition of image data with a medical imaging device, processing the data to identify a lumen border of the biological structure, and concurrently generating a three dimensional image of the lumen border of the biological structure for display. In other aspects, the invention generally provides a system for displaying a medical image of a lumen of a biological structure. The system uses a monitor to display an image of the lumen of a biological structure, a central processing unit (CPU), and storage coupled to the CPU for storing instructions that configure the CPU to receive image data of a biological structure from a medical imaging device, process the data to identify a lumen border of the biological structure, and generate a three dimensional image of the biological structure including the identified lumen border. Processing the data may involve identifying a location of edges in the image data, removing edge detections where shadows are located, and calculating a lumen border. The processing step and the generating step occur concurrently, and provide data to display the three dimensional image on the monitor. Systems and methods use, for example, a medical imaging device such as an optical coherence tomography (OCT) catheter providing OCT imaging data.

In certain aspects, a multi-step process removes shadow artifacts from the image device that appear in the lumen edge. In an exemplary embodiment that involves OCT, the first step involves detecting a maximum amplitude data point in an acquired A-scan, followed by determining noise floor amplitude for the A-scan and removing from the A-scan a data point with an amplitude in the range of at least one pre-determined parameter to construct a modified A-scan. The process may further involve calculating a B-scan from the modified A-scan. In certain aspects, the modified A-scans and B-scans can be further processed with a two-dimensional median filter.

Processing the data may also include smoothing the lumen border, and may be accomplished in an exemplary embodiment by identifying a set of seed points in the image data and adjusting the lumen border based upon at least some of the seed points. In embodiments that involve OCT, adjusting may involve interpolating a lumen border in an A-scan using a combination of data points in at least one neighboring frame, an interpolated data point, and a pair of seed points, and storing the smoothed lumen border data to a memory device. The interpolated data point may be at about the midpoint between a pair of seed points, and the seed points may be data points identifying a location of edges in the image data. The data points may be at a corresponding polar coordinate position in an A-scan or across frames. In some aspects, adjusting also involves evaluating interpolated data points that are artifacts due to non-lumen intravascular tissue in contact with an imaging device, and removing the artifacts.

The calculating step, when processing the data, may also be a multistep process. The first step may involve interpolating a lumen border from at least one pair of seed points, then determining an area between an interpolated lumen border and a lumen border from data points identifying a location of edges in the image data for all interpolated lumen borders, selecting the lumen border correlated with the smallest area, and storing the lumen border with the smallest area to a memory device. The seed points may be at least one set of data points identifying a location of edges in the image data.

In certain instances, the calculating and smoothing steps may apply a weighting function to bias a calculated data point. The bias may be applied to the data point according to the data point proximity to an actual lumen data point at both a corresponding coordinate position in the A-scan and at least one neighboring scan. In other instances, the weighting function is a maximum gradient, and the maximum gradient eliminates data points in a neighboring frame for use in evaluating an interpolated lumen border data point.

DETAILED DESCRIPTION

The present invention provides a system and method of using an intravascular imaging system to instantly and automatically detect borders within a patient's tissue in response to navigational input. Systems and methods of the invention operate with intravascular imaging systems such as, for example, intravascular ultrasound (IVUS), optical coherence tomography (OCT), combined optical-acoustic imaging, others, or a combination thereof.

Figure 1:
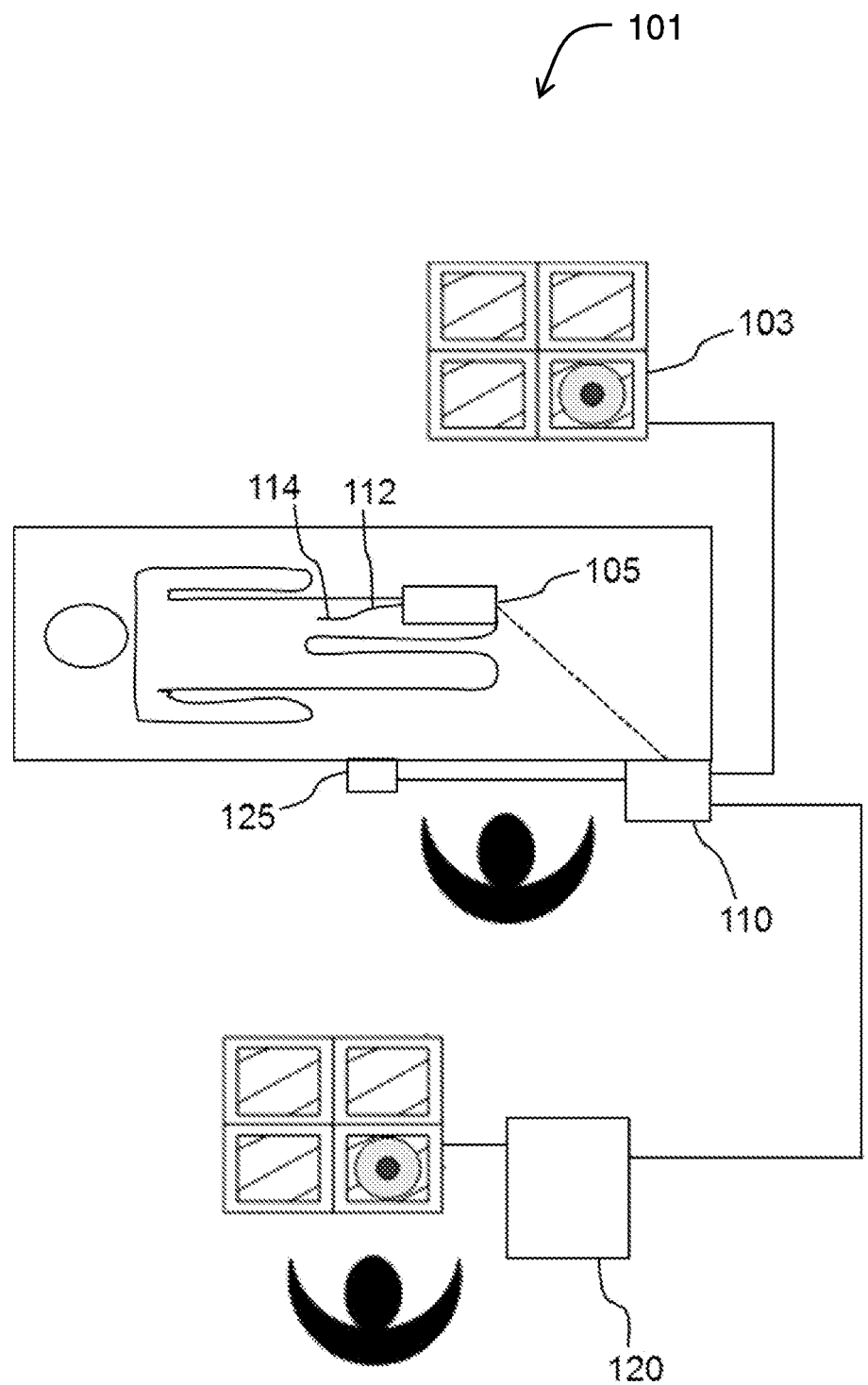
FIG. 1 illustrates an imaging system according to certain embodiments.

FIG. 1 illustrates an exemplary imaging system 101 in accordance with one embodiment of the present invention. System 101 is described for illustrative purposes as an IVUS system. It will be appreciated that detection methods described herein can operate with a 3D data set collected via other imaging modalities as well. System 101 includes console 110 electrically connected to a computing device 120 and a transducer 114 via a catheter 112. The transducer 114 is inserted into a blood vessel of a patient lying etherized upon a table and used to gather IVUS data (i.e., blood-vessel data, or data that can be used to identify the shape of a blood vessel, its density, its composition, etc.). The IVUS data is then provided to (or acquired by) the IVUS console 110, where it is used to produce an IVUS image of the vessel. Systems for IVUS suitable for use with the invention are discussed in U.S. Pat. No. 5,771,895; U.S. Pub. 2009/0284332; U.S. Pub. 2009/0195514; U.S. Pub. 2007/0232933; and U.S. Pub. 2005/0249391, the contents of each of which are hereby incorporated by reference in their entirety.

More particularly, IVUS data is typically gathered in segments, either through a rotating transducer or an array of circumferentially positioned transducers, where each segment represents an angular portion of an IVUS image. Thus, it takes a plurality of segments (or a set of IVUS data) to image an entire cross-section of a vascular object. Furthermore, multiple sets of IVUS data are typically gathered from multiple locations within a vascular object (e.g., by moving the transducer linearly through the vessel). These multiple sets of data can then be used to create a plurality of two-dimensional (2D) images or one three-dimensional (3D) image. It should be appreciated that the present invention is not limited to the use of an IVUS device (or the acquisition of IVUS data), and may further include using thermographic devices, optical devices (e.g., an optical coherence tomography (OCT) console), MRI devices, or any vascular imaging devices generally known to those skilled in the art. For example, instant automatic border detection may be provided in OCT systems such as those described in U.S. Pub. 2011/0152771; U.S. Pub. 2010/0220334; U.S. Pub. 2009/0043191; U.S. Pub. 2008/0291463; and U.S. Pub. 2008/0180683, the contents of each of which are hereby incorporated by reference in their entirety. It should further be appreciated that the computing device depicted in FIG. 1 includes, but is not limited to, personal computers or any other data-processing devices (general purpose or application specific) that are generally known to those skilled in the art.

Figure 2:
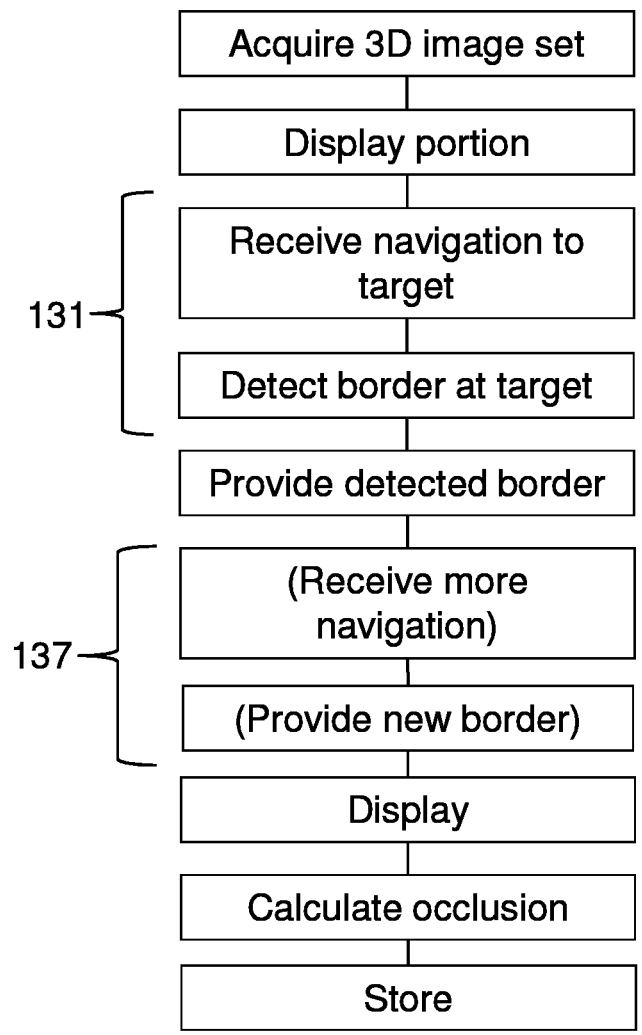
FIG. 2 diagrams steps by which methods of embodiments of the invention operate.

FIG. 2 diagrams steps by which methods of embodiments of the invention operate. After being captured through the use of transducer 114, the IVUS data (or multiple sets thereof) is then provided to (or acquired by) the computing device 120. A portion of the 3D data set is then displayed for the user on, for example, monitor 103. The display will show, in a cross section of a blood vessel, objects within a certain range of transducer 114. Vascular objects include several identifiable borders. For example, the luminal border demarcates the blood-intima interface and the medial border demarcates the external elastic membrane (the boundary between the media and adventitia). As shown in FIG. 2, detecting the luminal border, the medial border, or any other border is coupled to a user's use of a control device 125 to navigate to the target.

At step 131, the system receives a user's navigation to a target area of interest. Navigational input from the user operates to change the display (e.g., as to mimic motion through the tissue until a point is reached at which a user expresses interest by ceasing to navigate). Upon cessation of navigation, the system detects any border within the image that is then presently displayed. The system provides the detected border. The detected border can be provided as one or more lines drawn on the screen (e.g., overlaying the location of the detected border), in the form of a numerical calculation, as a file for later reference, as a diagnostic code, or a combination thereof. As shown in FIG. 2, the system and method can operate iteratively, as optional step 137 can include more navigation by the user causing the system to provide additional border detection. After any optional additional navigation is ceased, the detected border may be provided (again, as a display, a calculation, a file stored in memory, or a combination thereof).

By detecting those borders, the plaque-media complex, which is located there between, can be analyzed and/or calculated. It should be appreciated that the present invention is not limited to the identification of any particular border, and includes all vascular boundaries generally known to those skilled in the art.

Referring back to FIG. 1, the border-detection application is adapted to identify a border on a vascular image (e.g., an IVUS image). In one embodiment of the present invention, this is performed by analyzing the IVUS image, or IVUS data that corresponds the IVUS image, to determine certain gradients located therein. This is because borders of vascular objects can be identified by a change in pixel color (e.g., light-to-dark, dark-to-light, shade1-to-shade2, etc.).

Figure 3:
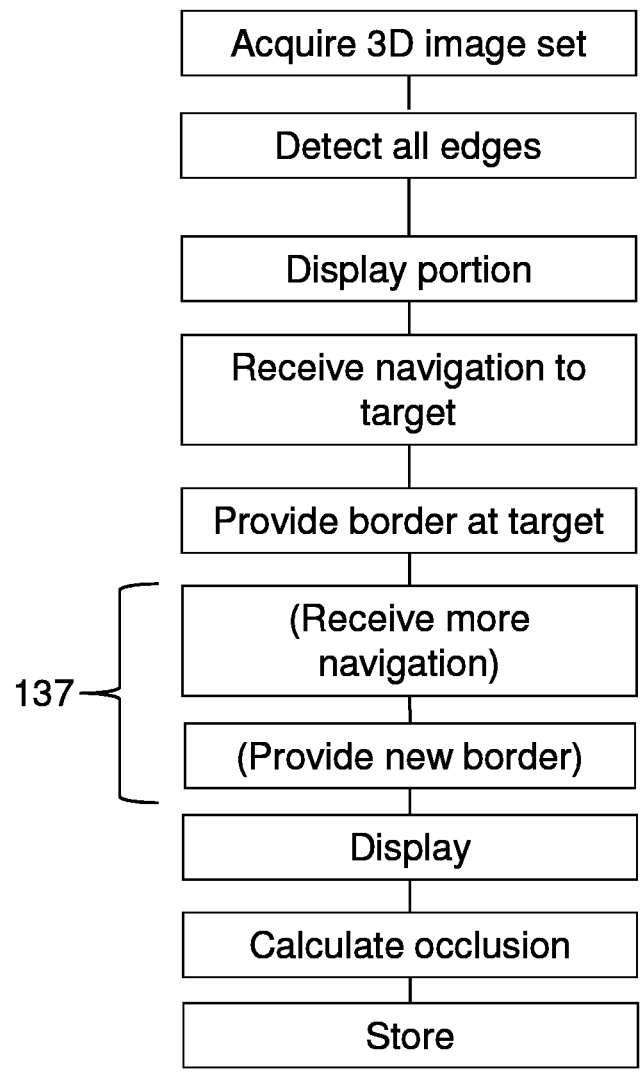
FIG. 3 diagrams an embodiment of the invention.

FIG. 3 shows an alternative embodiment of the invention, particularly suited for imaging systems with good processing power. As depicted here, the incoming IVUS data is processed in its entirety and all candidate borders are detected. The information of the detected borders may be stored in non-transitory memory (e.g., even if it is not used or called). While a processor of the system has detected all of the borders the system has operated to display a portion of the imaged tissue. Navigational input from the user operates to change the display (e.g., as to mimic motion through the tissue until a point is reached at which a user expresses interest by ceasing to navigate). Upon cessation of navigation, the system provides the detected border that was already detected previously. It will be appreciated that the methodology as described in reference to FIG. 3 may be desirable to employ for systems with good processing power available such as, for example, systems that use one or more of a graphics-processing-unit (GPU) such as a video card sold by NVIDIA to detect the border.

Figure 4:
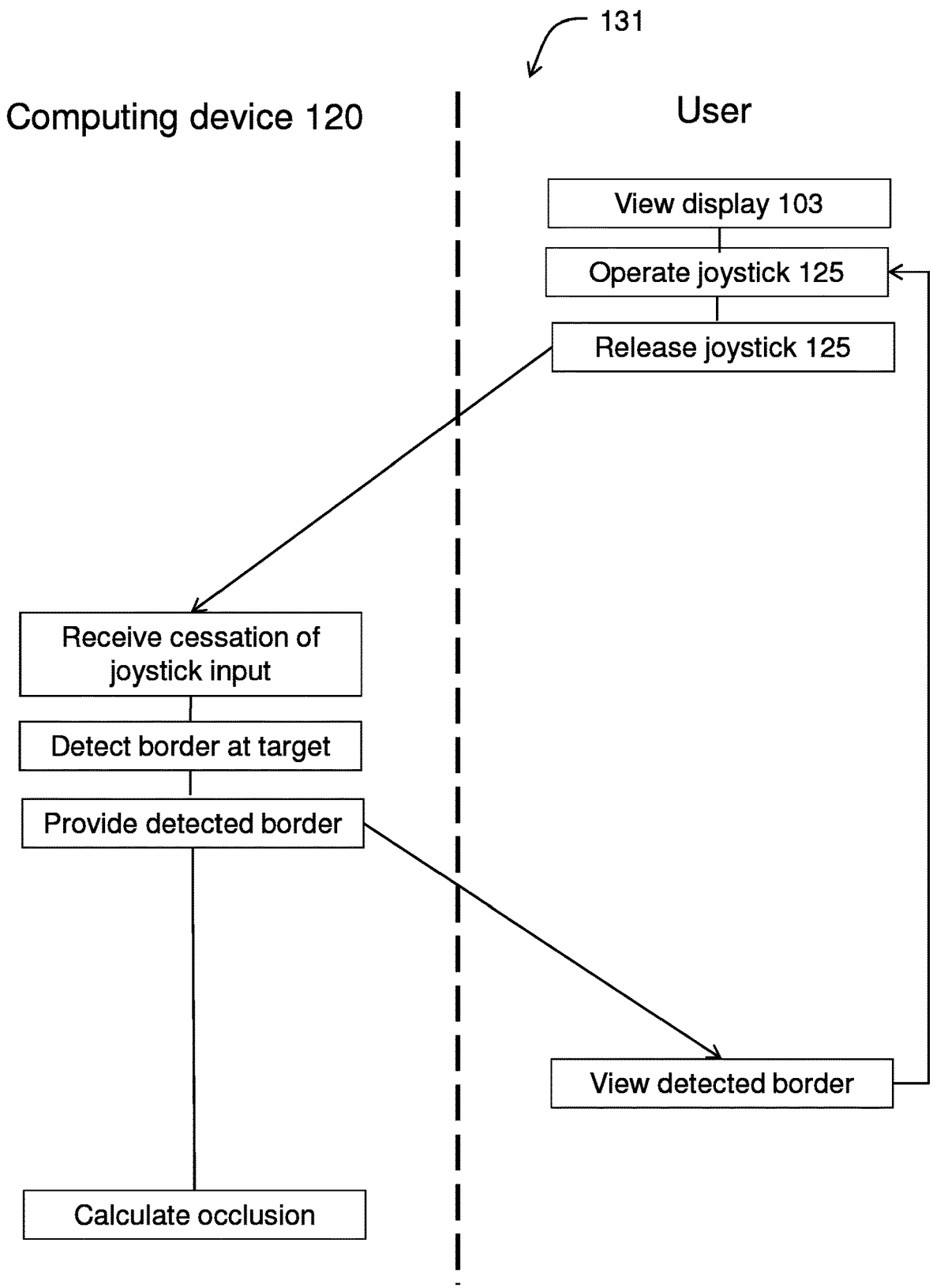
FIG. 4 illustrates coupled interactions between a user and a computing device.

FIG. 4 illustrates with particularity the coupled interactions between a user and a computing device 120 at step 131 from FIG. 2. An operator/user, such as a physician, views the display 103 to see images from a 3D data set. The user uses joystick 125 to navigate through the view to a position of interest. The invention employs the insight that an easy and intuitive human action is to navigate to (e.g., to "go to") something of interest and then to stop going. While prior art systems required additional steps, such as queuing up and operating a separate border detection module, systems of the invention respond to the user's simple cessation of navigation to detect a border in the area where the user stopped—the target area. In some embodiments, the system detects or provides a border responsive to a cessation of navigational input. For example, the prompt can be a release of a mouse button, cessation of scrolling of a mouse wheel, lifting a finger off of a touchscreen after tracing a path, or release of a joystick. The system provides the detected border, which the user can view. Depending on how the systems is set up, the system can even automatically and instantly calculate the occlusion (e.g., using a ratio of luminal border to medial border).

Figure 5:
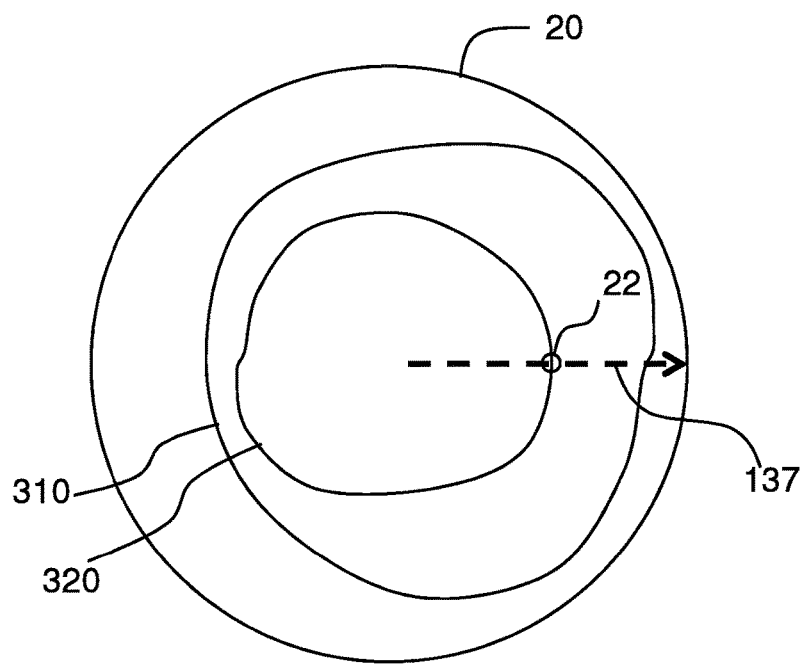
FIG. 5 illustrates a display of an imaging system showing a luminal border.

FIG. 5 illustrates, in simplified fashion, a display 131 of an imaging system showing a luminal border 320 and a medial border 310. In certain embodiments, the system uses a processor to perform an image processing operation to detect a border. A border may be detected instantly, automatically, solely in response to navigational input or cessation of navigational input, or a combination thereof. Automatically generally refers to an absence of human intervention. Where a system automatically provides a border in response to navigational input, that means that no human action other than the navigational input is required. Instant can mean simultaneously, substantially simultaneously, within a few microseconds, within about a second, or within a few seconds. Any suitable border detection algorithm can be employed. Exemplary border detection systems are discussed in U.S. Pat. Nos. 7,463,759; 6,475,149; 6,120,445; U.S. Pub. 2012/0226153; and U.S. Pub. 2007/0201736, the contents of which are incorporated by reference. For example, in some embodiments, the system uses a radius to detect a control point; uses the control point to define a search area; uses the search area to find a portion of a border; and uses the portion of the border to locate an entire border. Looking at FIG. 5, a first control point 22 may be taken as a point of highest contrast on an arbitrary radius 137 from the center of the screen to an edge (e.g., the "due east" radius at a theta of zero). Starting from the control point 22, system then defines an area 25 around point 22.

Figure 6A:
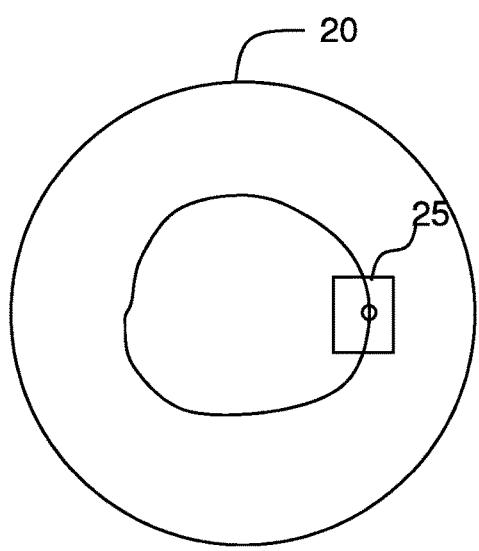
FIG. 6A depicts a defined area around point on a tomographic view.

FIG. 6A depicts a defined area 25 around point 22. Area 25 operates as a search window. The search window area 25 may be a rectangle, circle, ellipse, polygon, or other shape. It may have a predetermined area (e.g., a certain number of pixels). In some embodiments, a size and shape of area 25 is determined by a combination of input device resolution, screen area subtended by a pixel at the particular polar coordinates, current zoom factor, usability studies, or a combination thereof. Usability studies can be performed to establish a statistical model of user repeatability and reproducibility under controlled conditions.

Figure 6B:
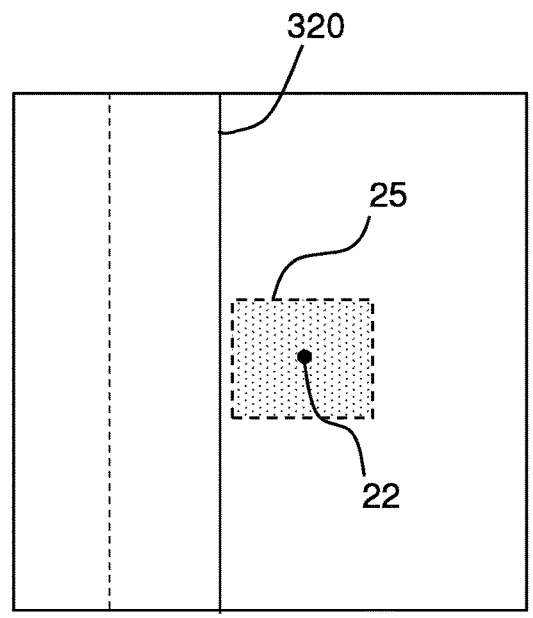
FIG. 6B shows a corresponding B-scan.

FIG. 6B depicts a defined area 25 around point 22 shown in a B scan. The system searches for the border within area 25 by performing a processing operation on the corresponding data. The processing operation can be any suitable search algorithm known in the art. In some embodiments, a morphological image processing operation is used. Morphological image processing includes operations such as erosion, dilation, opening, and closing, as well as combination thereof. In some embodiments, these operations involve converting the image data to binary data giving each pixel a binary value. With pixels within area 25 converted to binary, each pixel of a feature such as a border may be black, and the background pixels will predominantly be white (or vice versa). In erosion, every pixel that is touching background is changed into a background pixel. In dilation, every background pixel that is adjacent to the non-background object pixels is changed into an object pixel. Opening is an erosion followed by a dilation, and closing is a dilation followed by an erosion. Morphological image processing is discussed in Smith, The Scientist and Engineer's Guide to Digital Signal Processing, 1997, California Technical Publishing, San Diego, CA, pp. 436-442.

If a border is not found within area 25, area 25 can be increased and the increased area can be searched. This strategy can exploit the statistical properties of signal-to-noise ratio (SNR) by which the ability to detect an object is proportional to the square root of its area. See Smith, Ibid., pp. 432-436.

With reference to FIG. 6B, once a portion of the border is detected within area 25, the search can then be extended "upwards" and "downwards" into adjacent A-scan lines in the B-scan until the entire border is detected by the processor and its location is determined with precision. In some embodiments, image processing operations incorporate algorithms with pre-set parameters, user-set parameters, or both that optimize results and continuity of results. For example, if a line appears that is not contiguous across an entire 100% of the image (e.g., the entire extent of the B-scan or a full circle in a tomographic view), an accept or reject parameter can be established based on a percent contiguous factor. In some embodiments, lines that are contiguous across less than 75% (or 50% or 90%, depending on applications) are rejected while others are accepted.

While described above as detecting a reference item (e.g., a border) by receiving cessation of navigation followed by using a processor to detect the border, the steps can be performed in other orders. For example, the system can apply morphological processing operations to an entire image and detect every element, or every element that satisfies a certain quality criterion. Then the system can receive the navigation and respond by provided the pre-detected border. Similarly, the steps can be performed simultaneously. Using the methodologies herein, systems of the invention can provide a border detected within an image of an imaging system, such as an IVUS system, with great precision, based on a location that an operator navigates too. As discussed above, any suitable border detection process can be employed. Border detection is described, for example, in U.S. Pat. Nos. 8,050,478; 7,068,852; 6,491,636; U.S. Pub. 2011/0216378; and U.S. Pub. 2003/0016604, the contents of which are incorporated by reference.

FIGS. 7-12 illustrate certain embodiments, in which computing device 120 includes a plurality of applications operating thereon—i.e., a border-detection application, an extrapolation application, and an active-contour application. These applications are used to (i) identify a border and control points on a first IVUS image (i.e., any IVUS image), (ii) extrapolate the control points to a second IVUS image (i.e., another IVUS image), (iii) identify a border on the second IVUS image, and (iv) adjust the border on the second IVUS image. It should be appreciated that the number and/or location of the applications are not intended to limit the present invention, but are merely provided to illustrate the environment in which the present invention operates. Thus, for example, using a single application to perform the application functions, as discussed herein, or remotely locating at least one of the applications (in whole or in part) is within the spirit and scope of the present invention. It should further be appreciated that, while the present invention is discussed in terms of singularities (e.g., identifying a border on one IVUS image, extrapolating control points to another IVUS image, etc.), the present invention is not so limited. In fact, the present invention is particularly useful if it is used on a plurality of IVUS images (e.g., identifying borders on every fifth IVUS image, extrapolating control points from the fifth IVUS image to the next four IVUS images, etc.). It should also be appreciated that the terms "first" and "second," as those terms are used herein, are used broadly to identify any two IVUS images. Thus, the phrase "second IVUS image" may be used to identify an IVUS image distinct from a first IVUS image (as opposed to the second IVUS image in a series of IVUS images).

Figure 7:
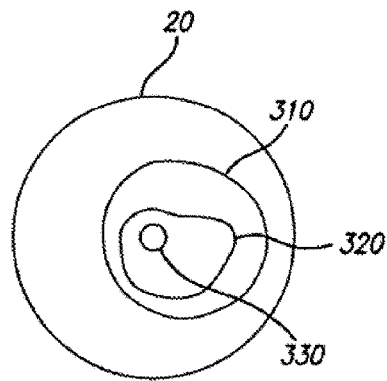
FIG. 7 depicts an exemplary IVUS image of a vascular object.

FIG. 7 shows a cartoon rendering of an exemplary IVUS image 20 of a vascular object. The image 20 is depicted as including a luminal border 320 and a medial border 310. On a typical IVUS grayscale image, starting from the center and working outward, the catheter will be the first light-to-dark transition. Continuing outward, the next dark-to-light transition (or gradient) identifies the luminal border (i.e., see FIG. 7, 320). The medial border can then be identified by going outward from the luminal border until the next dark-to-light transition (or gradient) is found (see FIG. 7, 310). It should be appreciated that because the IVUS image is constructed using gray-scales, it may be necessary to utilize an algorithm and/or at least one threshold value to identify precisely where the image changes from light to dark (or vice versa). However, it should further be appreciated that the present invention is not limited to any particular algorithm for identifying the aforementioned transitions, and includes all algorithms (and/or threshold values) generally known to those skilled in the art.

Figure 8:
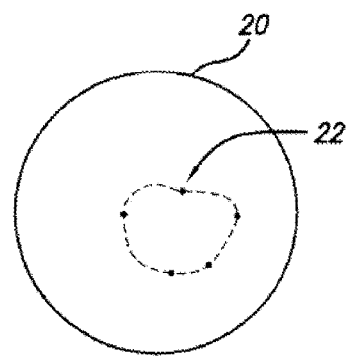
FIG. 8 illustrates a step in use of a border-detection algorithm.

Once the border is identified, the border-detection algorithm is further adapted to identify at least one control point on the border. For example, with reference to FIGS. 7 and 8, the border-detection algorithm can be used to identify a plurality of control points 22 on the luminal border 320. It should be appreciated that the location and number of control points depicted in FIG. 8 are not intended to limit the present invention, and are merely provided to illustrate the environment in which the present invention may operate. In an alternate embodiment, the border-detection application is adapted to identify a border using user-identified control points. Embodiments are described in in U.S. Pat. Nos. 8,233,718; 7,978,916; and 6,381,350, the contents of each of which are incorporated by reference in their entirety.

Figure 9:
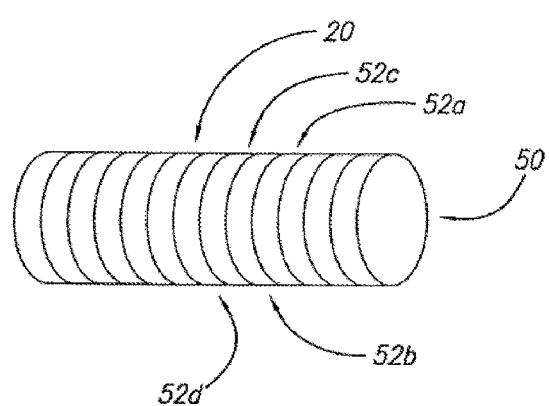
FIG. 9 shows use of multiple 2D images to produce a 3D image of a tubular object.

Referring back to FIG. 1, once the border and control point(s) are identified on a first vascular image, the extrapolation application is used to identify at least one control point on at least one other IVUS image. In a preferred embodiment of the present invention, this is done by extrapolating the previously identified control points to at least one other IVUS image. By doing this, multiple 2D images (or at least one 3D image) can be produced. For example, as illustrated in FIG. 9, multiple 2D images (e.g., 20, 52a-52d, etc.) are used to produce a 3D image of a tubular (e.g., vascular) object 50.

Figure 10:
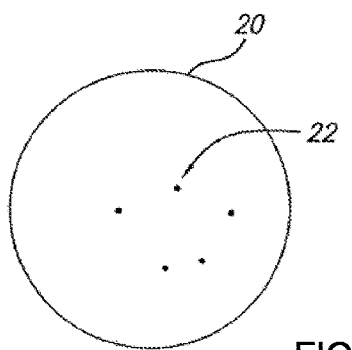
FIG. 10 extrapolation of an identified control point to another IVUS image.

FIG. 10 illustrates how an identified control point can be extrapolated to another IVUS image. Specifically, the control points that were illustrated in FIG. 8 (i.e., 22) are extrapolated (or copied) to another IVUS image (e.g., 52d), thus creating a second set of control points 62. In one embodiment of the present invention, the control points are extrapolated using Cartesian coordinates. It should be appreciated that, while FIG. 10 illustrates control points being extrapolated to an adjacent image, the present invention is not so limited. Thus, extracting control points to additional images (e.g., 52c, 52b, etc.) is within the spirit and scope of the present invention.

Once the control points are extrapolated, the extrapolating application is further adapted to identify (or approximate) a border based on the extrapolated points. For example, as shown in FIG. 10, the extrapolated points 62 may be connected using a plurality of lines 64, where the lines are either straight or curved (not shown). In another embodiment of the present invention, the extrapolating application is adapted to use an algorithm (e.g., a cubic-interpolation algorithm, etc.) to identify line shape.

Referring back to FIG. 1, the active-contour application is then used to adjust the border to more closely match the actual border of the vascular object. In doing so, the active-contour application may consider or take into account at least (i) image gradients (i.e., gradient data), (ii) the proximity of the border to each extrapolated point (i.e., continuity or control-point factor), and/or (iii) border curvature or smoothness (i.e., curvature or boundary factor). Specifically, by considering gradient data (or a gradient factor), the border can be adjusted if the neighboring pixels (as opposed to the pixels of the border) include border characteristics (e.g., a dark-to-light transition, etc.). By considering a continuity or control-point factor, the border can be adjusted so that it passes through each extrapolated point. Furthermore, by considering a curvature or boundary factor, the border can be adjusted to prevent sharp transitions (e.g., corners, etc.). In one embodiment of the present invention, the continuity and curvature factors are also used to connect related borders on adjacent images. It should be appreciated that if multiple factors are being considered, then individual factors may be weighted more heavily than others. This becomes important if the factors produce different results (e.g., the gradient factor suggests adjusting the border away from an extrapolated point, etc.). It should further be appreciated that the active-contour application may also be used to adjust the border identified by the border-detection application. It should also be appreciated that the present invention is not limited to the use of the aforementioned factors for border optimization, and that the use of additional factors (e.g., frequency factor, etc.) to adjust (or optimize) a border is within the spirit and scope of the present invention.

In one embodiment of the present invention, the adjusted borders are configured to be manually manipulated. In other words, at least one point on the border can be selected and manually moved to a new location. The active-contour application is then used (as previously discussed) to reconstruct the border accordingly. In another embodiment of the present invention, the active-contour application is further adapted to adjust related borders in adjacent images. This is done by fitting a geometrical model (e.g., a tensor product B-spline, etc.) over the surface of a plurality of related borders (e.g., as identified on multiple IVUS images). A plurality of points on the geometrical model are then parameterized and formulated into a constrained least-squares system of equations. If a point on the border is manually moved, the active-contour application can utilize these equations to calculate a resulting surface (or mesh of control points). The affected borders (e.g., adjacent borders) can then be adjusted accordingly.

Figure 11:
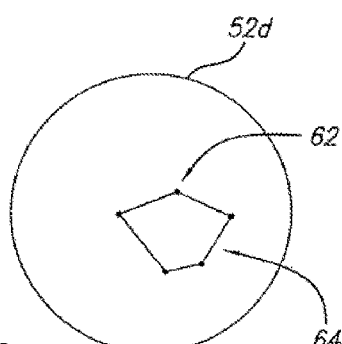
FIG. 11 illustrates a luminal border and a medial-adventitial border.
Figure 11:
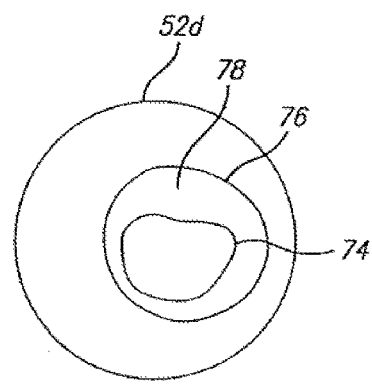

Once the border has been sufficiently adjusted, the aforementioned process can be repeated to identify additional borders. In an alternate embodiment of the present invention, multiple borders (e.g., luminal and medial-adventitial borders) are identified concurrently. The multiple border can then be imaged (in either 2D or 3D) and analyzed by either a skilled practitioner or a computer algorithm. For example, as illustrated in FIG. 11, the luminal border 74 and the medial-adventitial border 76 can be used (by either a clinician or an algorithm) to identify the plaque-media complex 78 of a vascular object.

Figure 12:
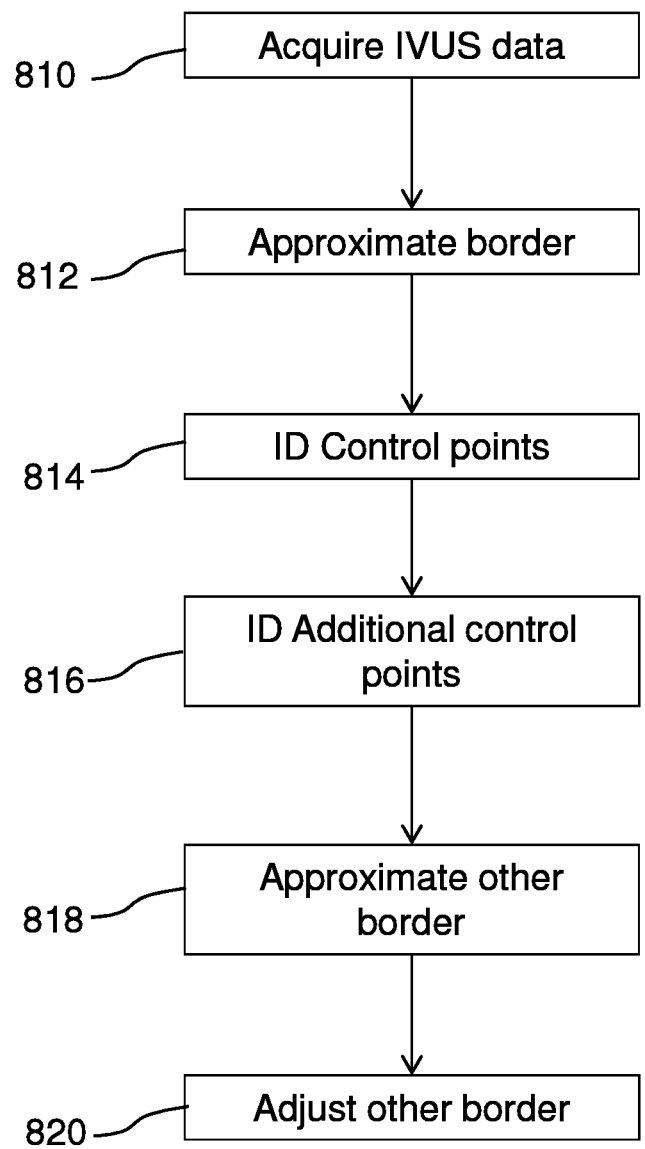
FIG. 12 diagrams a method of identifying a border on a vascular image.

One method of identify a border on a vascular image is illustrated in FIG. 12. Specifically, in step 810, multiple sets of IVUS data are acquired, where each set of IVUS data corresponds to a 2D IVUS image. At step 812, a border is approximated in one IVUS image (e.g., using gradient data, etc.). Control points on the approximated border are then identified at step 814. At step 816, these control points are then used to identify additional control points on additional 2D IVUS images (e.g., via extrapolation, etc.). These additional control points are then used to approximate at least one other border at step 818, which is then adjusted at step 820. In one embodiment, the border is adjusted in accordance with at least gradient data. Other algorithms for border detection are within the scope of the invention and may be employed. Methods of border detection are described in U.S. Pat. Nos. 8,298,147; 8,233,718; 7,831,081; 7,359,554; and 7,215,802, the contents of which are incorporated by reference.

Medical imaging is a general technology class in which sectional and multidimensional anatomic images are constructed from acquired data. The data can be collected from a variety of acquisition systems including, but not limited to, magnetic resonance imaging (MRI), radiography methods including fluoroscopy, x-ray tomography, computed axial tomography and computed tomography, nuclear medicine techniques such as scintigraphy, positron emission tomography and single photon emission computed tomography, photo acoustic imaging ultrasound devices and methods including, but not limited to, intravascular ultrasound spectroscopy (IVUS), ultrasound modulated optical tomography, ultrasound transmission tomography, other tomographic techniques such as electrical capacitance, magnetic induction, functional Mill, optical projection and thermo-acoustic imaging, combinations thereof and combinations with other medical techniques that produce two- and three-dimensional images. At least all of these techniques are contemplated for use with the systems and methods of the present invention.

Images from rotational imaging systems (e.g. OCT and IVUS images) are acquired in the polar domain with coordinates of radius and angle (r, theta) but need to be converted to Cartesian coordinates (x, y) for display or rendering on a computer monitor. Typically, rotational systems consist of an imaging core which rotates and pulls back (or pushes forward) while recording an image video loop. This motion results in a three dimensional dataset of two dimensional image frames, where each frame provides a 360° slice of the vessel at different longitudinal locations.

Although the exemplifications described herein are drawn to the invention as applied to OCT, the systems and methods are applicable to any imaging system.

A particular medical imaging technique contemplated herein is optical coherence tomography (OCT). OCT systems and methods are generally described in Milner et al., U.S. Patent Application Publication No. 2011/0152771, Condit et al., U.S. Patent Application Publication No. 2010/0220334, Castella et al., U.S. Patent Application Publication No. 2009/0043191, Milner et al., U.S. Patent Application Publication No. 2008/0291463, and Kemp, N., U.S. Patent Application Publication No. 2008/0180683, the content of each of which is incorporated by reference in its entirety. OCT is a medical imaging methodology using a specially designed catheter with a miniaturized near infrared light-emitting probe attached to the distal end of the catheter. As an optical signal acquisition and processing method, it captures micrometer-resolution, three-dimensional images from within optical scattering media (e.g., biological tissue). OCT allows the application of interferometric technology to see from inside, for example, blood vessels, visualizing the endothelium (inner wall) of blood vessels in living individuals.

Commercially available optical coherence tomography systems are employed in diverse applications, including art conservation and diagnostic medicine, notably in ophthalmology where it can be used to obtain detailed images from within the retina. Recently it has also begun to be used in interventional cardiology to help diagnose coronary artery disease.

Various lumen of biological structures may be imaged with aforementioned imaging technologies in addition to blood vessels, including, but not limited, to vasculature of the lymphatic and nervous systems, various structures of the gastrointestinal tract including lumen of the small intestine, large intestine, stomach, esophagus, colon, pancreatic duct, bile duct, hepatic duct, lumen of the reproductive tract including the vas deferens, vagina, uterus and fallopian tubes, structures of the urinary tract including urinary collecting ducts, renal tubules, ureter, and bladder, and structures of the head and neck and pulmonary system including sinuses, parotid, trachea, bronchi, and lungs.

The arteries of the heart are particularly useful to examine with imaging devices such as OCT. OCT imaging of the coronary arteries can determine the amount of plaque built up at any particular point in the coronary artery. The accumulation of plaque within the artery wall over decades is the setup for vulnerable plaque which, in turn, leads to heart attack and stenosis (narrowing) of the artery. OCT is useful in determining both plaque volume within the wall of the artery and/or the degree of stenosis of the artery lumen. It can be especially useful in situations in which angiographic imaging is considered unreliable, such as for the lumen of ostial lesions or where angiographic images do not visualize lumen segments adequately. Example regions include those with multiple overlapping arterial segments. It is also used to assess the effects of treatments of stenosis such as with hydraulic angioplasty expansion of the artery, with or without stents, and the results of medical therapy over time.

Figure 13:
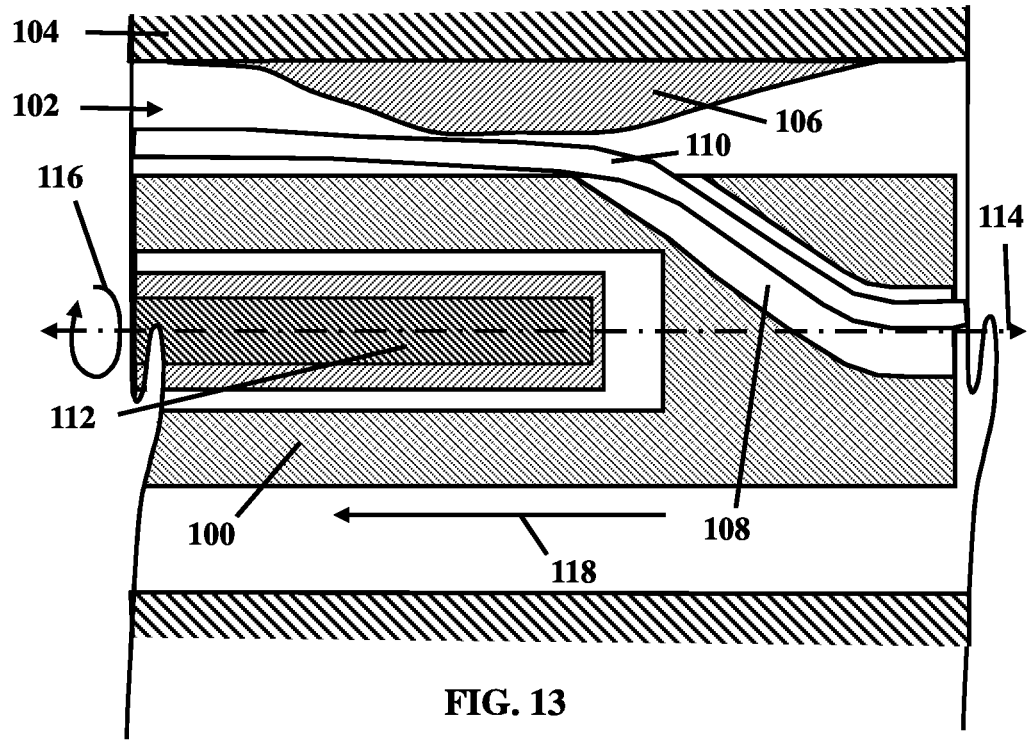
FIG. 13 illustrates a partial cross-sectional view of an imaging catheter suitable for use with a rotational imaging system.

FIG. 13 illustrates an exemplary catheter 100 for rotational imaging inside a lumen of any anatomical or mechanical conduit, vessel, or tube. The exemplary catheter 100 is suitable for in vivo imaging, particularly for imaging of an anatomical lumen or passageway, such as a cardiovascular, neurovascular, gastrointestinal, genitor-urinary tract, or other anatomical luminal structure. For example, FIG. 13 illustrates a vascular lumen 102 within a vessel 104 including a plaque buildup 106. The exemplary catheter 100 may include a rapid access lumen 108 suitable for guiding the catheter 100 over a guide-wire 110.

The exemplary catheter 100 is disposed over an exemplary rotational imaging modality 112 that rotates about a longitudinal axis 114 thereof as indicated by arrow 116. The exemplary rotational imaging modality 112 may comprise, in one embodiment, an OCT system. OCT is an optical interferometric technique for imaging subsurface tissue structure with micrometer-scale resolution. In another embodiment, the exemplary rotational imaging modality 112 may comprise an ultrasound imaging modality, such as an IVUS system, either alone or in combination with an OCT imaging system. The OCT system may include a tunable laser or broadband light source or multiple tunable laser sources with corresponding detectors, and may be a spectrometer based OCT system or a Fourier Domain OCT system, as disclosed in U.S. Patent Application Publication No. 2009/0046295, herein incorporated by reference. The exemplary catheter 100 may be integrated with IVUS by an OCT-IVUS system for concurrent imaging, as described in, for example, Castella et al. U.S. Patent Application Publication No. 2009/0043191 and Dick et al. U.S. Patent Application Publication No. 2009/0018393, both incorporated by reference in their entirety herein.

Figure 14:
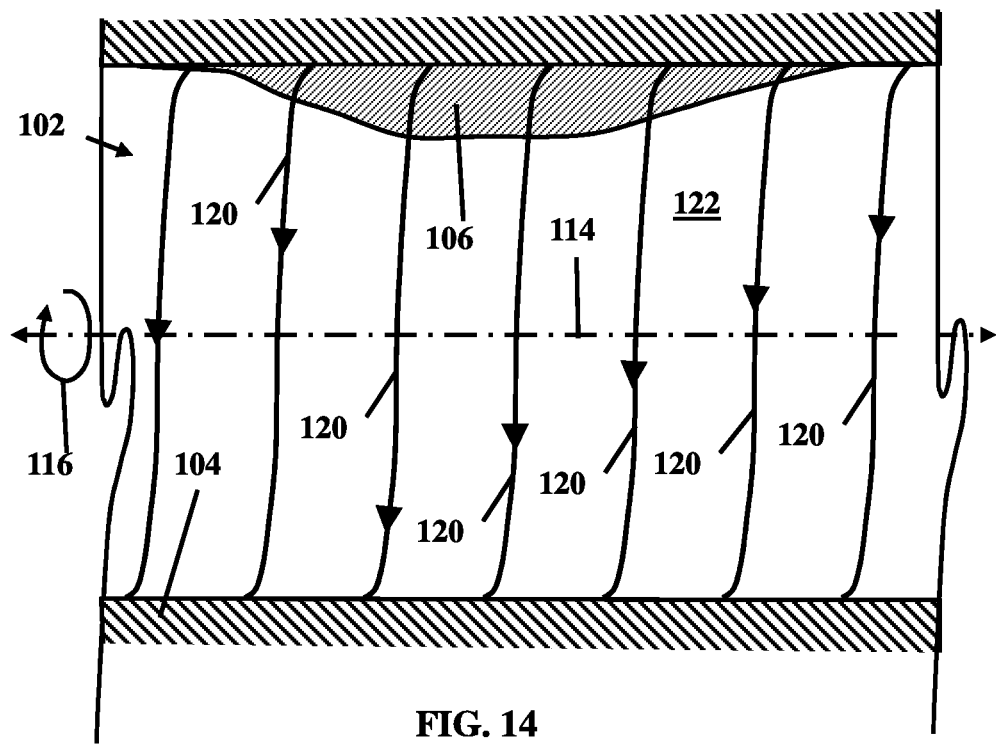
FIG. 14 illustrates a helical scanning pattern for a rotational imaging system.

Referring to FIGS. 13 and 14, the rotational imaging modality 112 may be longitudinally translated during rotation, as indicated by line 118 in FIG. 13. Thus, the rotational imaging modality 112 acquires data along a path 120 that includes a combination of rotation and/or longitudinal translation of the rotational imaging modality 112. FIG. 14 illustrates an exemplary path 120, which is a helical scanning pattern 120, resulting from such a combination. Because FIG. 14 is a cross-sectional view, the helical scanning pattern 120 is illustrated as would be traced on a rear half of a luminal surface 122 of the scanned vessel 104. The helical scanning pattern 120 facilitates scanning a three-dimensional space within and beneath the luminal surface 122 longitudinally as desired, but also introduces a data artifact commonly known as a seam line artifact during reconstruction of the data into a display frame, as will be further discussed herein below.

Referring to FIGS. 13 and 14, the longitudinal axis 114 is illustrated as linear for simplicity and clarity. However, the longitudinal axis 114 is not necessarily linear as illustrated. The longitudinal axis 114 may be curvilinear having a curvature following a tortuosity of the vessel 104. It will be understood that vessel 104 need not be linear, but may in fact have a curvilinear longitudinal axis 104 following the vessel 104 along a tortuous geometry, and that the present invention equally applicable to an imaging modality 112 longitudinally translated along the vessel 104 having a longitudinally linear and/or tortuous geometry.

Figure 15:
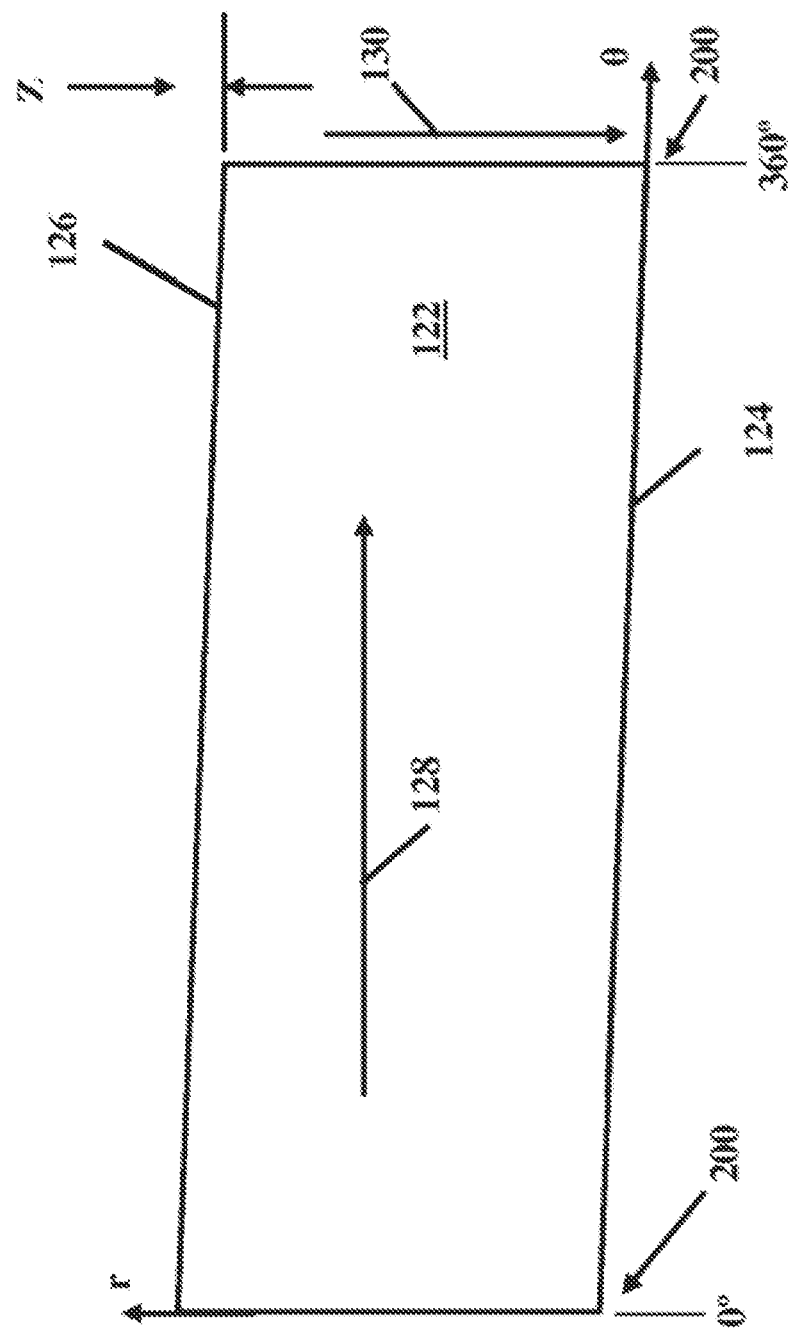
FIG. 15 illustrates the geometry of a data stream acquired using the helical scanning pattern of FIG. 2.
Figure 16:
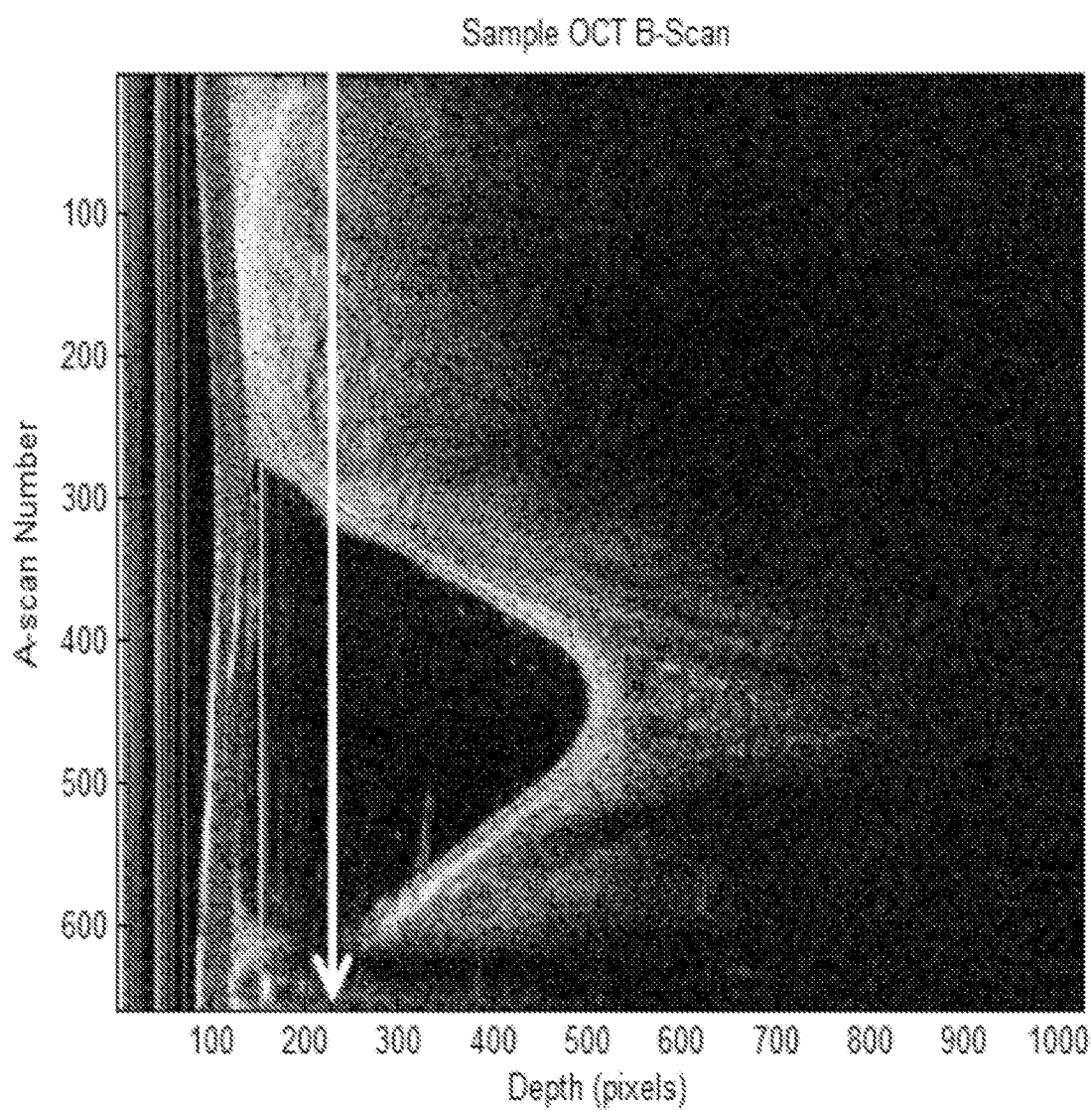
FIG. 16 shows a photograph of a sample OCT B-Scan.
Figure 17:
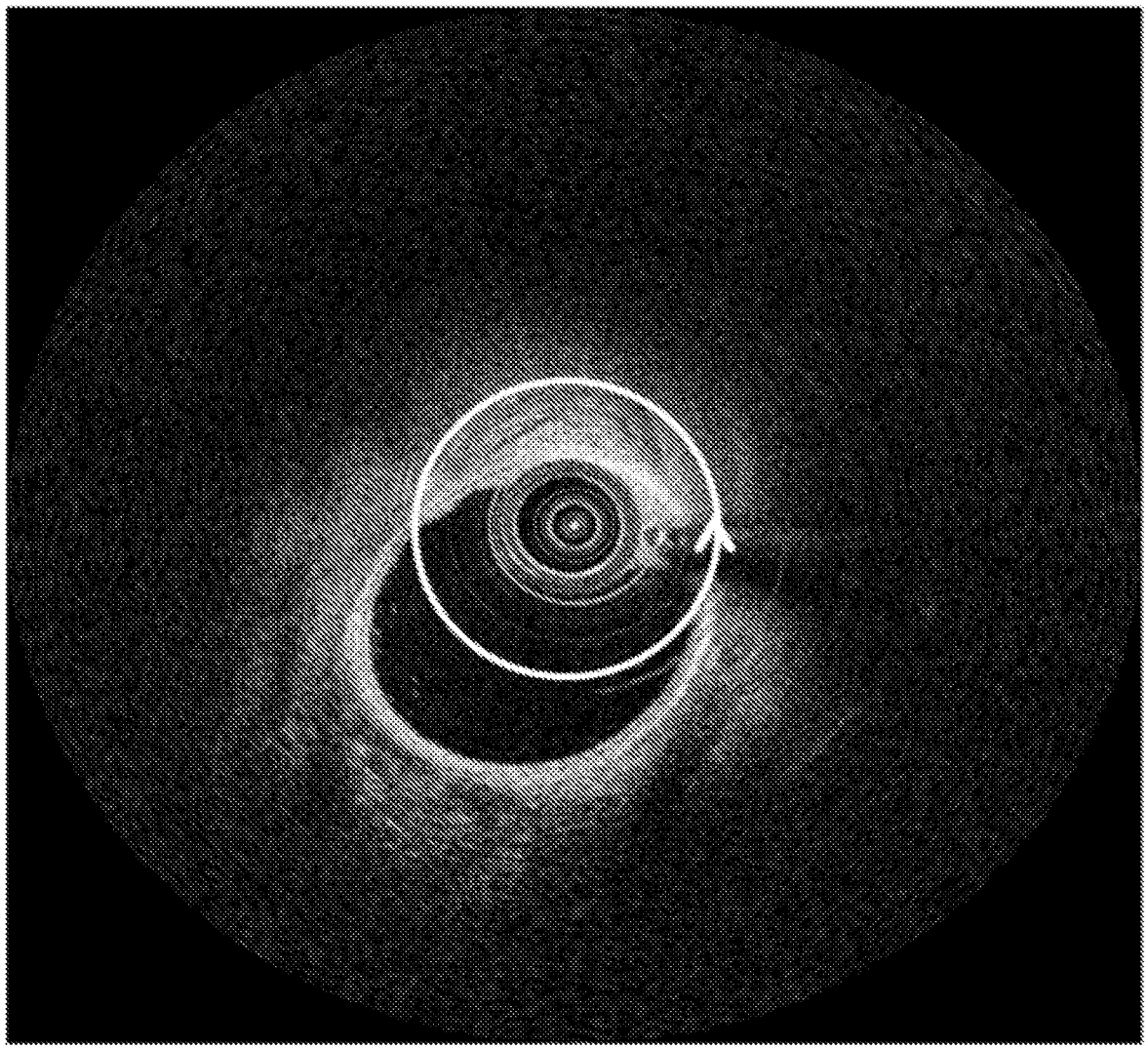
FIG. 17 shows a tomographic OCT image.

Referring to FIG. 15, a portion of the three dimensional space within and beneath the luminal surface 122 scanned within a single rotational period is projected into a planar (two-dimensional) format. In this format, line 126 represents a circumferential axis plotted horizontally. The geometry of a data stream acquired utilizing the above-described helical scan pattern 120 relative to the geometry of the luminal surface 122 may be represented by the parallelogram 124 disposed over the horizontal line 126 in FIG. 15. Starting at a fixed data acquisition angle 200 (hereinafter a "FDAA 200") conveniently denoted as zero degrees (0°) in FIG. 15, the rotational imaging modality 112 acquires data following a rotational path indicated by line 128 (parallel to the line 126) in FIG. 15. However, because the rotational imaging modality 112 may also be translated longitudinally, as indicated by line 130 in FIG. 15, the two-dimensional representation of the scanned three-dimensional space within and beneath the luminal surface 122 comprises the shape of the parallelogram 124. This means that at the end of one full rotation of the rotational imaging modality 112 as denoted in FIG. 15 by the FDAA 200 having a value of 360°, the rotational imaging modality 112 has translated longitudinally by a distance Z. Shown in FIG. 16 is an example of an OCT polar coordinate B-Scan with 660 A-scans. The corresponding scan-converted image is displayed in FIG. 17.

The systems and methods of the invention are for identifying the lumen border in the polar coordinate system of an OCT acquired data set using the signal from each A-scan to form the border. Once the border is identified, it can then be easily transformed to Cartesian coordinates and displayed as a tomographic image. These frames provide a clinician with valuable topological data of the vasculature lumen being examined, for example the severity of stenosis and changes in disease state over time, image data which ultimately aids in accurately assessing a condition for an appropriate clinical treatment plan.

Figure 18:
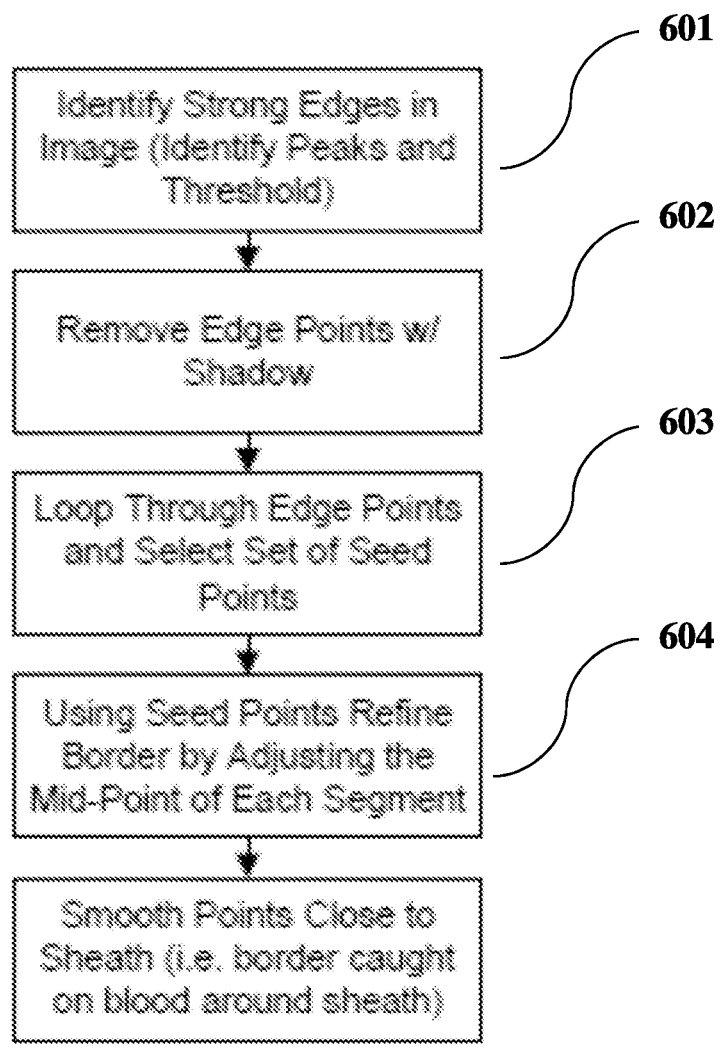
FIG. 18 illustrates five procedural steps of lumen border calculation.

The automatic border detection systems and methods may be broken down into five main procedures or steps corresponding to the five blocks as shown in FIG. 18 and described herein. Block 600 is for the identification of strong or robust edges in the images directly detected with the imaging device. Block 601 is for the evaluation of edge points within a shadow caused by, for example, stent or guide-wires attenuating the OCT light source from properly reaching a strong or robust edge. Block 602 is for the cycling through remaining edge points and selecting one or more sets of seed points that most closely match the position of the starting data points. Block 603 is for the identification of seed points used to define a midpoint, which itself is used to refine the calculated lumen border. Block 604 is for identifying data artifacts arising from blood being caught on or near the imaging device to be evaluated and removed. The five procedural blocks are discussed in more detail as follows.

Referring to FIG. 18, block 600 is for the identification of strong or robust edges in the images directly detected with the imaging device. An important early step in the process of generating two and three dimensional images of lumen of biological structures is the automatic determination of lumen borders or edges. Since the lumen border typically appears as a strong edge in the OCT image, this step may be accomplished using standard image processing edge detection methods.

One technique contemplated for lumen border detection is through the use of an edge detector. Edge detector algorithms are commonly applied to image processing, with variations and applications familiar to those in with skill the art. These algorithms are notably specific to areas of high-resolution image feature processing that identifies regions of an image in which the image brightness changes sharply or has discontinuities. Such an edge detector algorithm can result in an interrupted or uninterrupted curve or line indicating the boundary or edge of a structure. In other situations, the edge detector may be used to identify structural artifacts while preserving the important structural features of an image. Examples of edge detectors useful for the present invention include a Sobel detector, Scharr detector, Prewitt detector, or Roberts-cross operator, Magic Kernal unsampling operator, a simple differencing algorithm, or Canny edge detectors, and any variants thereof, all utilizing smoothing filters such as, for example, exponential or Gaussian filters.

Figure 19:
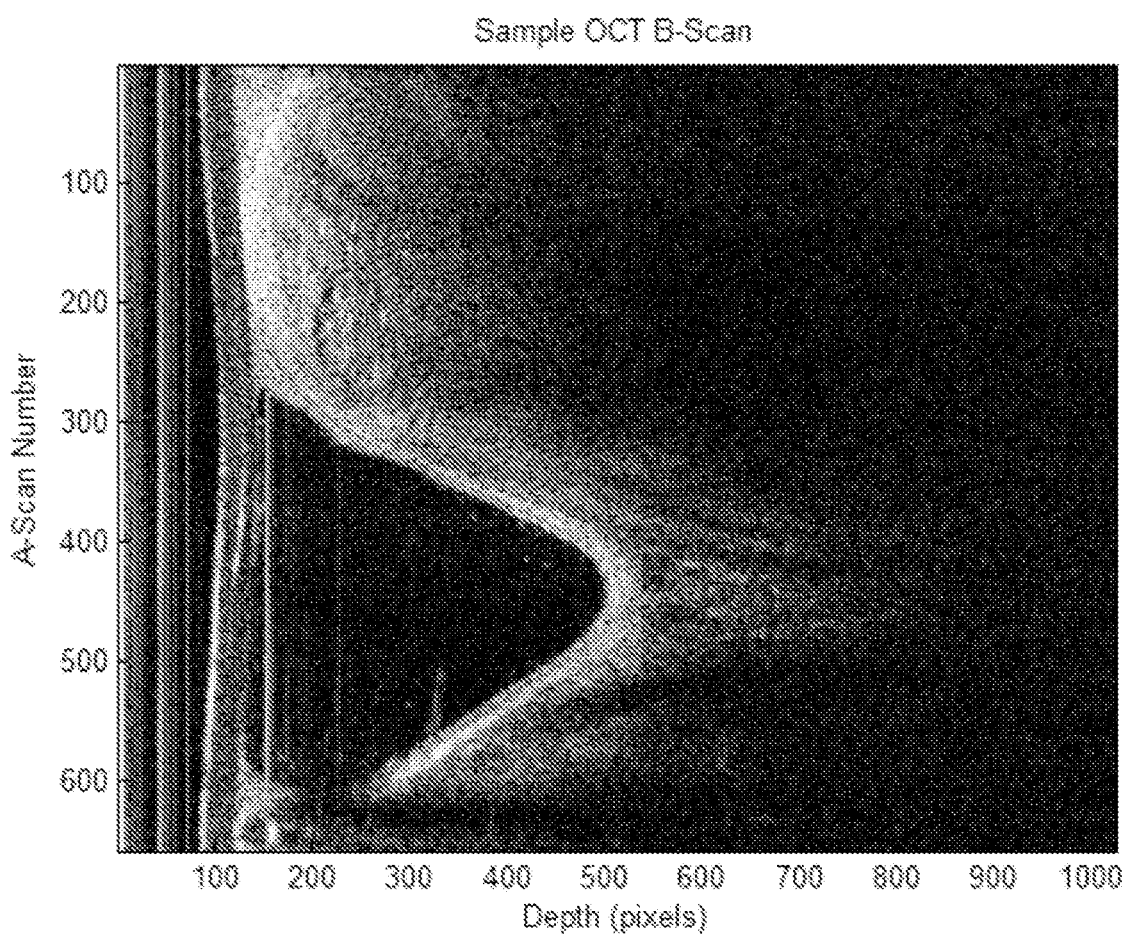
FIG. 19 shows an OCT B-scan from a pig vessel.
Figure 20:
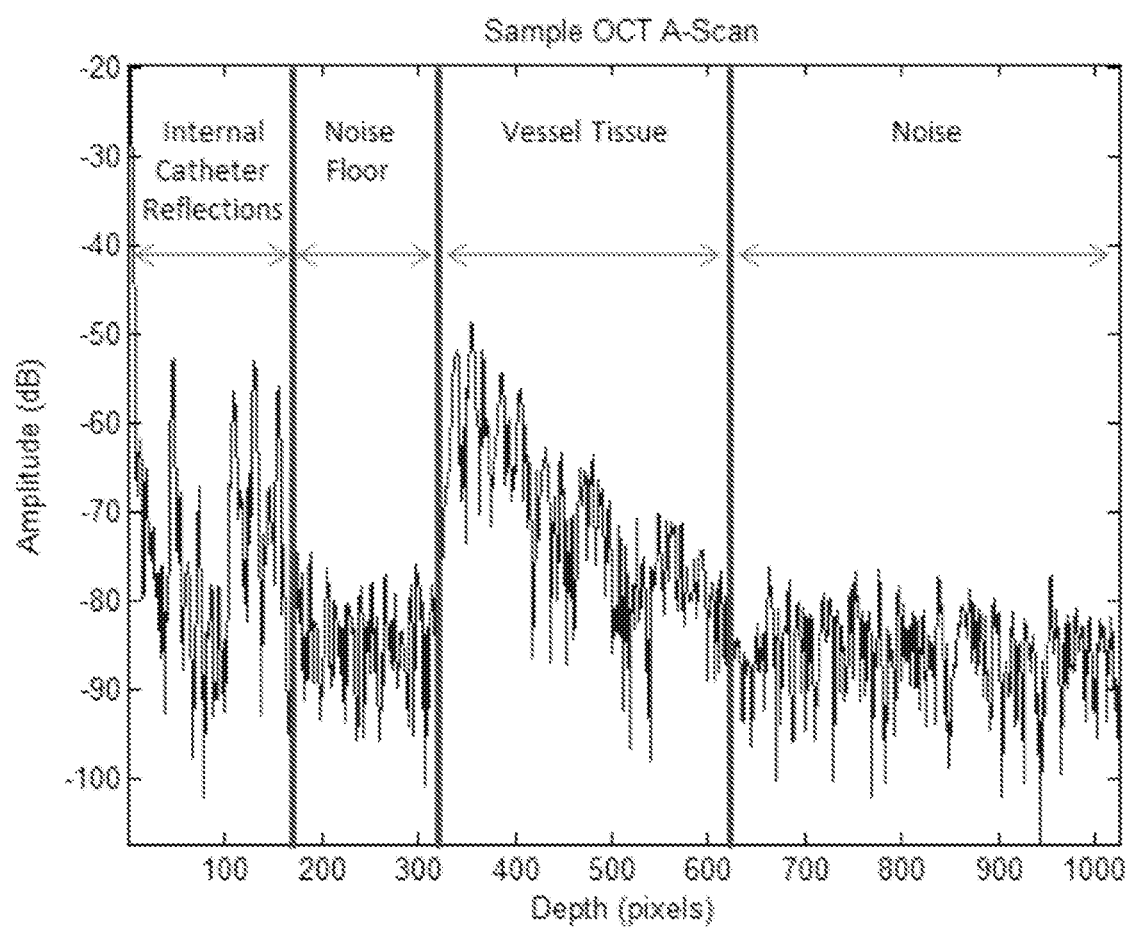
FIG. 20 shows an A-scan.

The typical intensity profile of an A-scan of a vessel usually includes a low amplitude signal (noise) followed by a high amplitude signal at or near the vessel lumen. The OCT light wavelength often is capable of penetrating into the vessel wall and therefore a high amplitude signal due to the vessel appears at or near the actual vessel lumen. The uncertainty in the image data corresponding to the lumen border is due to optical depth penetration as the amplitude of reflected light slowly drops off and returns to the noise floor. These OCT data properties are illustrated in FIGS. 19 and 20, which shows a sample B-scan of a pig vessel (FIG. 19), and an A-scan data line (FIG. 20) corresponding to an A-scan number of FIG. 19. The transition areas of high amplitude signal, noise signal and intermediate signal can be identified in FIG. 20.

Figure 21:
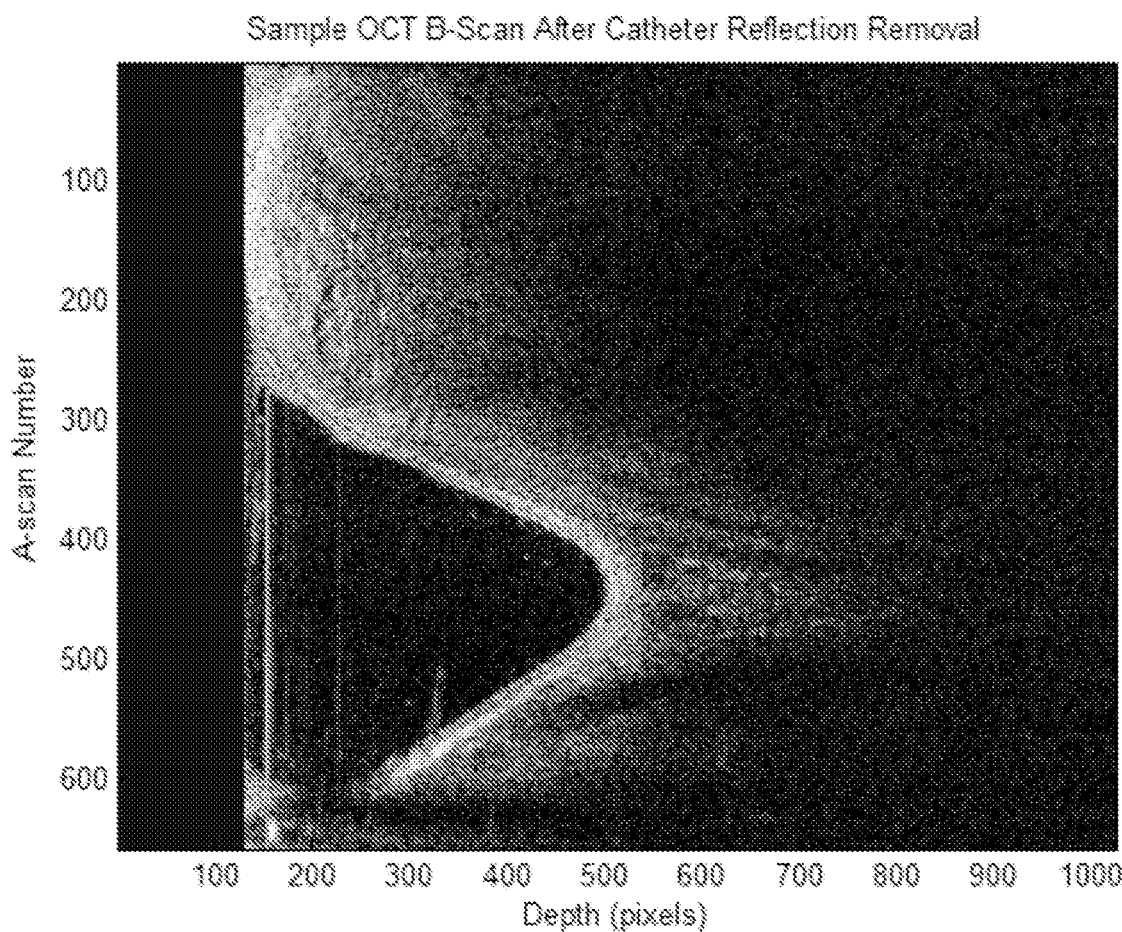
FIG. 21 shows a B-scan after the data points for the internal catheter reflections are set to the noise floor, thereby minimizing the catheter image.

Prior to computing the edge image for edge detection, data corresponding to internal reflections from the catheter region (arising from a fiber optic cable, mirror, sheath, or other internal components of the imaging device) and present in the B-scan can be removed, for example, by setting the pixel intensity amplitude inside the outer diameter of the sheath equal to the noise floor. Removal of the internal catheter reflections allows the prevention of image data signals from interfering with an edge detection procedure for the determination of the vessel lumen. The image data amplitudes corresponding to the outer diameter of the sheath can then be identified by calibration locations (manual or automatic calibration positions). Shown in FIG. 21 is the B-scan of FIG. 19 in which the internal catheter amplitude reflections are set equal to the noise floor, attenuating the catheter data signal.

Figure 22:
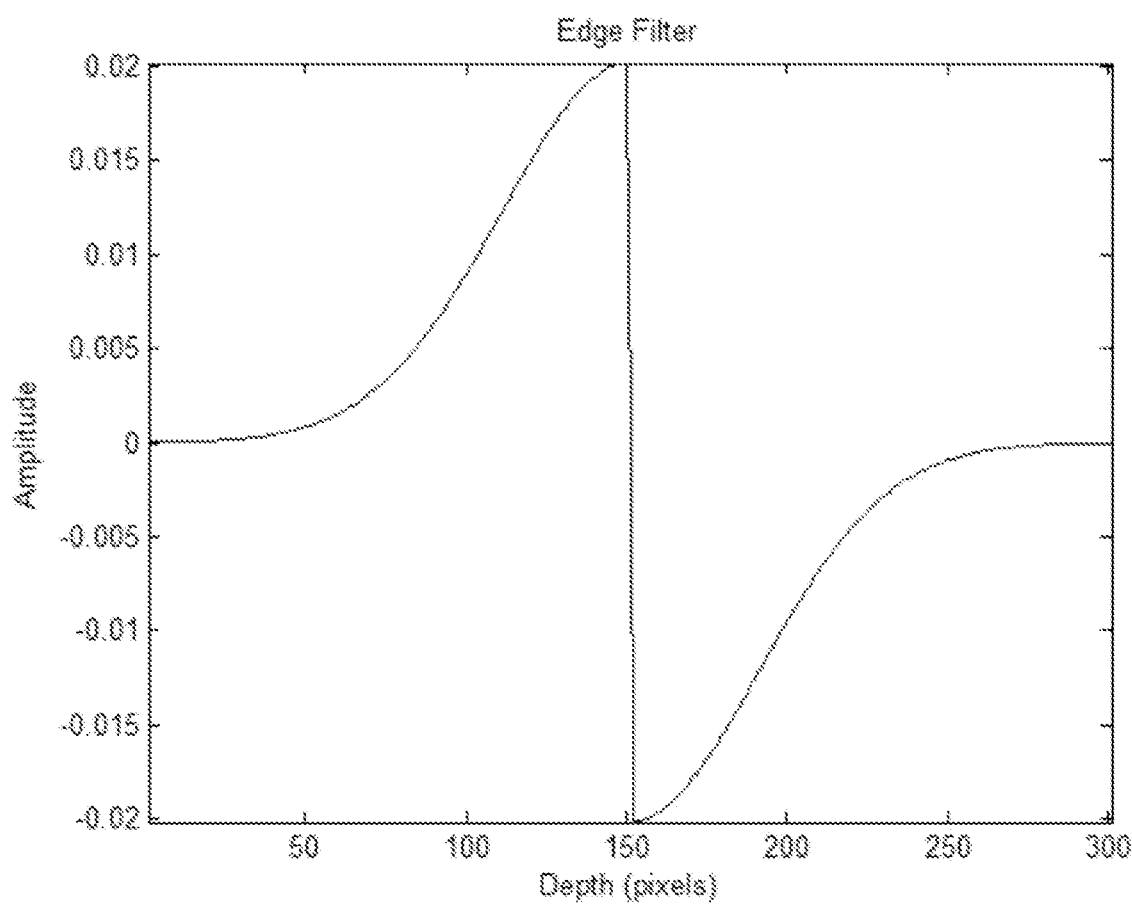
FIG. 22 shows a graph of an edge filter used to identify strong images in a B-scan.
Figure 23:
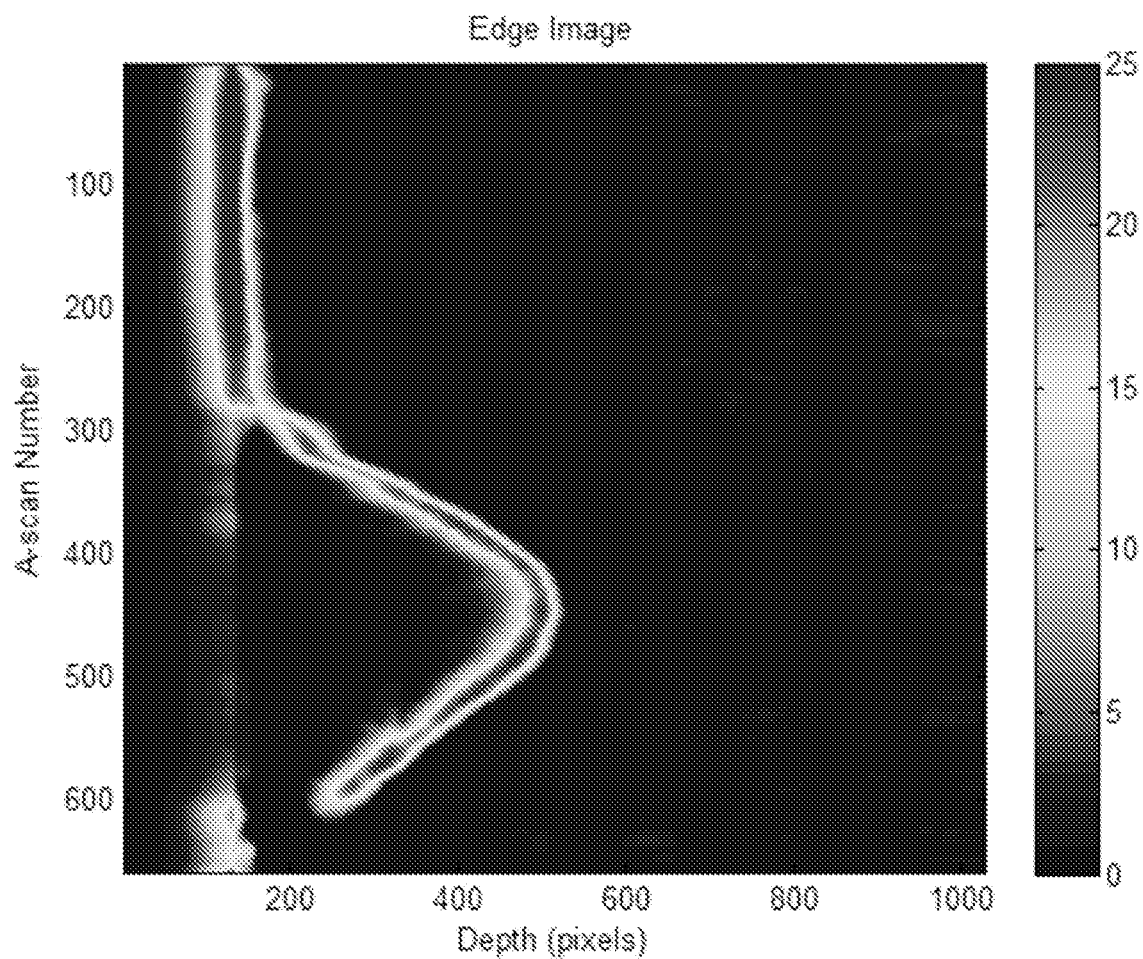
FIG. 23 shows an edge image from convolving a B-Scan with an edge filter.

As described herein, it is contemplated that any of a variety of image processing algorithms (e.g., a Sobel operator, Canny edge detector, or a simple differencing algorithm) are utilized in the identification of edges in an image. Since the vessel lumen typically appears to have some width due to the penetration of light into the vessel lumen epithelial cell layer, a wide gradient operator can be utilized with the edge detector algorithm to identify vessel lumen edges in the image. By using a wide edge detection filter, edges caused by noise spikes or image artifacts may be suppressed. In FIG. 22 shows a graph of one such edge filter which can be convolved with a B-scan to identify strong edges in an acquired image. The filter in FIG. 22 is shaped such that the amplitude of the signal closest to the center will have a higher impact on the edge calculation. Data points further from the center data point corresponding to the highest amplitude lumen border signal are preferred to contribute less to the overall calculation used in the algorithm, and the bias to the edge calculation preferentially drops off. This approach may result in a stronger edge whenever the image data signal is low amplitude for some depth (based on the filter) followed by high amplitude signal for the same depth, i.e., signals that follow the same general (reversed) shape as the filter are likely to have the highest amplitude contributing to the edge point border determination. In FIG. 23 is shown an example of a resulting edge image from convolving the filter shown in FIG. 22 with a B-scan.

Noise spikes in the image data set can result in low amplitude edge points due to the mismatch in the shape of the noise (i.e., the impulse) and the shape, including the width, of the edge filter. In certain embodiments, the width of the filter may be altered (e.g. a priori guidance from the user) for a preferred weight to be applied to the image data based the expected tissue characteristics. In another embodiment, different weights can be applied depending on the particular imaging systems/configurations (e.g. different light wavelengths may yield data needing different weighting). A sample edge image is provided in FIG. 23, where the x-axis corresponds to the pixel depth, the y-axis corresponds to A-scan number and the shading corresponds to the edge strength. Therefore, it is contemplated that the size and shape of a filter used in conjunction with an edge detector algorithm may vary, and is not limited to these examples in the present invention.

In other certain embodiments of the invention, signal amplitude thresholds can be applied to the edge image to identify a set of edge points for further processing. Once the edge image has been computed, peaks along each A-scan can be identified. For each A-scan, two peaks often are identified and are herein cumulatively referred to as edge points. Under nominal vessel imaging conditions, a first peak is the location of the vessel lumen. However, when blood or vessel side-branches are present, the first peak may not be the vessel lumen. A first peak often is the maximum pixel in each A-scan in the edge image, and a second peak is often the next highest peak that is at least some predefined number of pixels, $d_{mins}$, away from the first peak. Setting the next highest peak at a pre-determined distance away from the first peak can be done to avoid having two detections from the same edge location (i.e. neighboring pixel locations). In one embodiment, the edge points and corresponding edge amplitudes are referred to as $P_n$ and $E_n$ as described in Equation 1 below.

$$P_n(a,1) = m_{location}(1) \quad \text{Equation 1a:}$$

$$P_n(a,2) = m_{location}(2) \quad \text{Equation 1b:}$$

$$E_n(a,1) = m_{amplitude}(1) \quad \text{Equation 1c:}$$

$$E_n(a,2) = m_{amplitude}(2) \quad \text{Equation 1d:}$$

where "a" is the a-scan number, "n" is the frame number, "$m_{amplitude}(1)$" is the amplitude of the maximum edge for a-scan a, "$m_{location}(1)$" is the pixel location of $m_{amplitude}(1)$, "$m_{amplitude}(2)$" is the amplitude of the pixel with the maximum edge amplitude for a-scan "a" and is a minimum distance $d_{min}$ from the first peak, and "$m_{location}(2)$" is the pixel location of $m_{amplitude}(2)$. Once the initial set of edge points have been identified, a threshold ($E_{min}$) is applied to remove any points below a pre-determined value.

Figure 24:
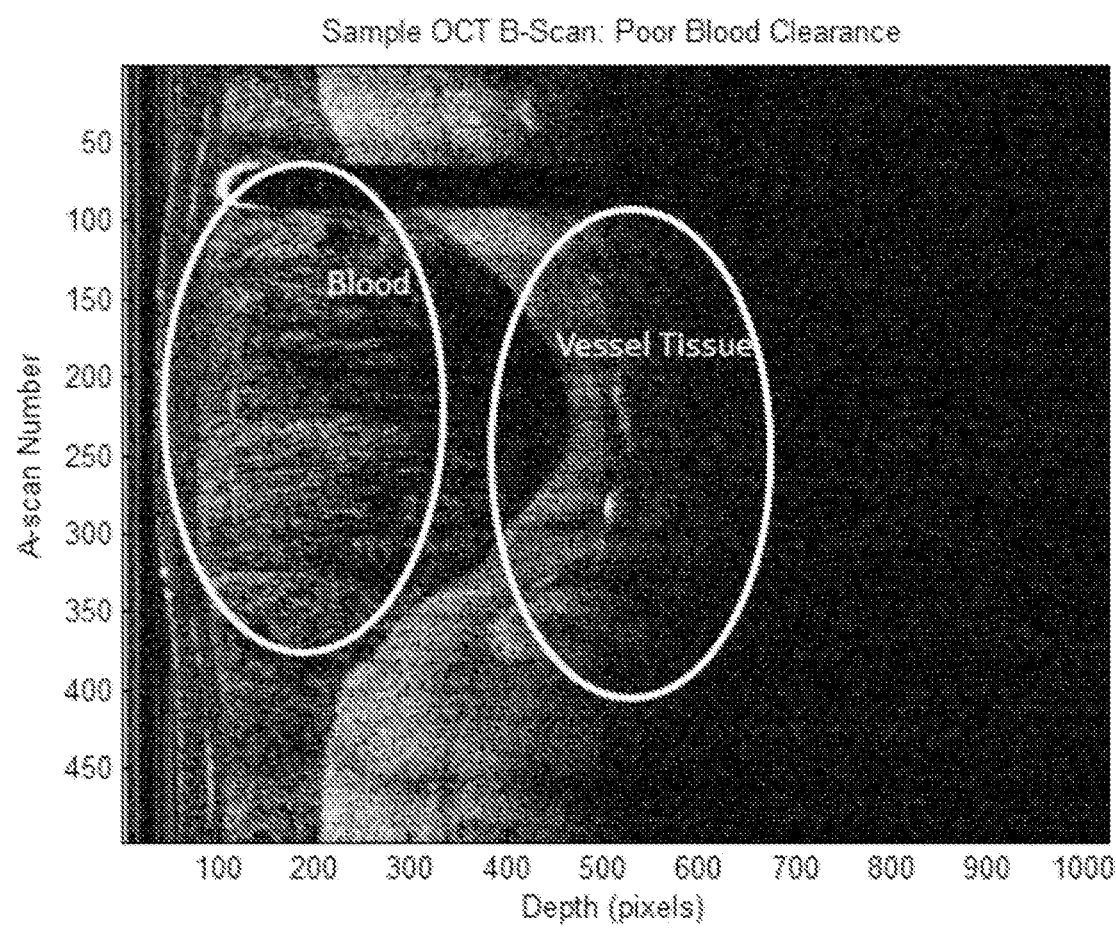
FIG. 24 illustrates an example of a B-Scan with the vessel having poor blood clearance.
Figure 25:
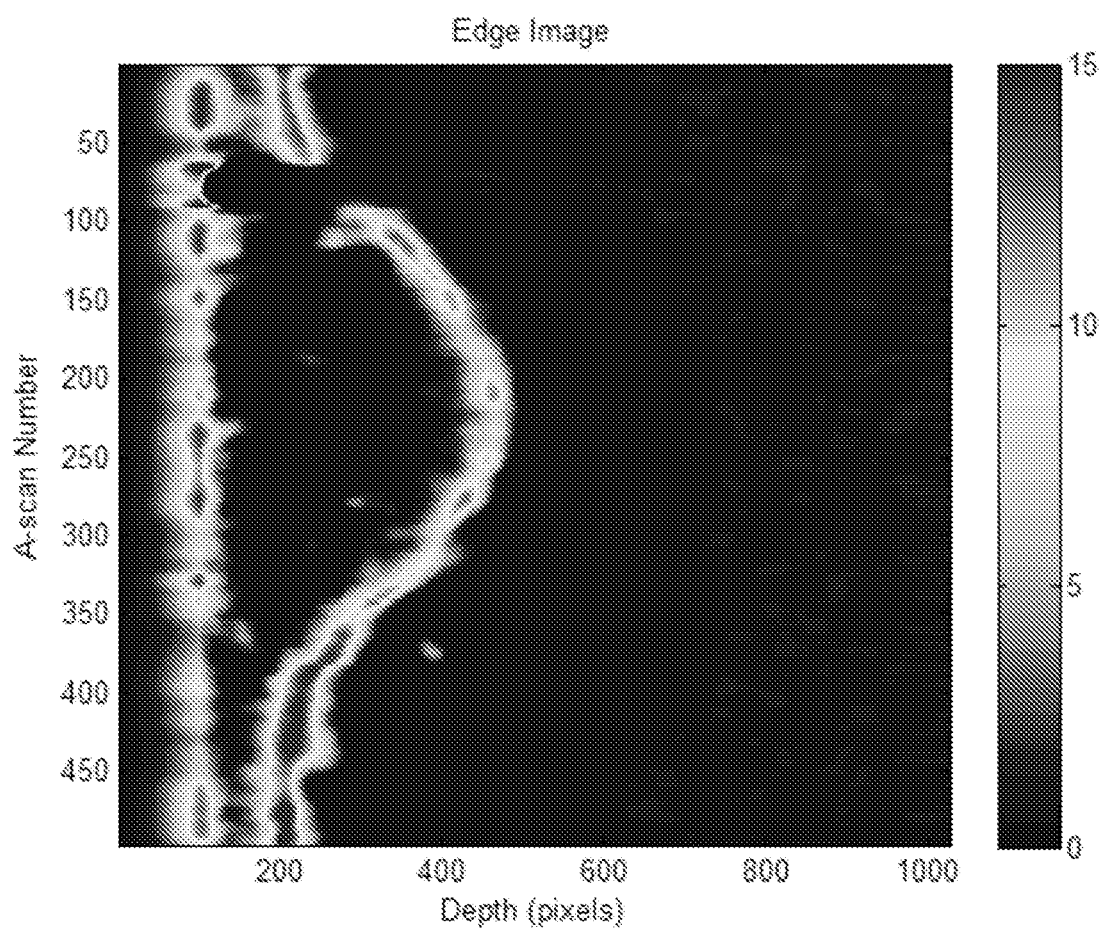
FIG. 25 illustrates an edge image having poor blood clearance that results in a strong sheath signal and weak edge signal.
Figure 26:
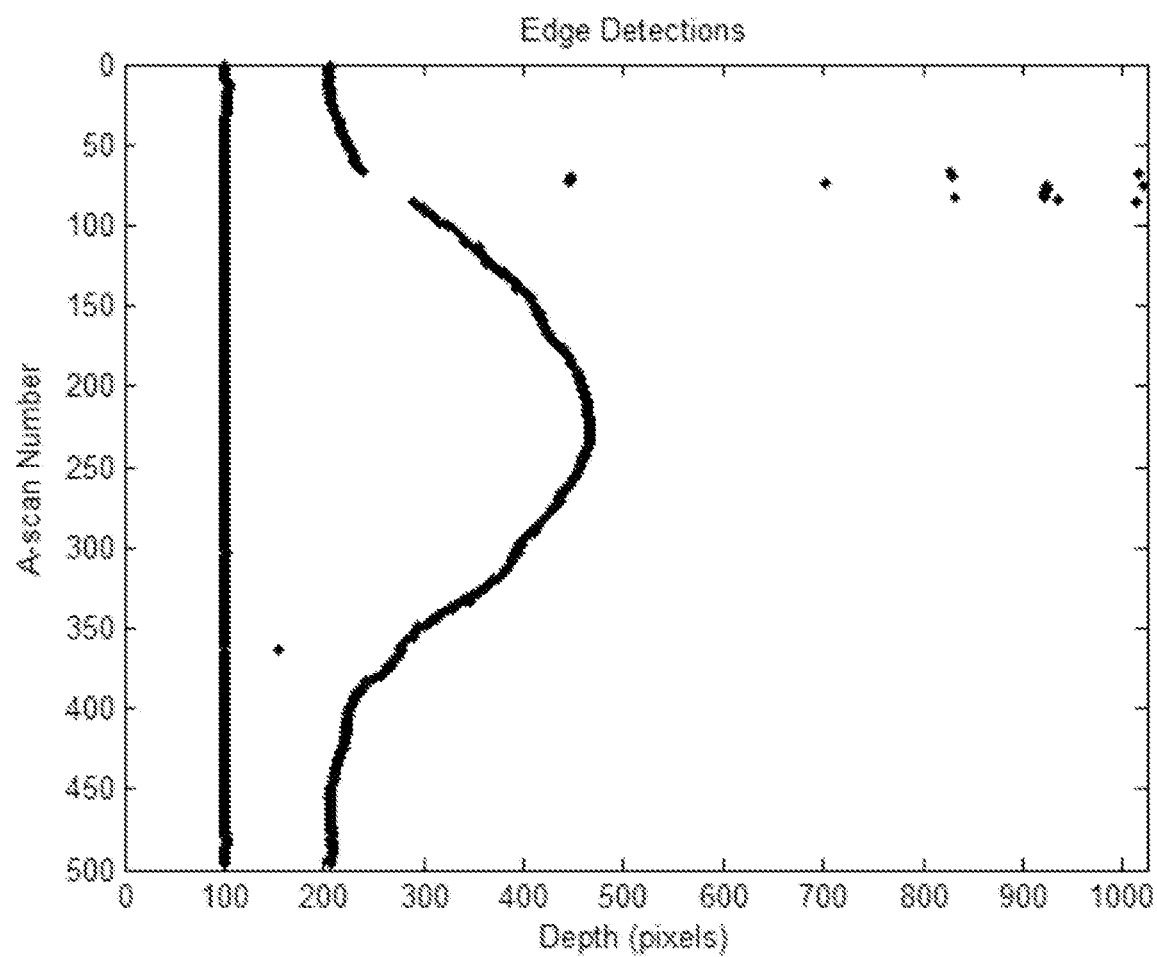
FIG. 26 shows the initial set of image points from an edge detection in which many of the detections are proximal to the sheath because of poor blood clearance around the sheath.
Figure 27:
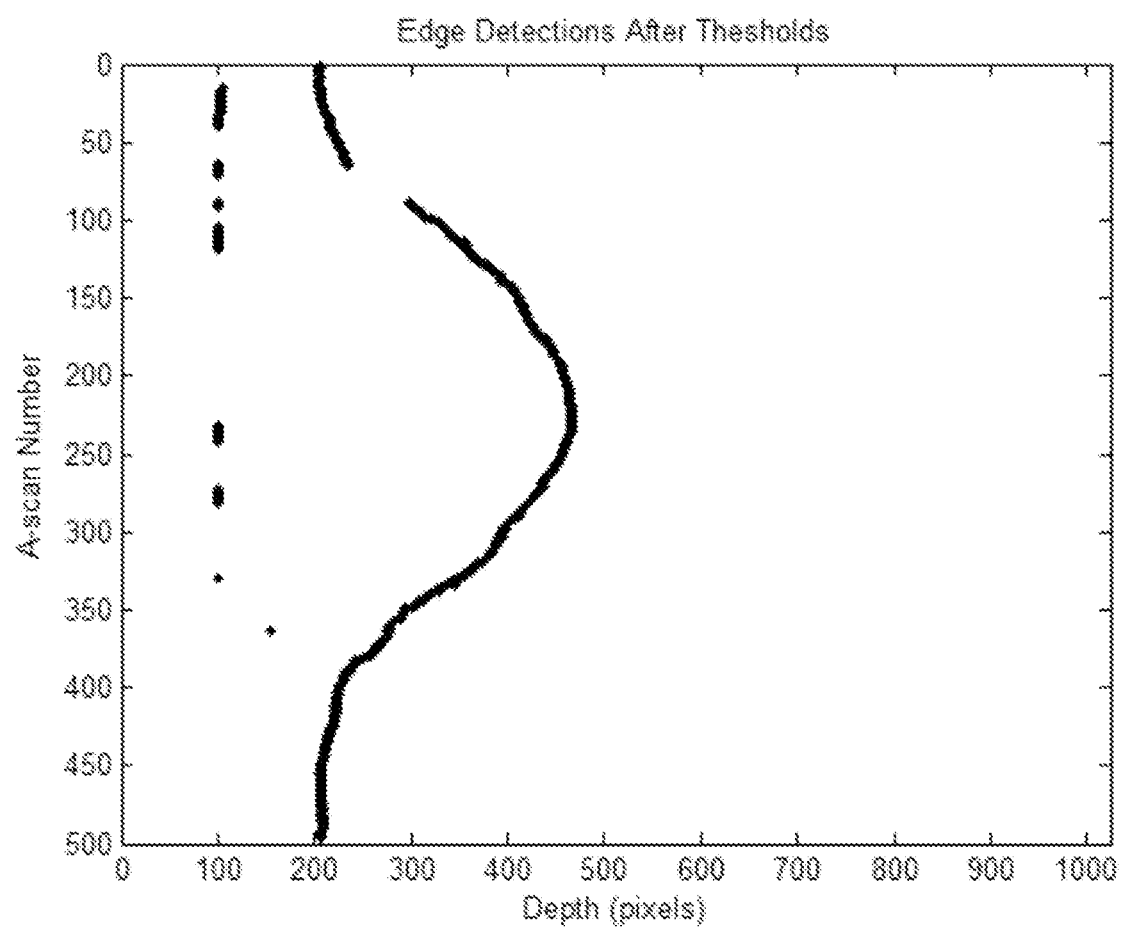
FIG. 27 illustrates the effect of applying a global and sheath amplitude threshold to detected image points.

In another embodiment, in addition to the global threshold $E_{min}$, another threshold is applied to peaks close to the imaging device sheath. Images with poor blood clearance will often result in detections around the sheath due to the edge created by setting the region inside the sheath outer diameter to the noise floor. In one embodiment, the threshold for points close to the sheath is computed based on the maximum signal in the image. The amplitude of data points close to the sheath may be within 5%, 10%, 15%, 20%, 25%, 30%, 35%, 40%, 45%, 50%, 55%, 60%, 65%, 70%, 75% of the maximum amplitude signal in the edge image. In FIG. 24 is provided an example of a B-scan of a vessel with poor blood clearance. The edge image shown in FIG. 25, having poor blood clearance, shows strong sheath signal and weak lumen edge signal. In FIG. 26 is shown the initial set of edge detections, in which many of the detections are close to the sheath because of poor blood clearance. In FIG. 27 is shown the set of remaining detections after the global and sheath thresholds are applied.

In a particular embodiment, below is provided a basic algorithmic outline of thresholds applied to the edge points:

if $(E_n(a, 1) < E_{min}) \vee [(P_n(a, 1) < S_{OD} + d_s) \wedge (E_n(a, 1) < t_{amp} \cdot \max(E_n)]$ then $P_n(a,1) = \text{NaN}$ elseif $(E_n(a, 2) < E_{min}) \vee [(P_n(a, 2) < S_{OD} + d_s) \wedge (E_n(a, 2) < t_{amp} \cdot \max(E_n)]$ then $P_n(a, 2) = \text{NaN}$ where $E_{min}$ is a predefined threshold for the minimum edge amplitude, $S_{OD}$ is the outer diameter position of the sheath, $d_s$ is the distance from the sheath outer diameter to apply the threshold parameter, $t_{amp}$ is the threshold scaling applied to the maximum edge amplitude for points close to the sheath. A variety of different threshold schemes may be applied to remove detections and the scope of this invention is not limited to the threshold scheme presented here.

Figure 28:
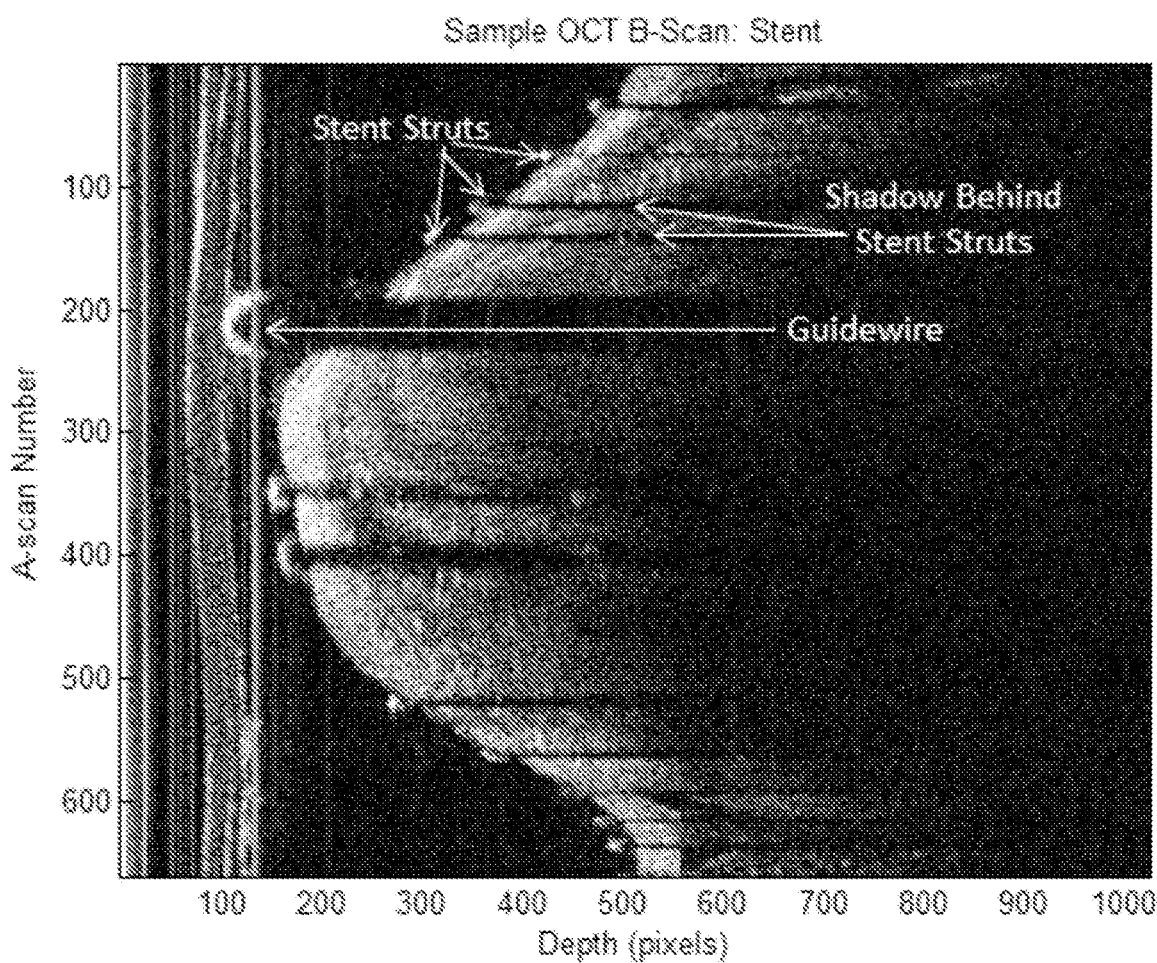
FIG. 28 shows a B-Scan image having shadow artifacts present.

Referring to FIG. 18, block 601 is for the evaluation of edge points within a shadow caused by, for example, stent or guide-wires attenuating the OCT light source from properly reaching a strong or robust edge. After a data set of edge points has been determined through the use of, for example, an edge detection algorithm, artifacts may be removed from the data set. Since an objective is to find the vessel lumen border, it is preferred that other detection artifacts be removed that may otherwise lead to erroneous border calculations. Artifacts can include "shadows" arising from the OTC catheter, for example stent and guide-wire shadows. In FIG. 28 provides an example B-scan with shadows present arising from guide-wire and stents. Stent struts and guide-wires may appear in an A-scan as a high amplitude signal followed by a shadow. It is desirable to remove shadows in the image and any points within A-scans containing these artifacts to prevent an automatic border detection algorithm from incorporating the signal from stent struts or guide-wires into the border detection calculations. In one embodiment, a shadow detection step can identify A-scans containing features such as guide-wires and removes all points within those A-scans.

In order to identify artifact shadows in the image, a computational amplitude threshold is applied to each A-scan in the image, and data points are removed based on their value relative to the threshold value. This threshold value can be, for example, computed based on a maximum amplitude signal in individual A-scans. In one example, points less than or greater than an amplitude of about 5 dB, 10 dB, 15 dB, 20 dB, 25 dB, 30 dB, 35 dB, 35 dB, 40 dB, 45 dB, 50 dB, 55 dB, 60 dB, 65 dB, 70 dB, 75 dB, 80 dB, 85 dB, 90 dB, 95 dB, 100 dB of the peak value and more than 1 dB, 2 dB, 3 dB, 4 dB, 5 dB, 6 dB, 7 dB, 8 dB, 9 dB, 10 dB, 15 dB, 20 dB, 25 dB, 30 dB, 35 dB, 40 dB, 45 dB, 50 dB above the noise floor for an individual A-scan can be included in the data set for computing an edge border. This threshold can then be applied to all A-scans across all frames.

Figure 29:
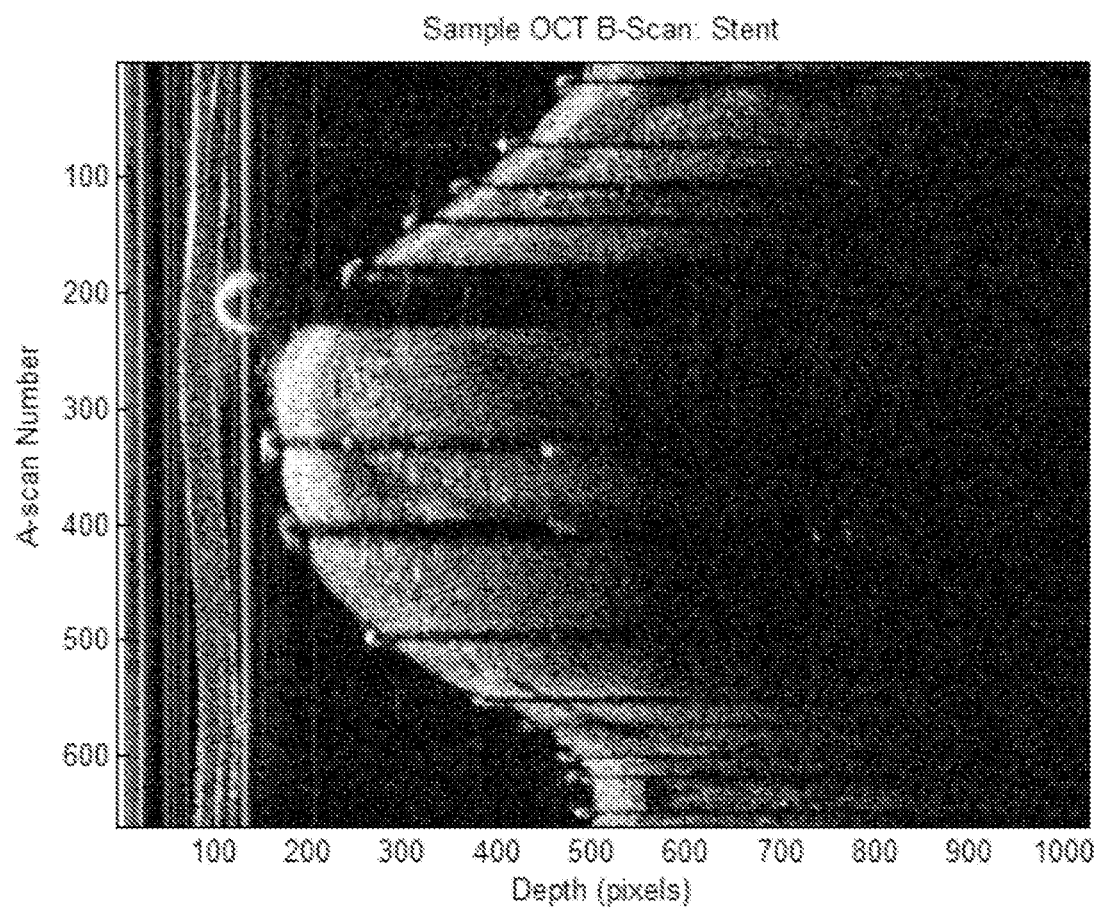
FIG. 29 shows an example B-scan requiring removal of stent shadows.
Figure 30:
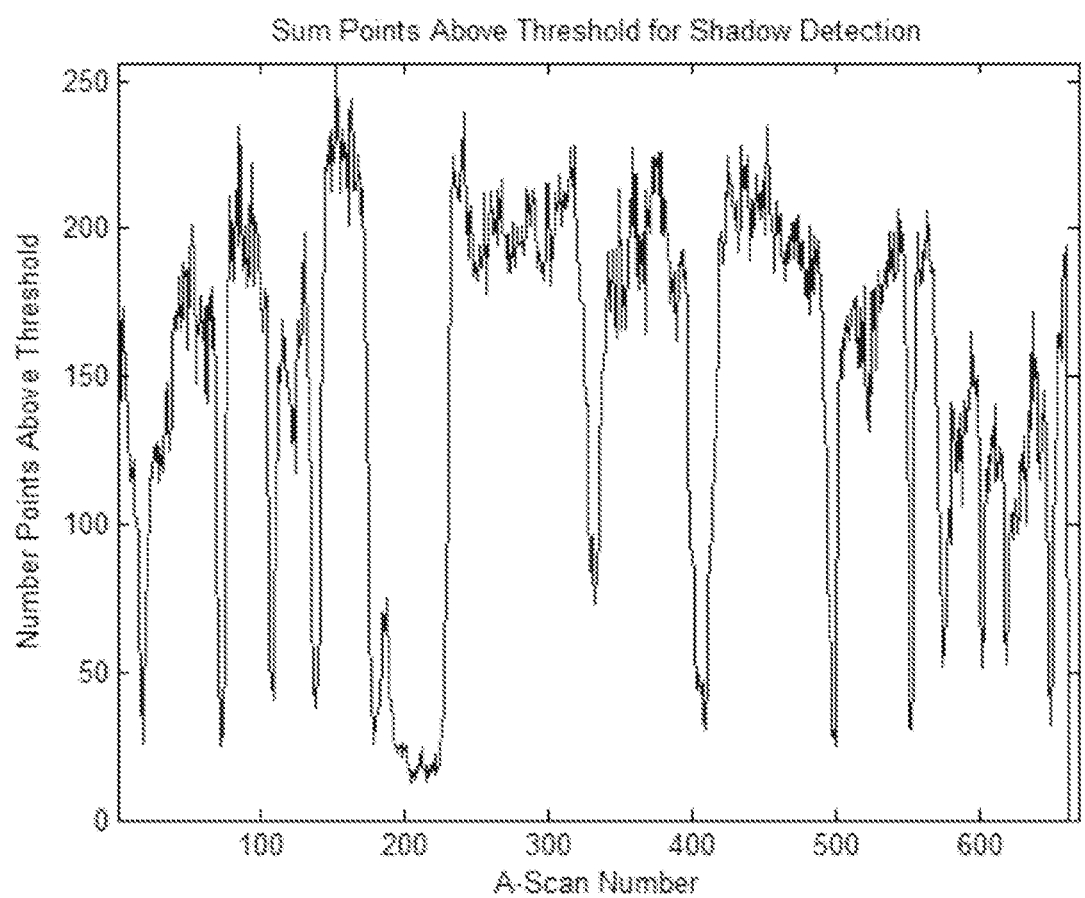
FIG. 30 shows a graph plotting A-scan data points.
Figure 31:
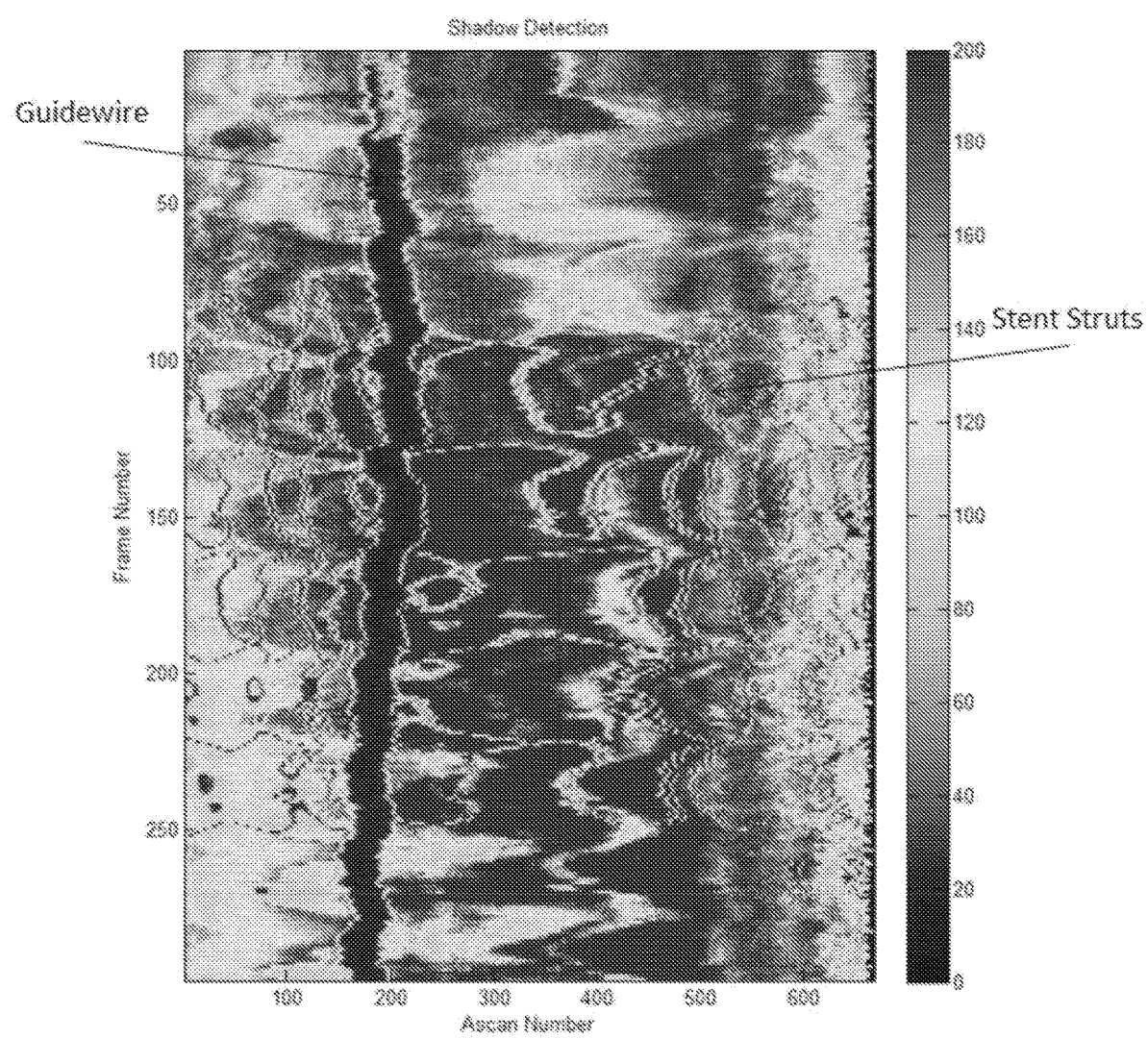
FIG. 31 shows a graph of A-scan data point amplitudes across B-scans.

An example of an individual B-scan frame containing a stent and requiring removal of stent shadows is shown in FIG. 29. FIG. 30 shows a graph with A-scan data points following the shadow profiles of the B-scan shown in FIG. 29. Regions containing a shadow can have a lower number of detections than neighboring regions with vessel tissue. FIG. 31 provides a graph of the A-scan signal amplitude across all B-scan frames where the guide-wire and stent struts are identified. The x-axis indicates the A-scan number, the y-axis indicates the frame number, and the shading indicates the number of points above the threshold.

Figure 32:
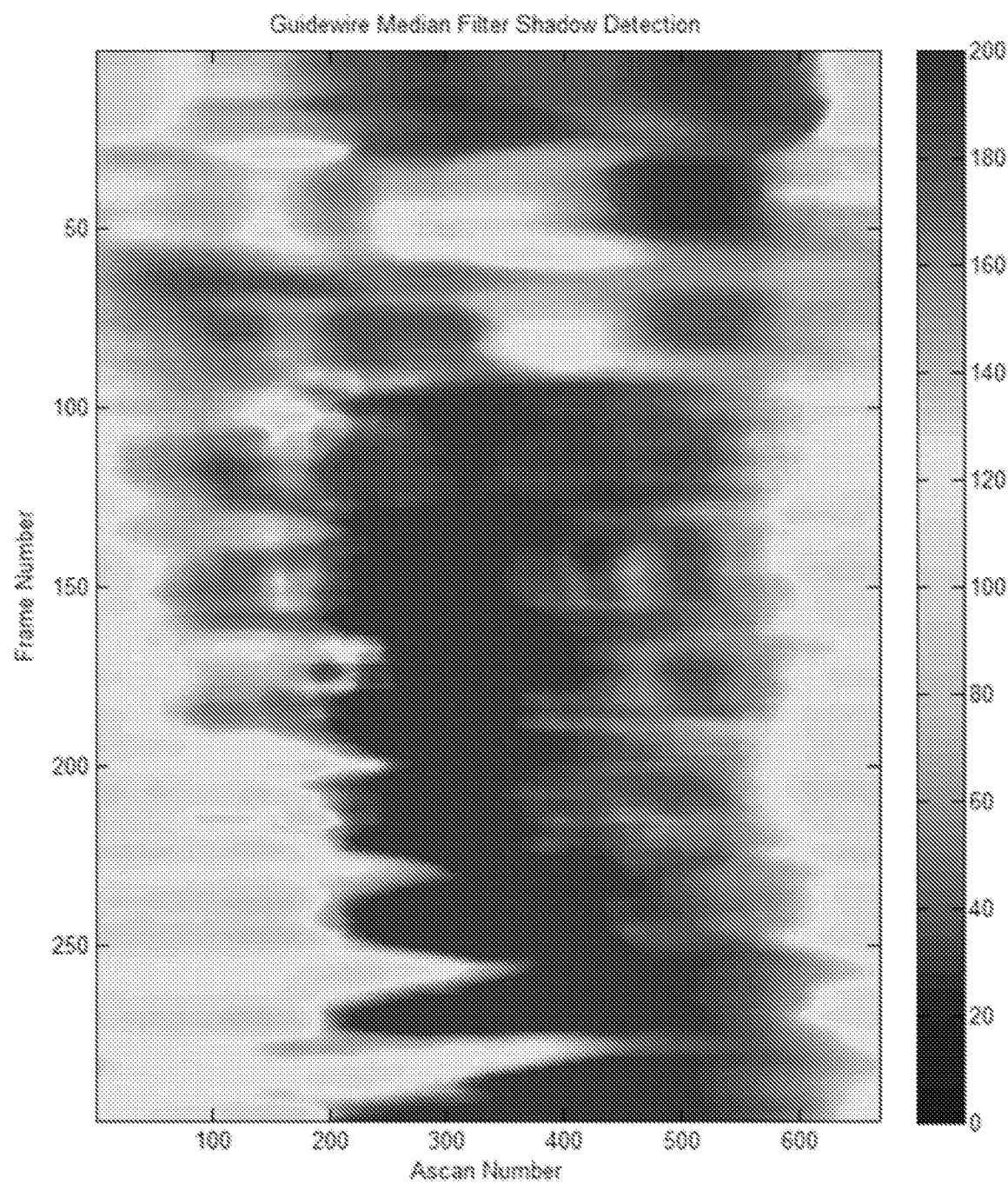
FIG. 32 shows the graph of FIG. 31 after having applied a median filter with a width corresponding to the known guide-wire width.
Figure 33:
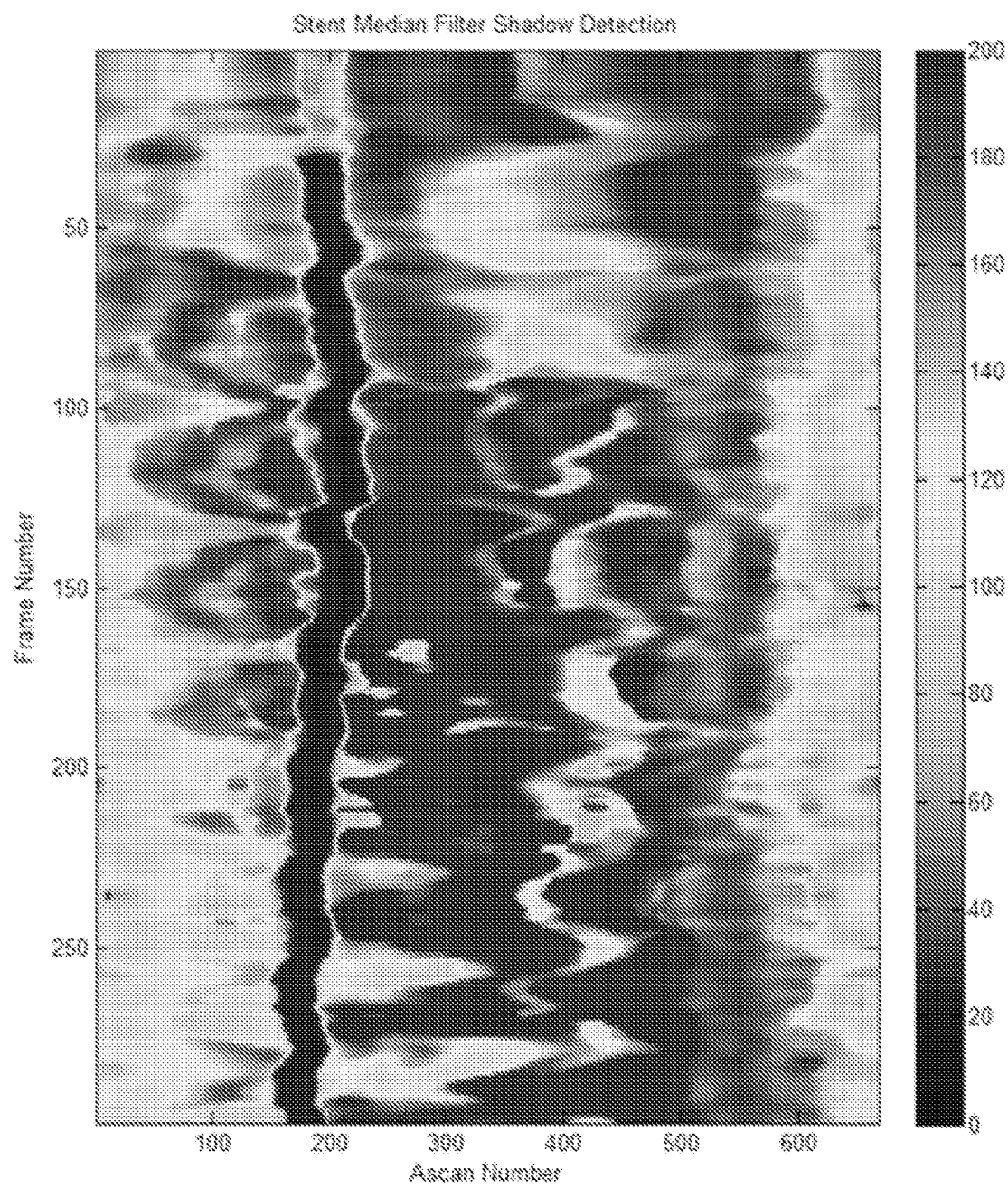
FIG. 33 shows a graph after having applied a median filter with a width corresponding to the known stent strut width.
Figure 34:
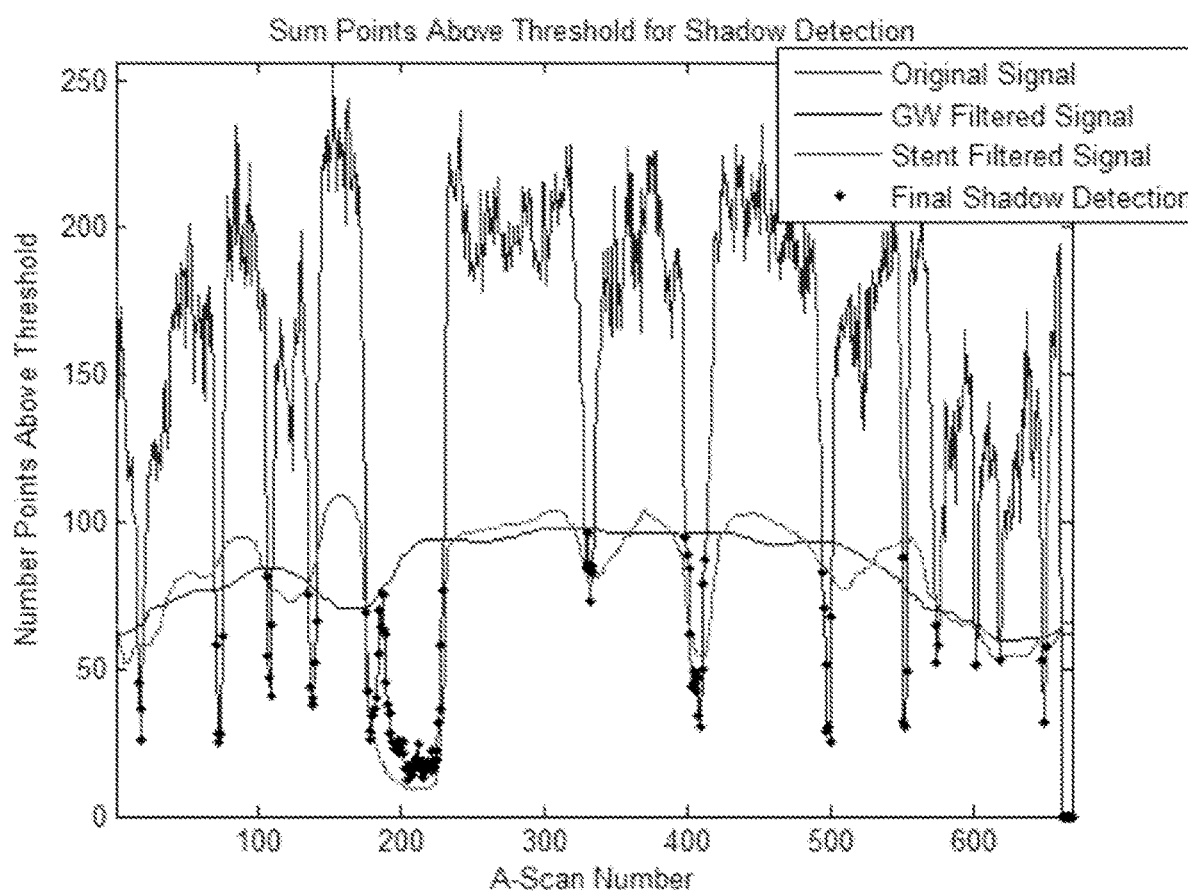
FIG. 34 shows a graph of an original signal for a B-scan and the corresponding threshold plots from the median filtered stent and guide-wire signal.

In other embodiments, once all frames have been processed for shadows, the resulting signal can be filtered to identify regions with a low number of detected image data points relative to neighboring A-scans and B-scan frames. A variety of filters may be applied. In one example, a median filter is employed in one dimension. In another example, a two-dimensional median filter is employed. The median filter can use any appropriate window size of neighboring data points, for example 1, 2, 3, 4, 5, 6, 7, 8, 9, 10, 15, 20, 30, 40, 50, 60, 70, 80, 90, 100. In certain embodiments the window size is directed at the specific artifact being filtered. In other embodiments, two or more median filters can be applied. In a particular example, two two-dimensional median filters are employed. A first median filter is used and sized to filter over stent regions; therefore the width can be at least twice or larger the size of the expected stent width in A-scans and wherein the frame dimension is determined based on the pullback speed. A second median filter can be employed and sized to filter over the guide-wire regions; therefore the width can be at least twice the size or more of the expected guide-wire width and wherein the frame dimension is also determined based on the pullback speed. In a related example, all points less than a predetermined value "x %" of the median filtered value can be classified as shadow detection. In FIG. 32 is shown a graph of the A-scan signal amplitude across all B-scan frames where the guide-wire and stent struts are identified and after the guide-wire median filter is applied. In FIG. 33 is shown a graph of the A-scan signal amplitude across all B-scan frames where the guide-wire and stent struts are identified and after the stent median filter is applied. For FIGS. 32 and 33, the x-axis indicates the A-scan number, the y-axis indicates the frame number, and the shading indicates the number of points above the threshold. In FIG. 34 is provided a graph of an original signal for a B-scan and the corresponding thresholds plots from the median filtered stent and guide-wire signals. In FIG. 34, the black points indicate A-scans having data point amplitude values below the threshold values and therefore are selected as A-scans with shadows. Any remaining edge points which lie in an A-scan with a shadow can then be removed from the edge point data set using, as one example, the following basic algorithm:

if shadow (a)=true
       $P_n(a,1)$=NaN
       $P_n(a,2)$=NaN
    end where shadow (a) is a Boolean array indicating if a shadow is present in a-scan a. After all filtering steps are completed for the present example, the number of remaining edge points per A-scan may range from 0 to 2.

Referring to FIG. 18, block 602 is for the cycling through remaining edge points and selecting one or more sets of seed points that most closely match the position of the starting data points. A set of seed points may be selected from the set of edge points and used for border calculation. Seed points can be any set of edge points of at least two seed points. There are several ways in which seed points can be selected, for example the user may manually choose points from a displayed data set. In one example, seed points are automatically generated. An automated approach may be to select a subset of points from the set of edge points as a function of the seed point amplitude or location. In a particular example, an algorithm is employed to select a pair of seed points by iterating through each of the edge points and identifying the second data point closest to being 180° away (for example, half the number of A-scans away). The algorithm can then, for example, interpolate a full 360° closed contour using those two points.

Certain interpolation schemes are desirable for a particular class of interpolants, and thus may be chosen accordingly. Interpolative schemes can be confined to regression analysis or simple curve fitting. In other examples, interpolation of trigonometric functions may include, when better suited to the data, using trigonometric polynomials. Other interpolation schemes contemplated herein include, but are not limited to, linear interpolation, polynomial interpolation and spline interpolation. Still other interpolative forms can use rational functions or wavelets. Multivariate interpolation is the interpolation of functions of more than one variable, and in other examples multivariate interpolation is completed with include bilinear interpolation and bicubic interpolation in two dimensions, and tri-linear interpolation in three dimensions. To ascertain the accuracy of the interpolated or calculated contour, the numerical distance (the difference in the depth) between the calculated contour and the closest edge point for each A-scan can be computed and summed. An interpolation and distance summation is preferably computed for every available edge point and corresponding point at the interpolated contour. Equation 2 provides on example for the area calculation:

$$A_{seed}(s) = \sum_{a=1}^{N} \min[|C_{int\_erp}(a) - P_n(a, 1)|, |C_{int\_erp}(a) - P_n(a, 2)|] \quad \text{EQUATION 2}$$

where s refers to a potential seed point; s is the index of a point from the set of all edge points not equal to NaN; $C_{int\_erp}$ (a) is the interpolated contour for potential seed point s at a-scan a; $P_n$ (a,1) and $P_n$ (a,2) are the remaining edge points as defined in the previous steps for frame n, if an edge point is NaN it is not included in the sum; N is the total number of a-scans in frame n.

Figure 35:
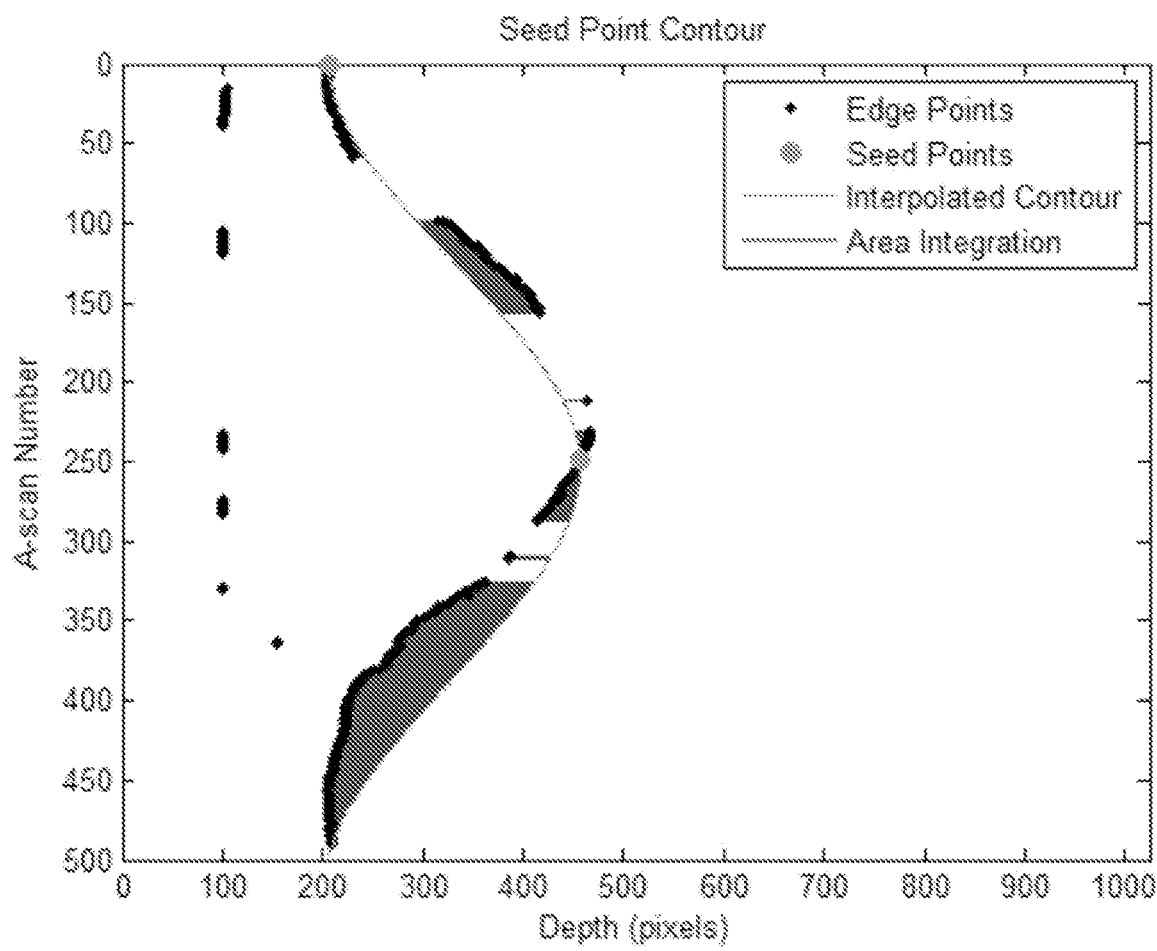
FIG. 35 shows an example plot of one resulting interpolated contour using a first set of seed points.
Figure 36:
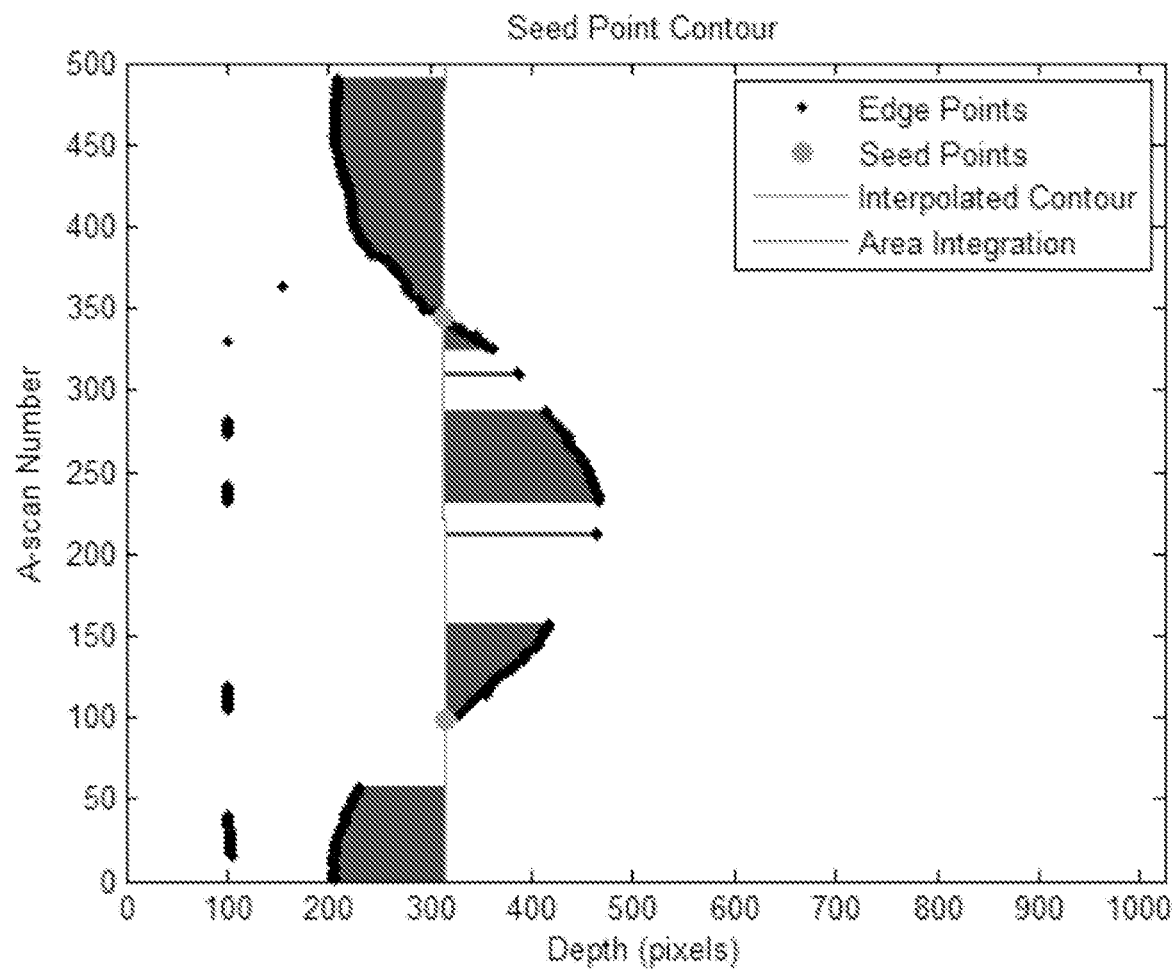
FIG. 36 shows an example plot of one resulting interpolated contour using a second set of seed points.
Figure 37:
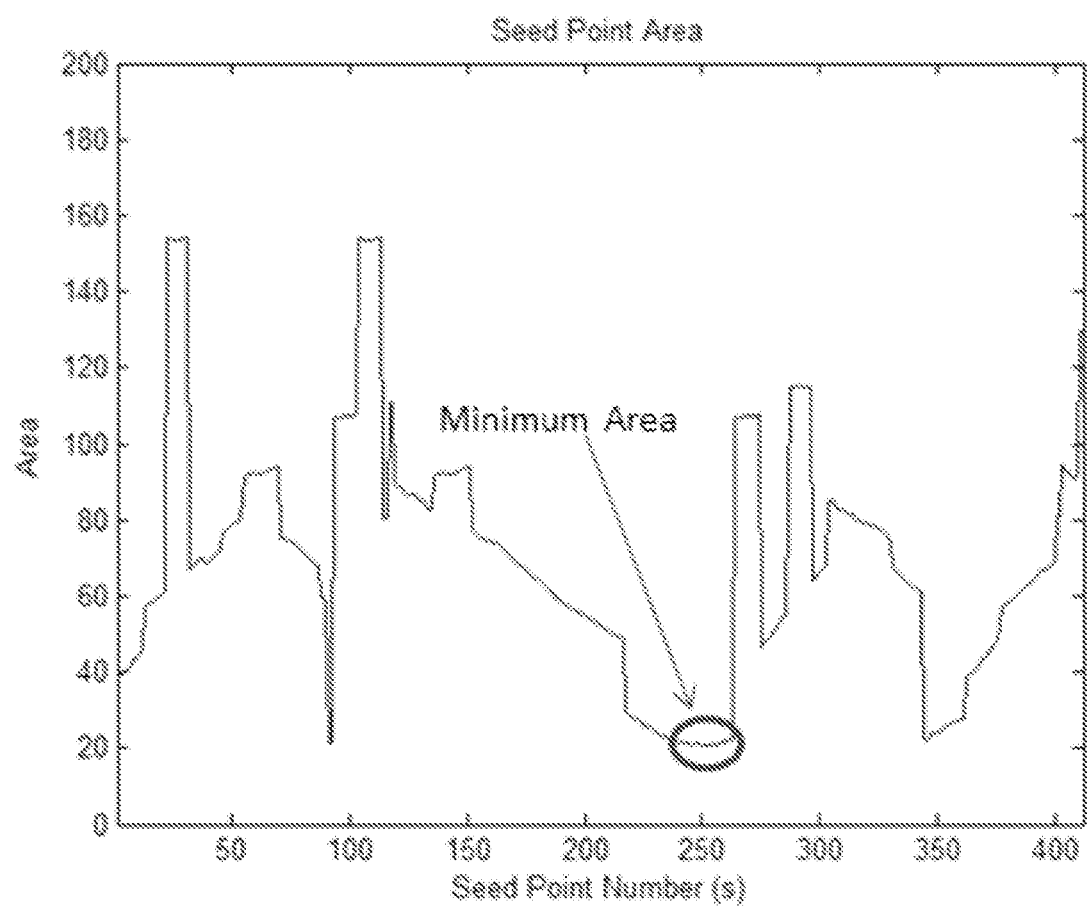
FIG. 37 shows a graph of a resulting difference areas plotted against potential seed points determined in an example lumen border calculation.
Figure 38:
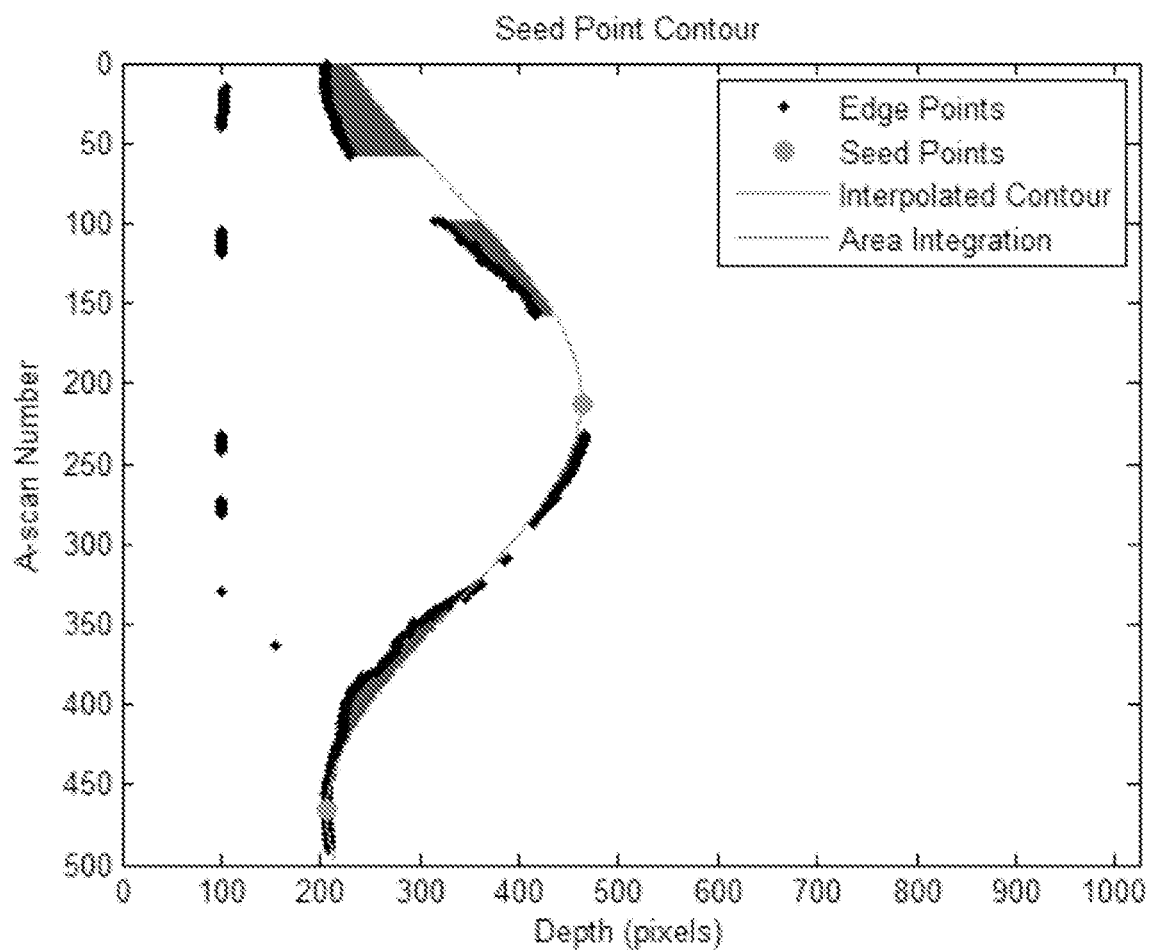
FIG. 38 shows a final graph of the resulting contour interpolated with a set of seed points yielding a minimum difference area.

The set of points with the smallest area (i.e. smallest difference between edge points and interpolated contour) may be selected as the set of seed points for use in the final lumen border calculation. Shown in FIG. 35 is an example of the resulting interpolation contour using a first set of candidate seed points. The area encompassed by the horizontal lines, corresponding to the area difference between the contour and the originally detected data points, is summed and recorded for each potential set of seed points shown as large dots on the contour. If an A-scan contains multiple points (as described herein), the point closest to the contour is used to compute the area. Shown in FIG. 36 is another example of a set of potential seed points, the corresponding interpolated contour and difference area between the raw data points and the contour. In this example there is a large gap between the contour and the edge points, therefore this set of points will have a large area and is unlikely to be selected for incorporation as a set of seed points. Shown in FIG. 37 is a graph of the resulting difference area plotted against all potential seed points determined with this example lumen border calculation, and presents the set with a minimum difference area. Shown in FIG. 38 is a final graph of the resulting contour interpolated with seed points yielding a minimum difference area. As shown therein, the calculated contour from the set of seed points with the smallest summed area difference closely follows a majority of the lumen edge points in the image.

Referring to FIG. 18, block 603 is for the identification of seed points used to define a midpoint, which itself is used to refine the calculated lumen border. The seed points and corresponding interpolated contour can be utilized to begin the optimal border selection procedure. In this exemplification, the method for identifying the border is very similar to the method of seed point selection in that it utilizes interpolation and difference area calculation to select the optimal border location.

Figure 39:
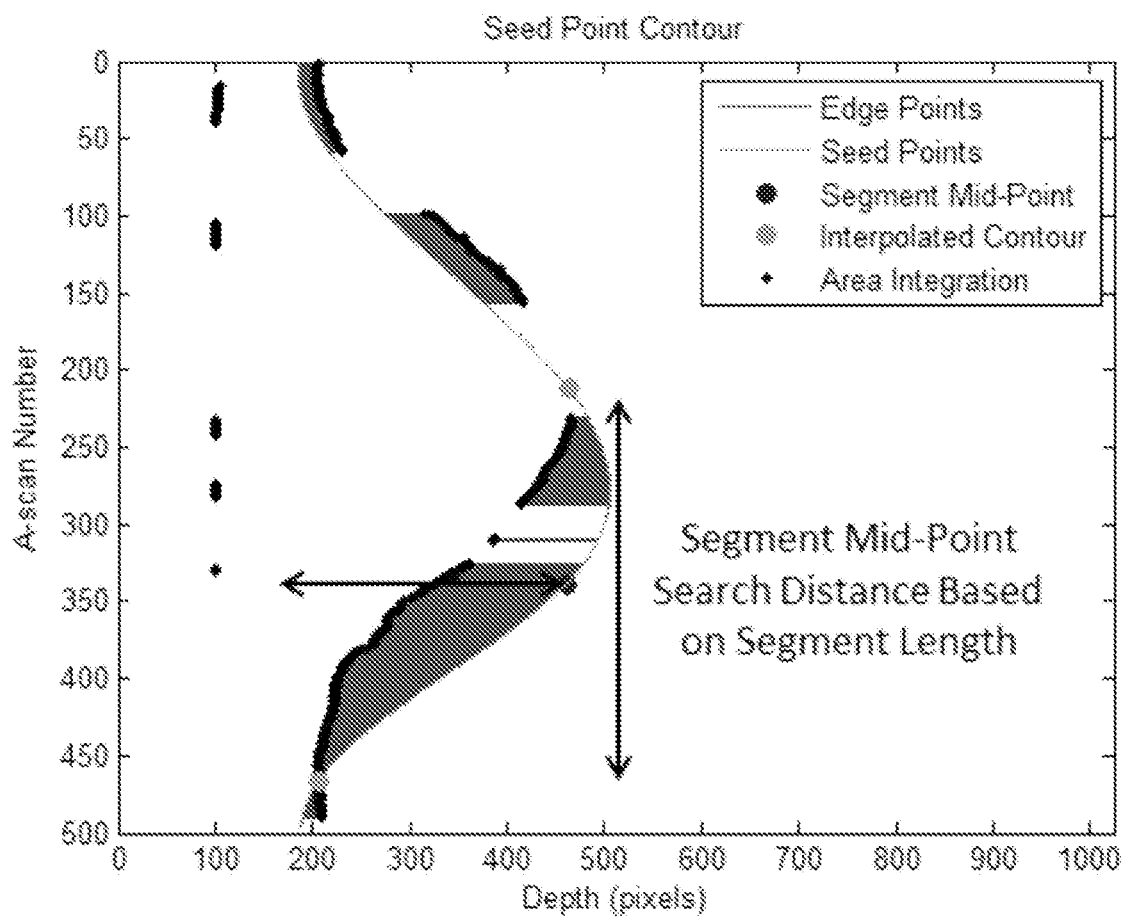
FIG. 39 shows a graph of a calculated contour corresponding to a first segment search based on segment length and mid-point position.
Figure 41:
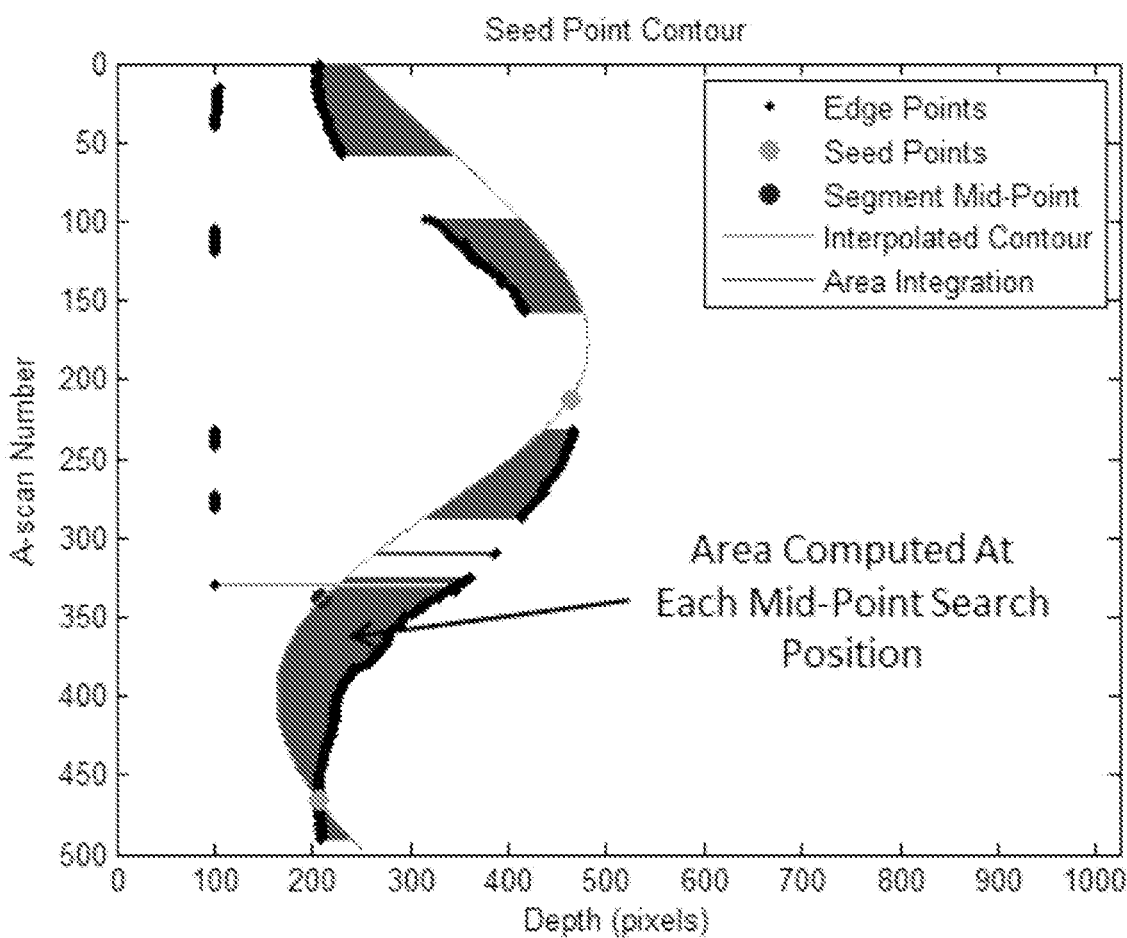
FIG. 41 shows a graph of the midpoint as shown in FIG. 39, but used for another search position

For each segment created by the seed points, the mid-point is preferentially shifted in the axis indicating A-scan number. For example, for any A-scan, the mid-point is shifted away from the calculated contour position and toward the data point indicating the catheter sheath amplitude threshold cutoff, and/or away from the contour and away from the data point indicating the catheter sheath amplitude threshold cutoff. The total horizontal distance the mid-point is shifted is based on the length of the segment. In FIG. 39 is provided a graph of a calculated contour corresponding to a first segment search, based on segment length and mid-point position. In FIG. 41 is provided a graph of the same mid-point, used for another search position. At each of the shift points a new contour is constructed by interpolating the contour with seed points and a segment mid-point location. The difference area is then computed between a calculated contour and the closest edge point in each A-scan, with the total difference area summed for each set of seed points.

Figure 40:
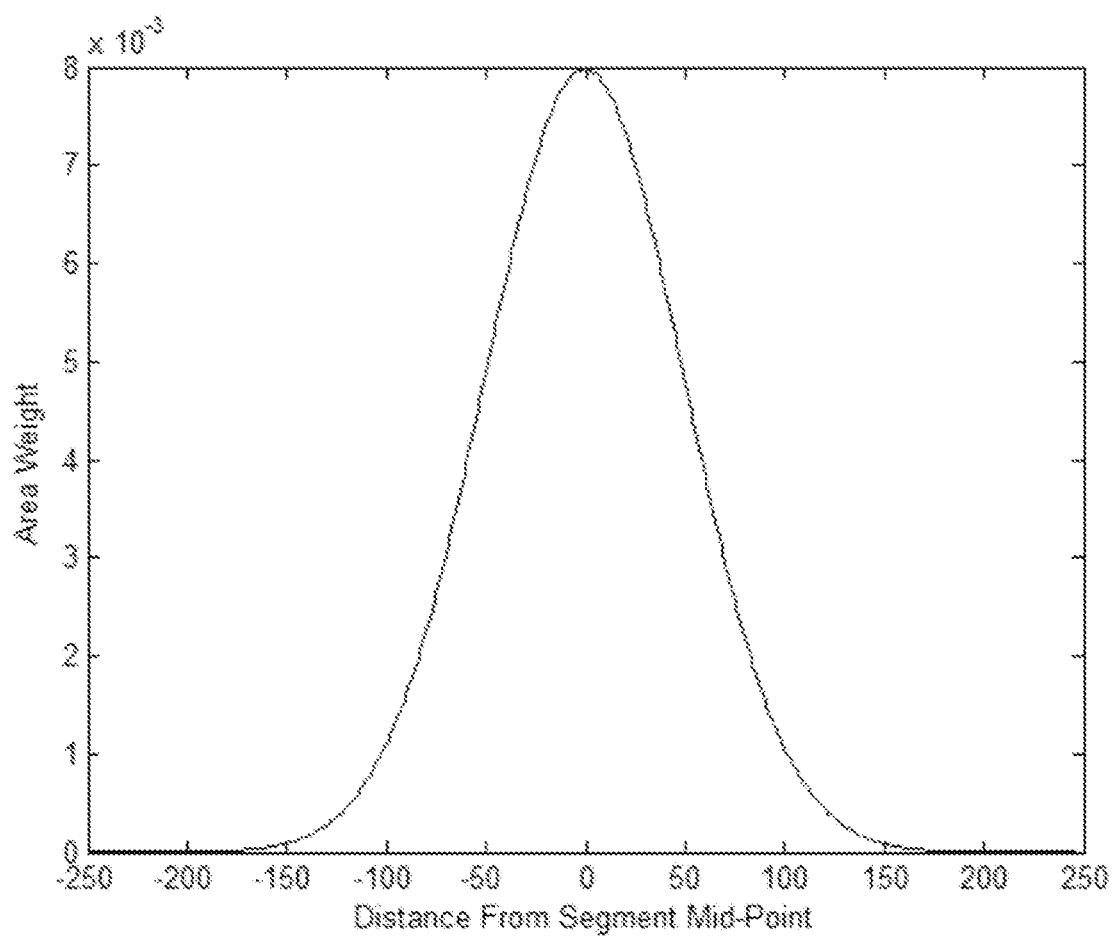
FIG. 40 shows a graph of an example weighting scheme.

In another example, the difference area can be weighted or biased based on the distance from the mid-point. For example, points closest to the mid-point can be weighted more than those further away. In FIG. 40 is provided a graph of an example of a weighting scheme used for the difference area calculation, in which positions further away from the segment mid-point have different weighting bias than those positions close to the segment mid-point. In these examples a weighting function is used where points further from the segment midpoint are biased based on a predetermined Gaussian (or normal) shaped curve. Gaussian curve variants, including but not limited to the Laplacian-Gaussian or multivariate and univariate forms, are contemplated, but any weighting function designed to achieve the desired cutoff characteristic for determining a data point as being included as part of a lumen border can be incorporated into the methods and systems presented herein.

In another particular embodiment, the distance of the calculated contour to the edge data points in the neighboring frames may be incorporated in the calculation for determining the search location of the interpolated contour having a minimum difference area. In some exemplifications, the weighting scheme can be applied to the frames such that the current frame has the most weight or highest preferential bias for determining the optimal border location, although it is contemplated that the weighting formulating can be differentially or equally applied for a predetermined window size of frames.

Figure 42:
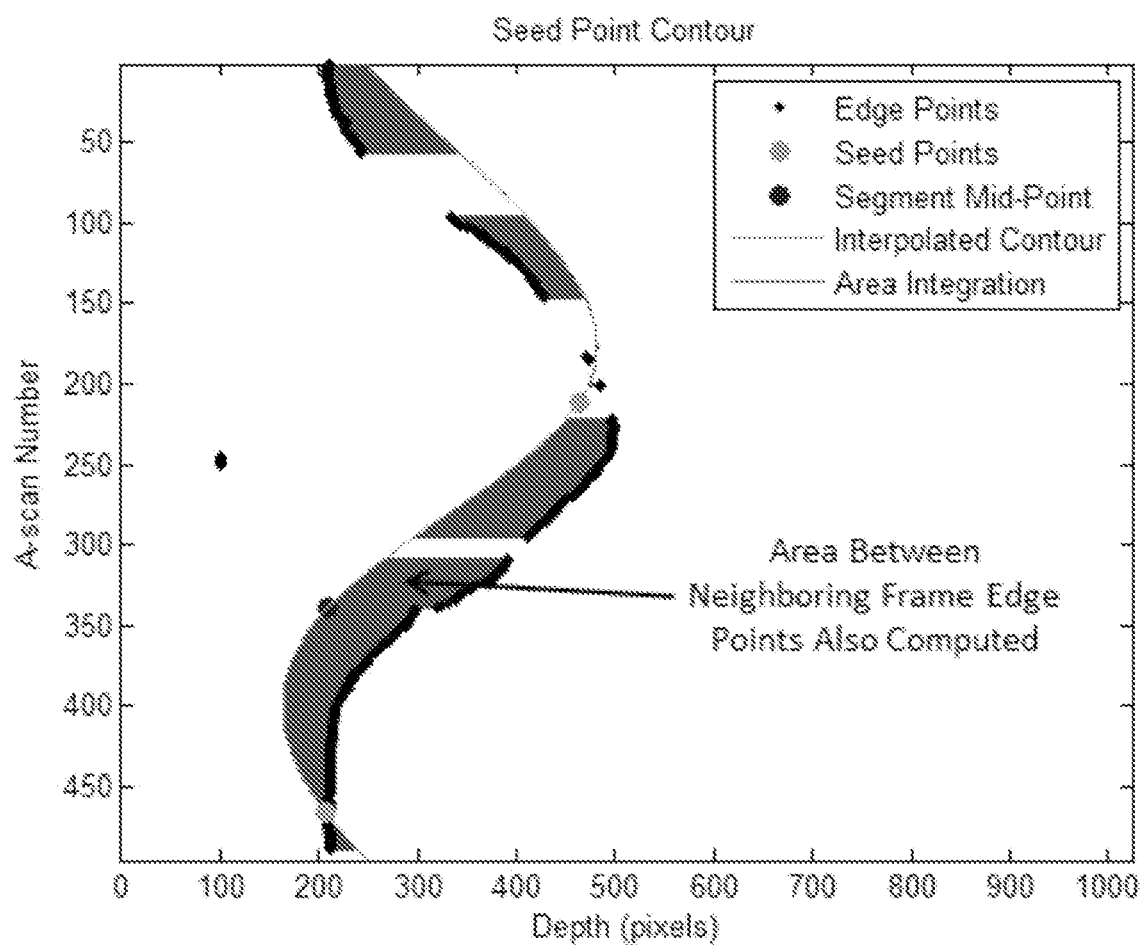
FIG. 42 shows an example graph of a difference area between mid-point search position and prior frame edge points.
Figure 43:
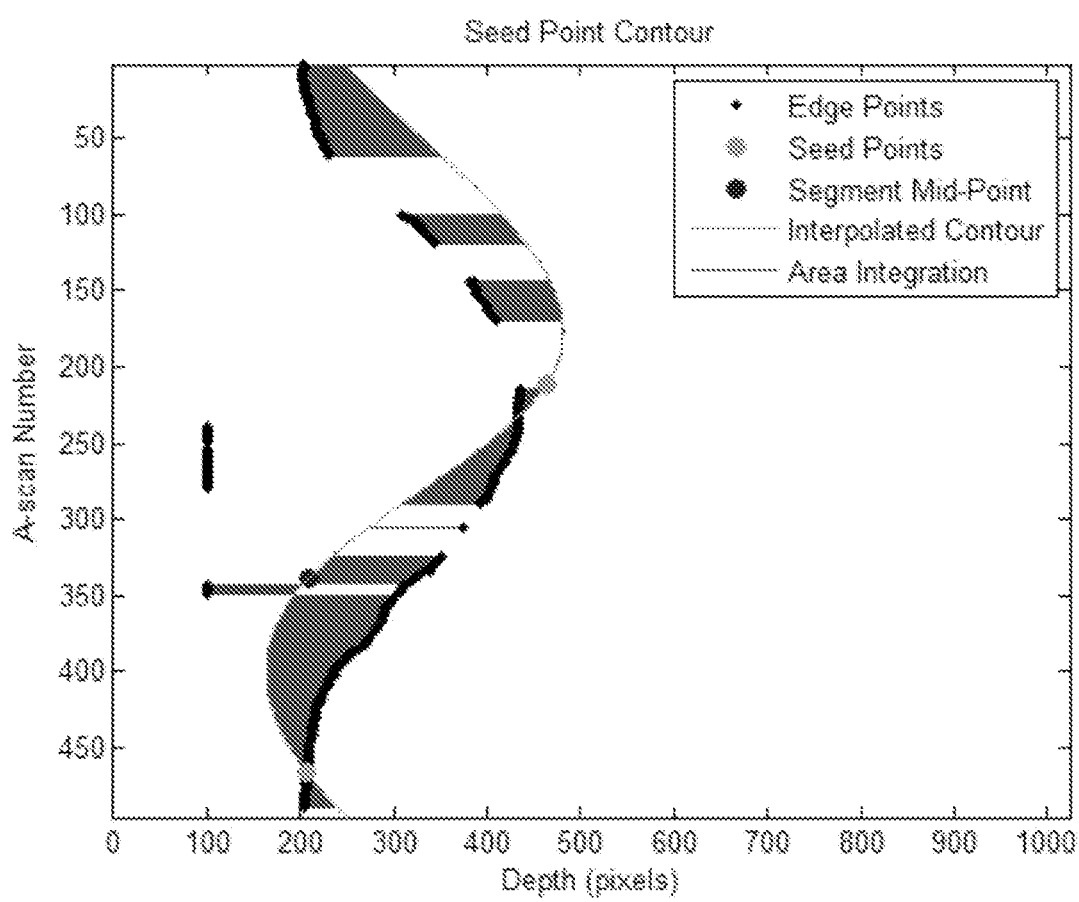
FIG. 43 shows an example graph of a difference area between the mid-point search position and next-frame edge points.
Figure 44:
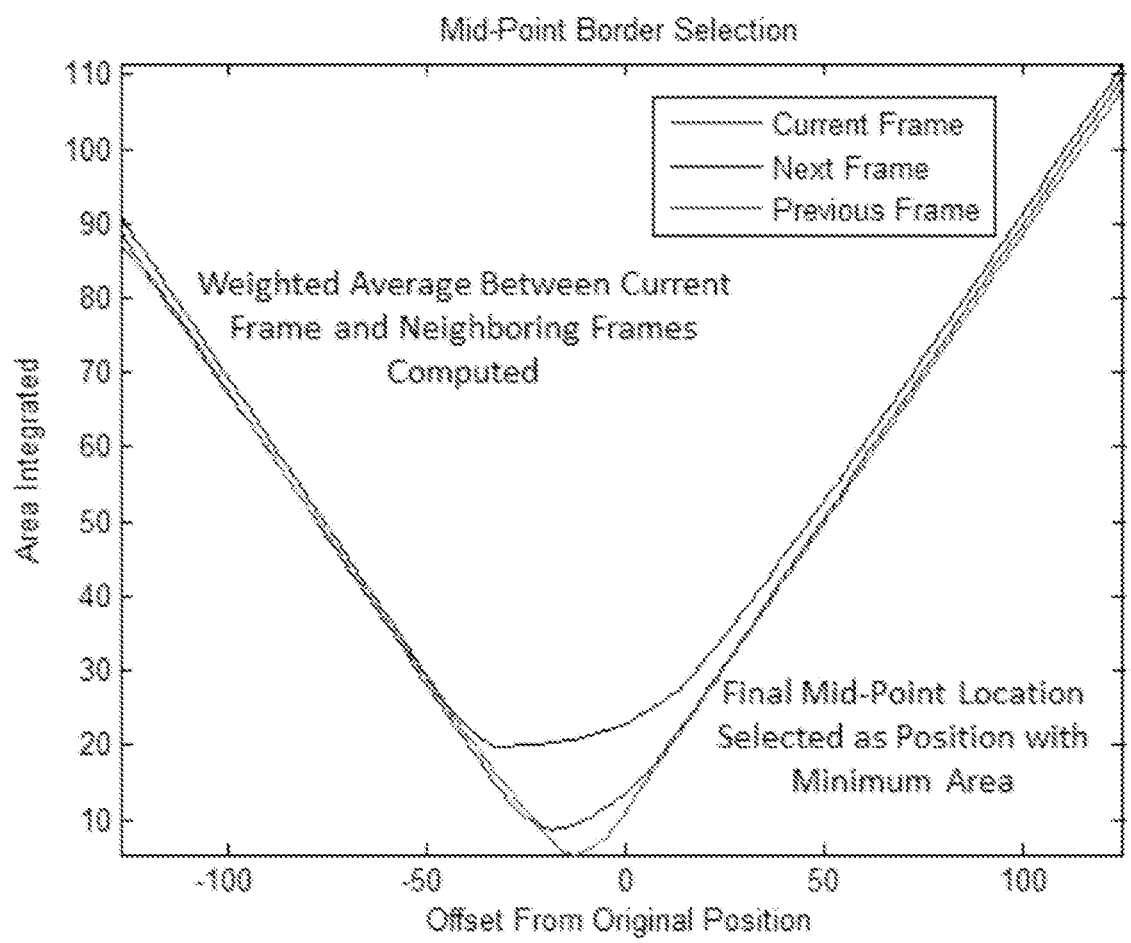
FIG. 44 shows the difference areas for all search positions for mid-point shown in FIGS. 42 and 43.
Figure 45:
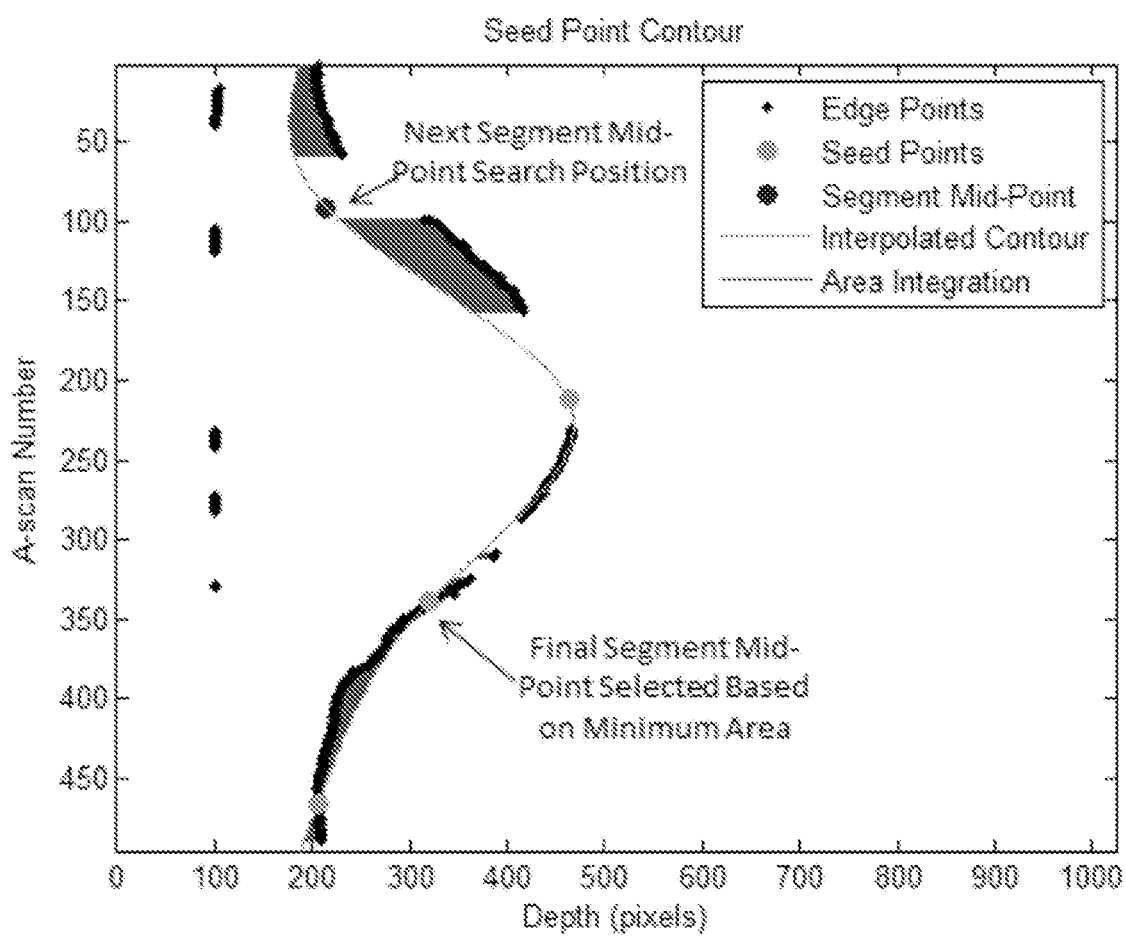
FIG. 45 shows a calculated contour from a minimum difference area selected as the final calculated border.
Figure 46:
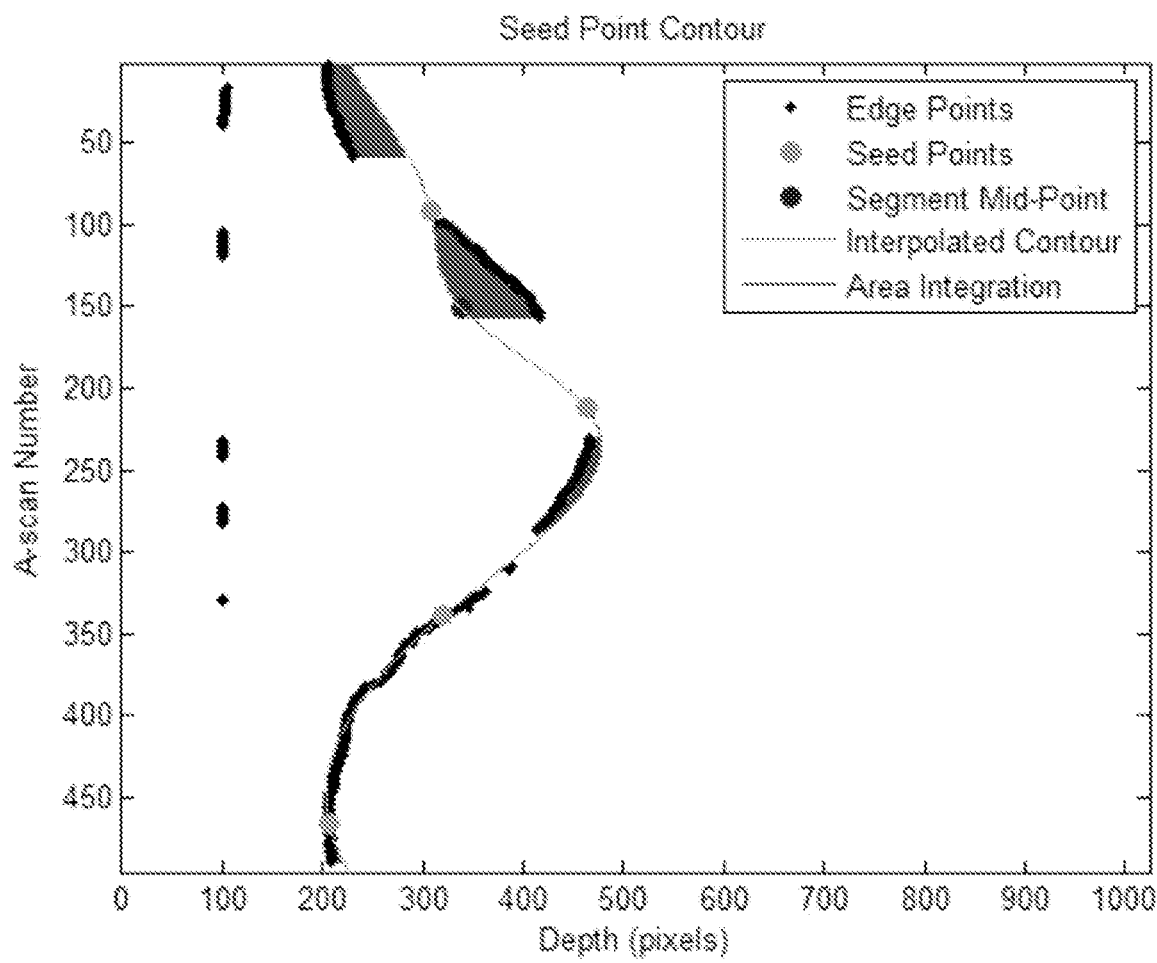
FIG. 46 shows an example where four data points have been defined and the search algorithm has computed an area for a candidate position for the fifth point.
Figure 47:
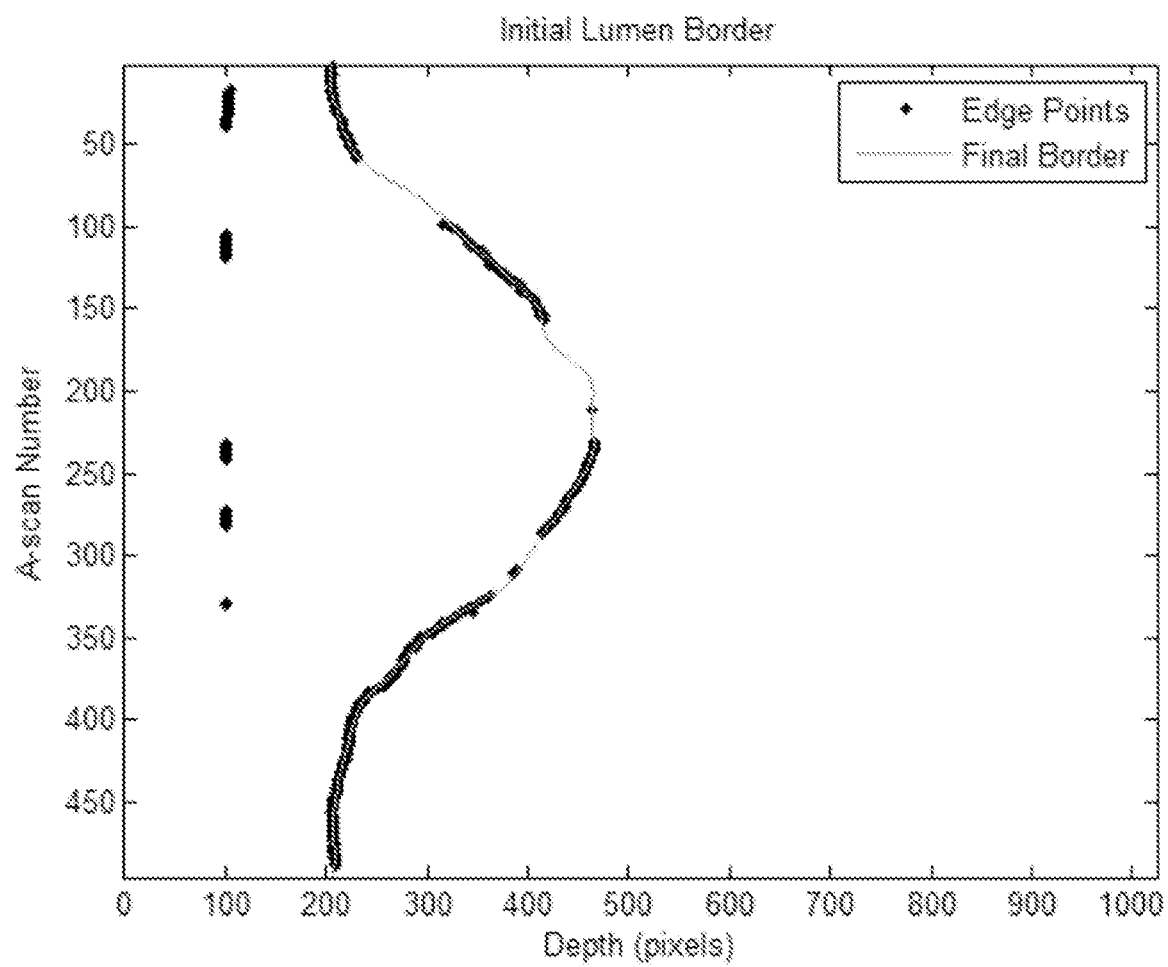
FIG. 47 shows a plot of a final calculated lumen border contour edge points.
Figure 48:
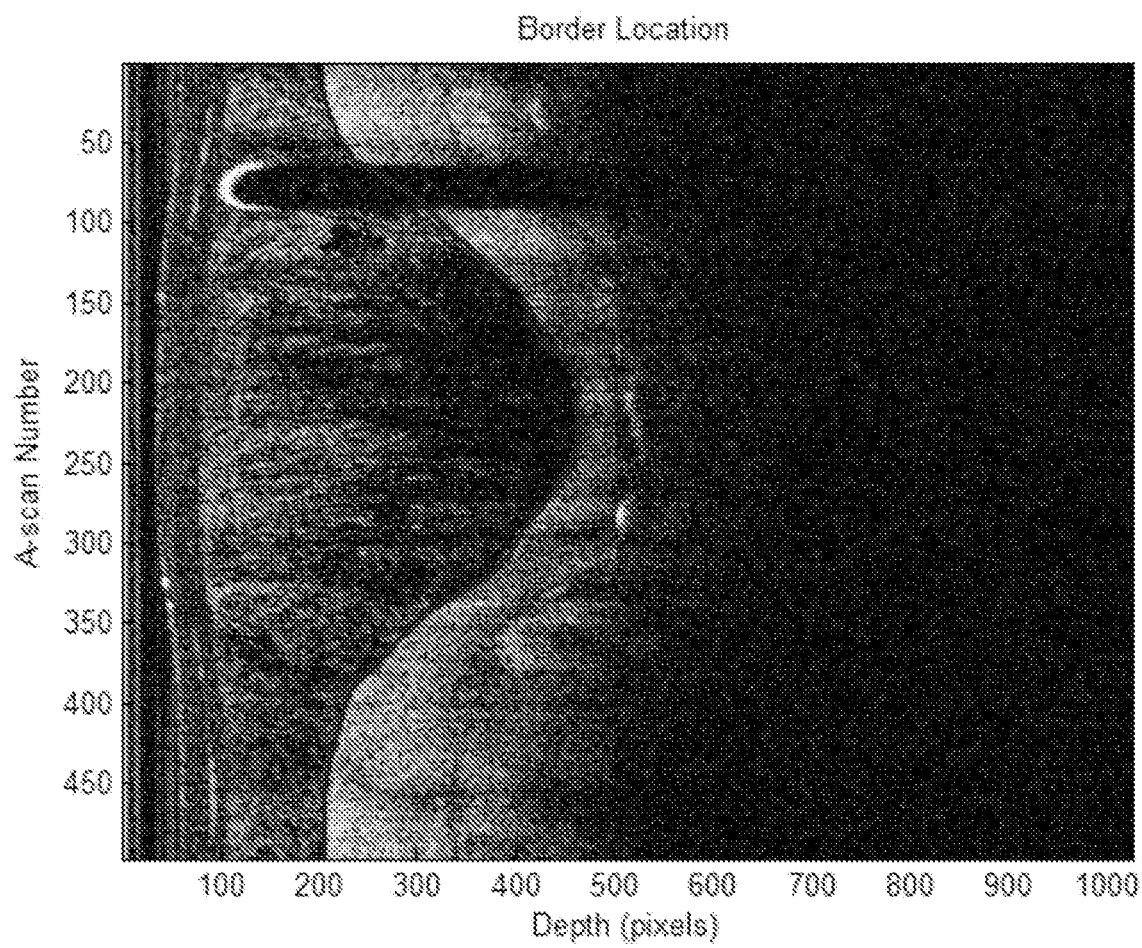
FIG. 48 shows a final calculated contour over-laid on a polar image.
Figure 49:
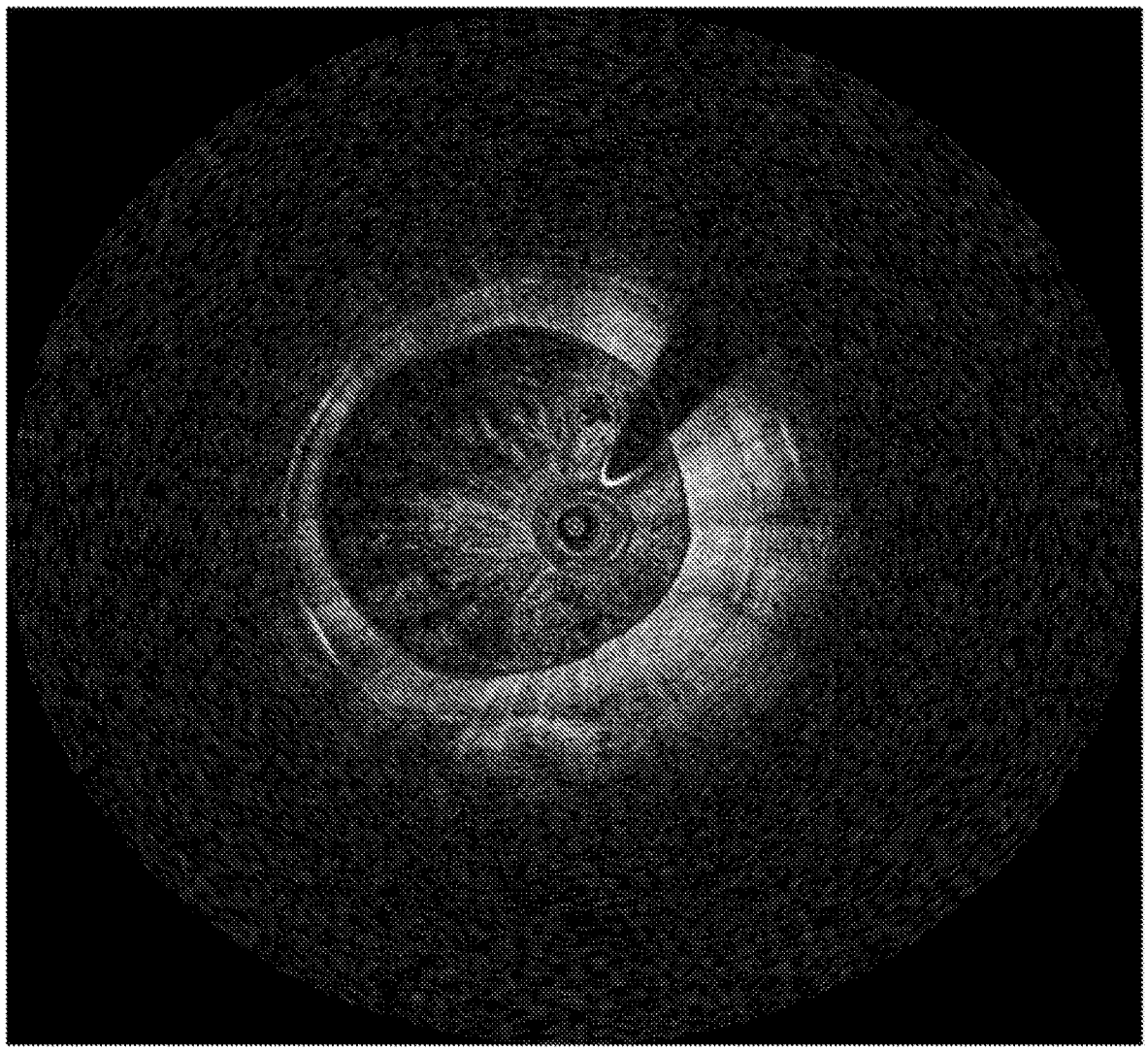
FIG. 49 shows a final calculated lumen border transformed to Cartesian coordinates and over-laid on a scan-converted tomographic image.

In FIG. 42 and FIG. 43 are shown graphs demonstrating the difference area calculation for the mid-point search position in the frame before and after the current frame. The resulting difference area calculations for each search position are provided in graphical form in FIG. 44. The location of the calculated contour providing the minimum difference area is selected as the final border; the corresponding contour is provided in FIG. 45, wherein the position with the smallest difference area has been selected for the seed points used in graphs shown in FIGS. 38-45. In FIG. 46 is provided an example where four data points have been defined and the algorithm has computed the area for a candidate position for the fifth point. This is iteratively repeated for every segment until all segments have been defined. A plot of the final calculated contour is provided in FIG. 47. In FIG. 48 is shown the final calculated lumen border plotted on the original polar-coordinate image. In FIG. 49 is shown the final calculated lumen border transformed to Cartesian coordinates and plotted on the scan-converted tomographic image, showing that the border closely follows the vessel lumen border despite poor blood clearance.

An exemplary equation for computing the difference area, $A_{border}$, between the edge points and interpolated contour at a search position x is provided in Equation 3:

$$A_{border}(x) = \quad \text{EQUATION 3}$$
$$w_{image}(n) \Big( \sum_{a=1}^{N} w_{ascan}(a) \cdot \min[|C_{int\_erp}(a) - P_n(a, 1)|,$$
$$|C_{int\_erp}(a) - P_n(a2)|] \Big) \sum_{a=1}^{N} w_{ascan}(a) p_n(a) +$$
$$w_{image}(n+1) \Big( \sum_{a=1}^{N} w_{ascan}(a) \cdot \min[|C_{int\_erp}(a) - P_{n+1}(a, 1)|,$$

-continued $$|C_{int\_erp}(a) - P_{n+1}(a, 2)|] \sum_{a=1}^{N} w_{ascan}(a) p_{n+1}(a) +$$

$$w_{image}(n-1) \Big( \sum_{a=1}^{N} w_{ascan}(a) \cdot \min[|C_{int\_erp}(a) - P_{n-1}(a, 1),$$

$$|C_{int\_erp}(a) - P_{n-1}(a, 2)|] \sum_{a=1}^{N} w_{ascan}(a) p_{n-1}(a)$$

where x refers to one of the candidate mid-point positions; $C_{int\_erp}$ (a) is the interpolated contour for all completed points and segment mid-point position x; $P_n(a,1)$ and $P_n(a,2)$ are the remaining edge points as defined in the previous steps for frame n; if an edge point is NaN it is not included in the sum; $P_n$ is an array of 0 and 1, where $p_n(a)$ is 0 if both $P_n(a,1)$ and $P_n(a,2)$ are NaN, otherwise $p_n(a)$ is 1; N is the total number of a-scans in a frame (assuming constant across all frames); $w_{ascan}(a)$ indicates the weight applied to a-scan a; $w_{image}(n)$ indicates the weight applied to the summation for frame n.

Alternate approaches to the final border selection step described herein also may lead to accurate border calculations. In one example, a method encompasses setting a selected mid-point position to be biased with a maximum gradient within the search distance. This method selects the position of the maximum gradient as the mid-point position for every segment but does not compute the difference area for the searched contour positions. This approach, therefore, preempts utilizing neighboring A-scan information or neighboring B-scan frame information to calculate a lumen border location. Another approach is a hybrid of the area difference method and the maximum gradient method. In this exemplification, the difference area method can be used when the search distance is larger than a predefined value. The difference area method may be better utilized for large search regions because it incorporates information from neighboring A-scans and neighboring B-scan frames to calculate a preferred lumen border location. Choice of mid-point where the search position is below a pre-defined threshold then uses a maximum gradient method which is likely to be sufficient for refining the lumen border since the mid-point has a very limited search region (being less than a pre-defined threshold) and is expected already to be relatively close to the actual lumen border location.

Figure 50:
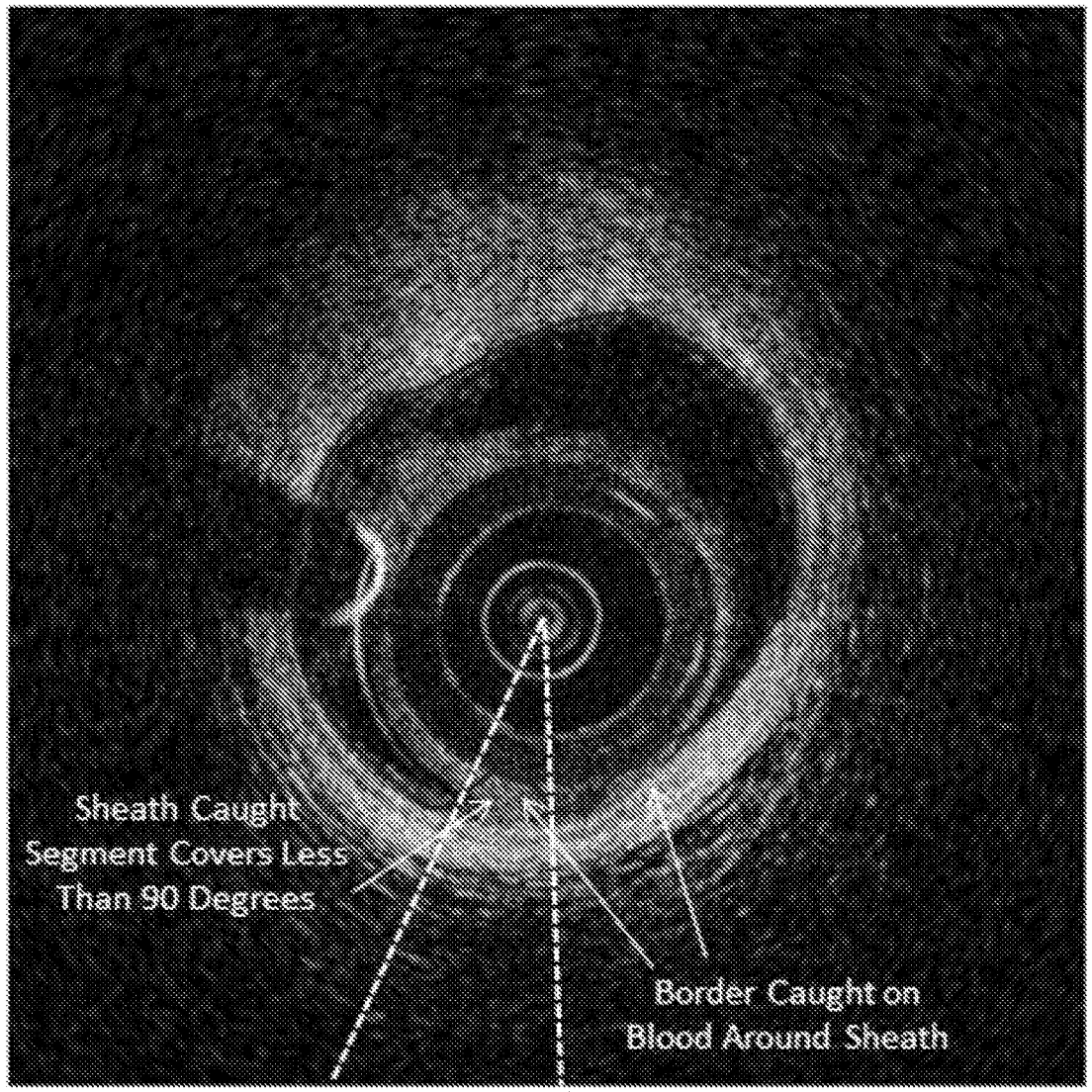
FIG. 50 shows a tomographic image of a final calculated lumen border with sheath artifacts and over-laid on a scan-converted tomographic image.

Referring to FIG. 18, block 604 is for identifying data artifacts arising from blood being caught on or near the imaging device to be evaluated and removed. In some instances, it may be desirable to smooth out data points that identify that the catheter is likely to be caught on false detections due to blood around the sheath. FIG. 50 shows a tomographic image of a final calculated lumen border with sheath artifacts and over-laid on a scan-converted tomographic image.

Figure 51:
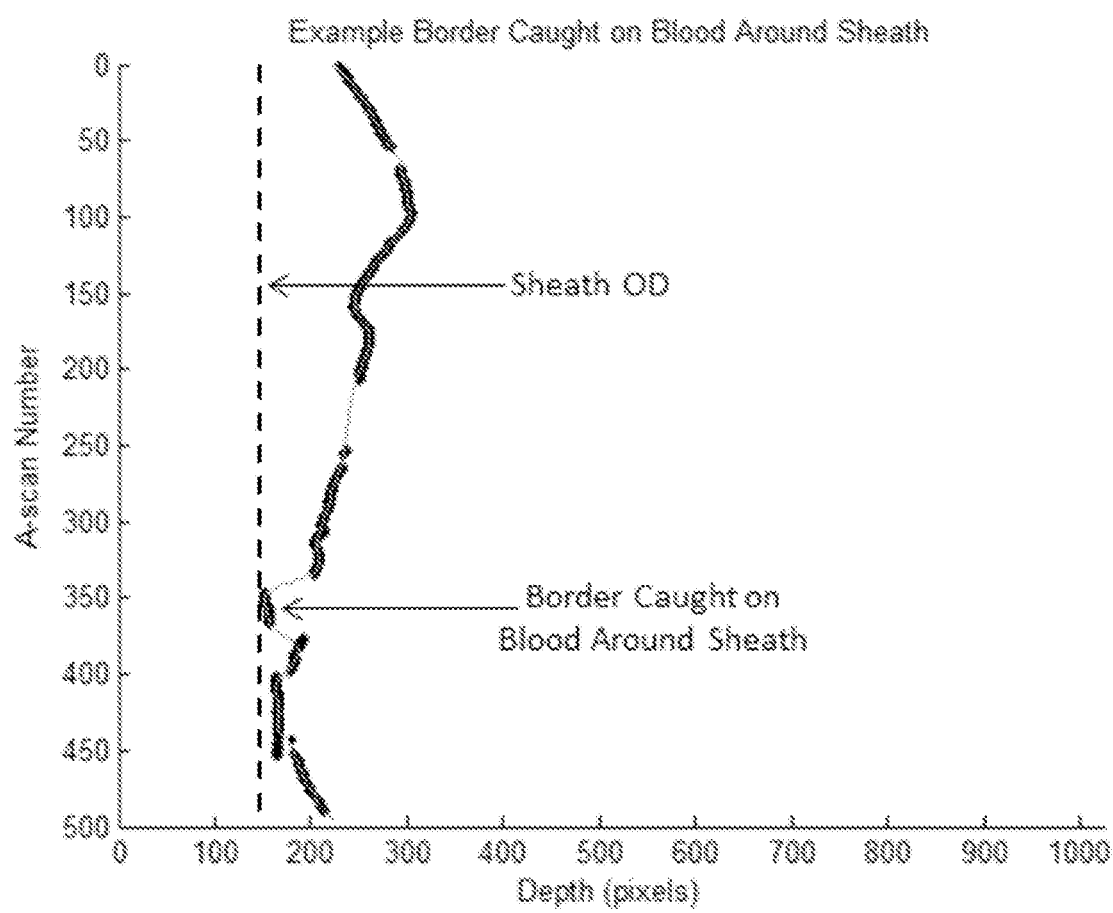
FIG. 51 shows a graph plotting edge points with blood artifacts for the lumen border calculated and shown in FIG. 50.

FIG. 51 shows a graph plotting edge points with blood artifacts for the lumen border calculated and shown in FIG. 50. The discontinuous edge data points identify data regions reflecting where the border is incorrectly caught on blood close to the sheath. This type of artifact found on the catheter sheath typically is found when the sheath is close to or touching the vessel wall.

To accomplish the smoothing of data points corresponding to the catheter sheath, a region close to the sheath can be chosen to identify all border points identified as being within some pre-defined distance of the sheath. The rotational angle covered by each sheath segment can then be computed. In certain examples, if the points cover less than a predetermined "Xmin" degrees (for example, 90°), those corresponding data points initially modeled as due to blood artifacts and temporarily removed from smoothing calculations. In other certain examples, if the points cover more than "Xmin" degrees but less than "Xmax" degrees (for example, 270°), the corresponding N number of points in the middle of the segments are kept for smoothing calculations as they initially are modeled to be a part of the catheter sheath, and all other points in the sheath segments are temporarily removed. If a segment covers more than "Xmin" degrees, some portion of the vessel likely is up against the sheath outer diameter and therefore a portion of the border is correct. If the sheath segment covers more than "Xmax" degrees, no points are removed and the border is left as is, and it is unlikely that points around the sheath need to be smoothed as blood artifacts are likely not present.

Figure 52:
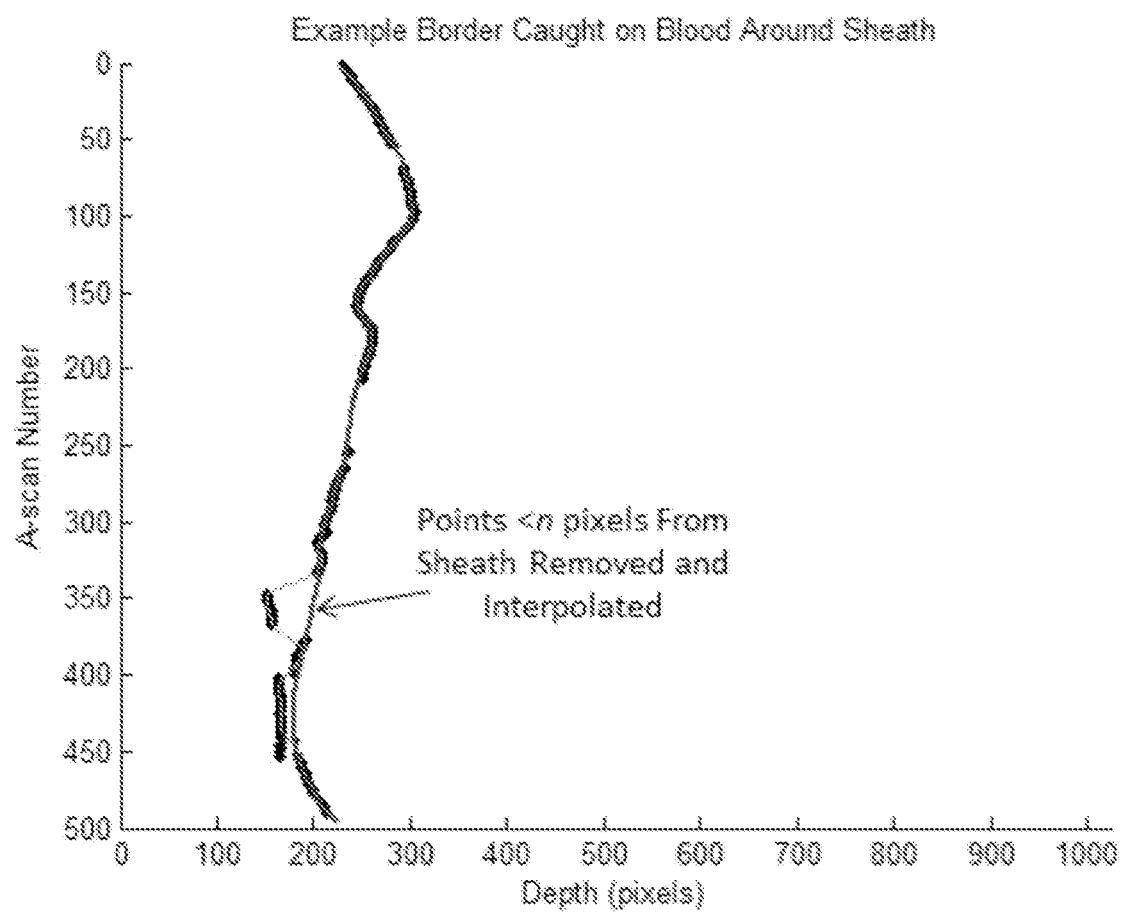
FIG. 52 shows a proper calculated contour having artifact data points removed from contour calculations.
Figure 53:
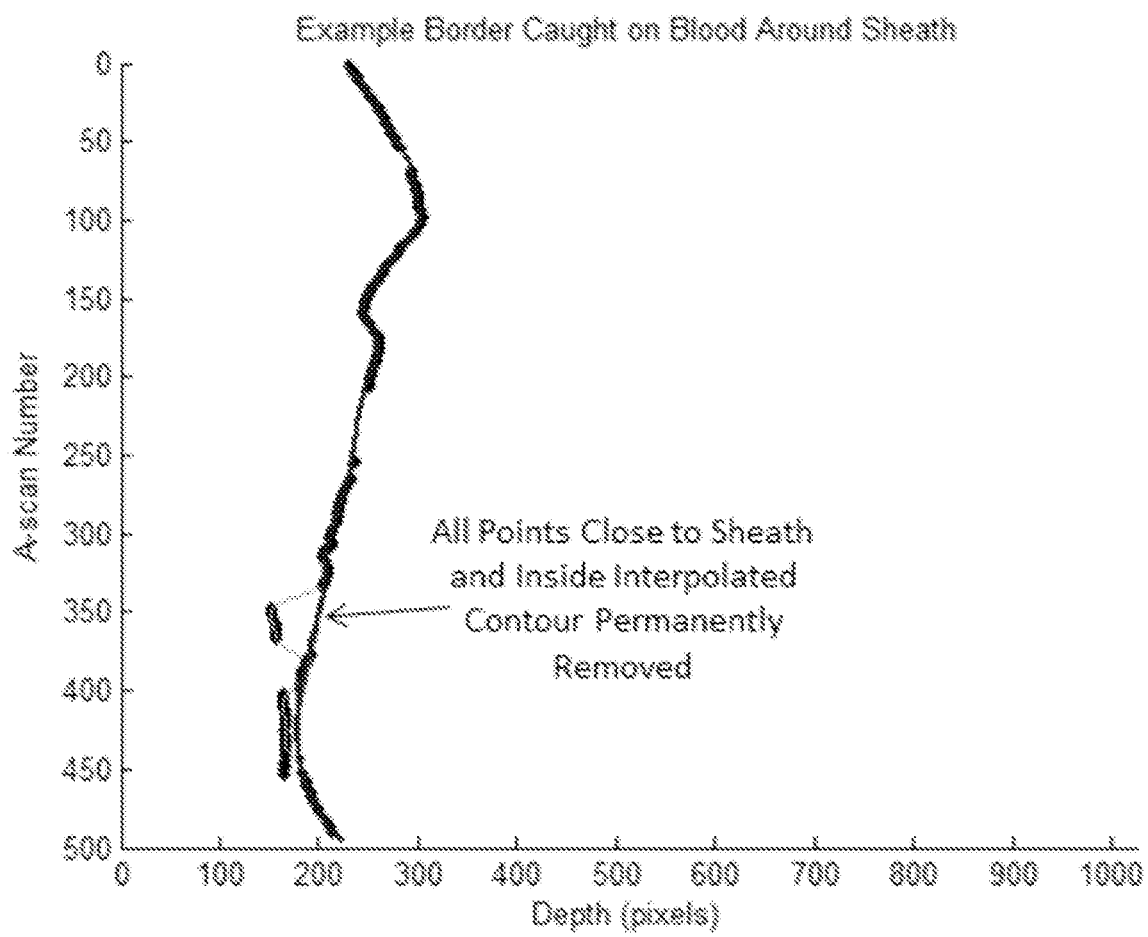
FIG. 53 shows a graph of points that are inside the sheath-interpolated contour (see FIG. 52) and have been removed by mechanisms described herein.
Figure 54:
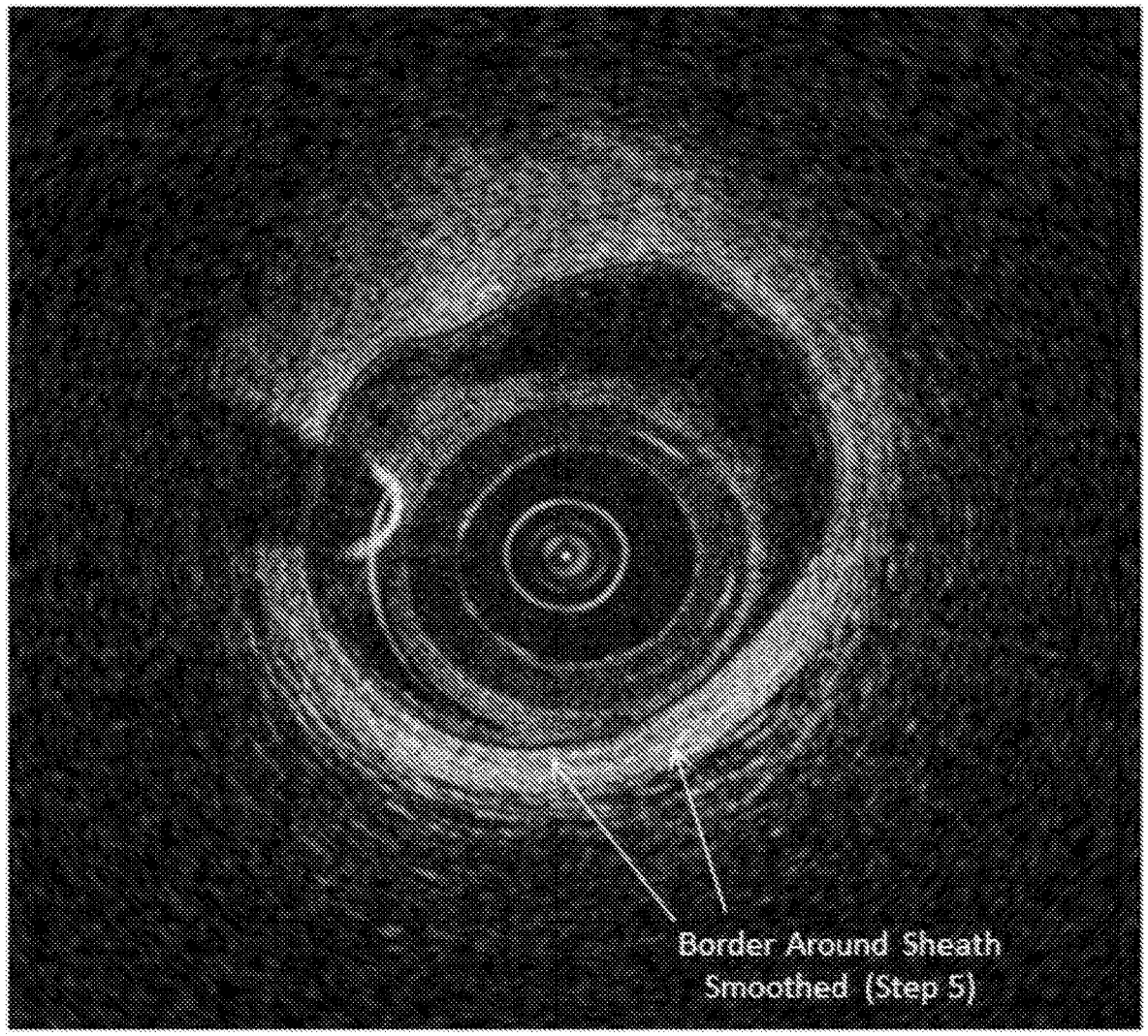
FIG. 54 shows the tomographic display image of the data from the plot in FIG. 53.

For the plot of signal depth versus A-scan number shown in FIG. 51, all segments close to the sheath covered less than Xmin degrees, and therefore were removed. With data points removed, the algorithm can be designed to interpolate across the missing data points, resulting in a proper contour as shown in the graph in FIG. 52. The original set of edge points can then be compared to this new contour; if it is determined they are inside (i.e. to the left) of the interpolated contour and within the predetermined cutoff amplitude of the catheter sheath, those data points are permanently removed. The resulting final calculated lumen border contour for this example is shown graphically in FIG. 53 and in a tomographic image in FIG. 54.

Figure 55:
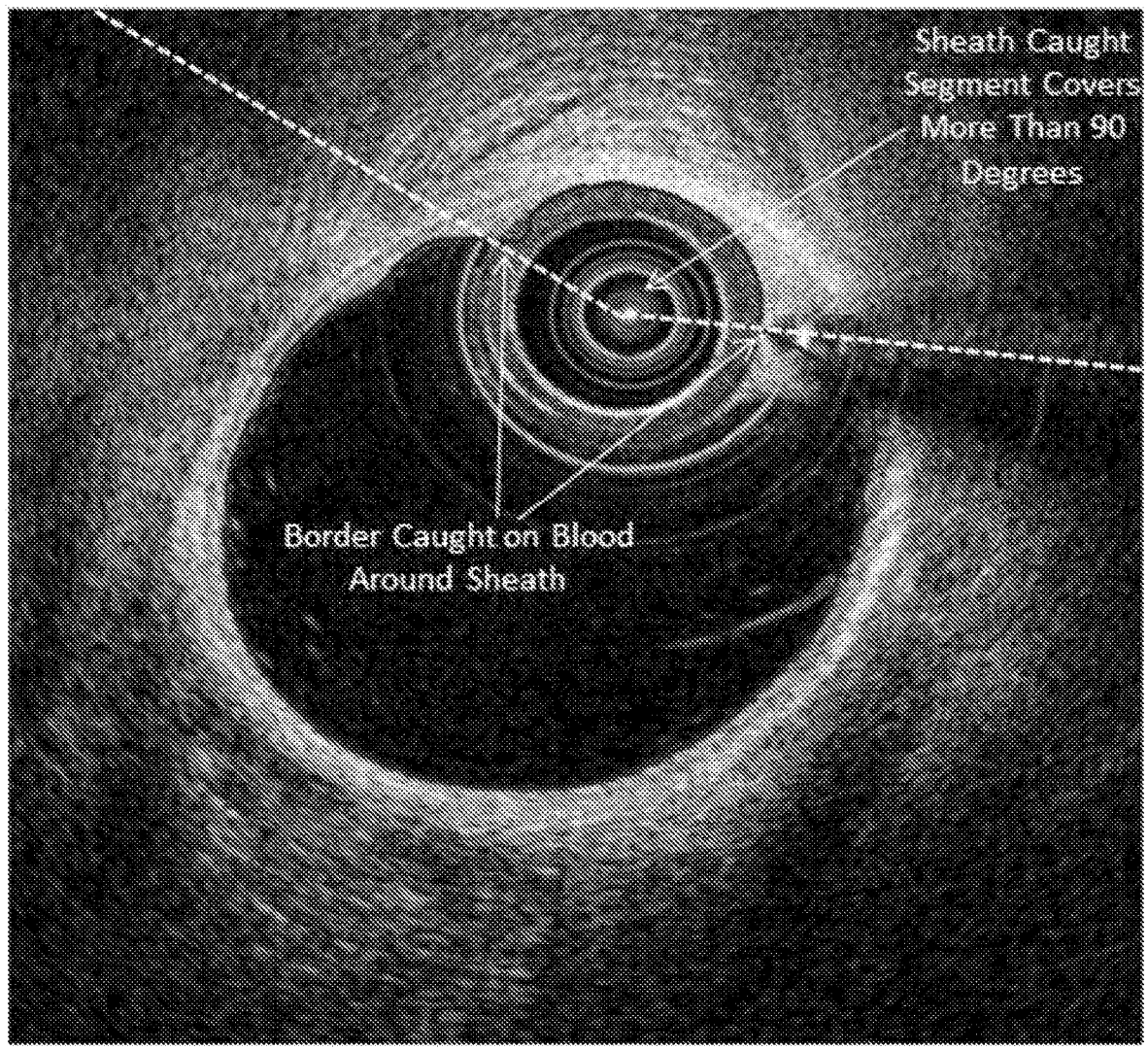
FIG. 55 shows a tomographic image of a catheter located against a lumen wall and contact with blood artifacts.
Figure 56:
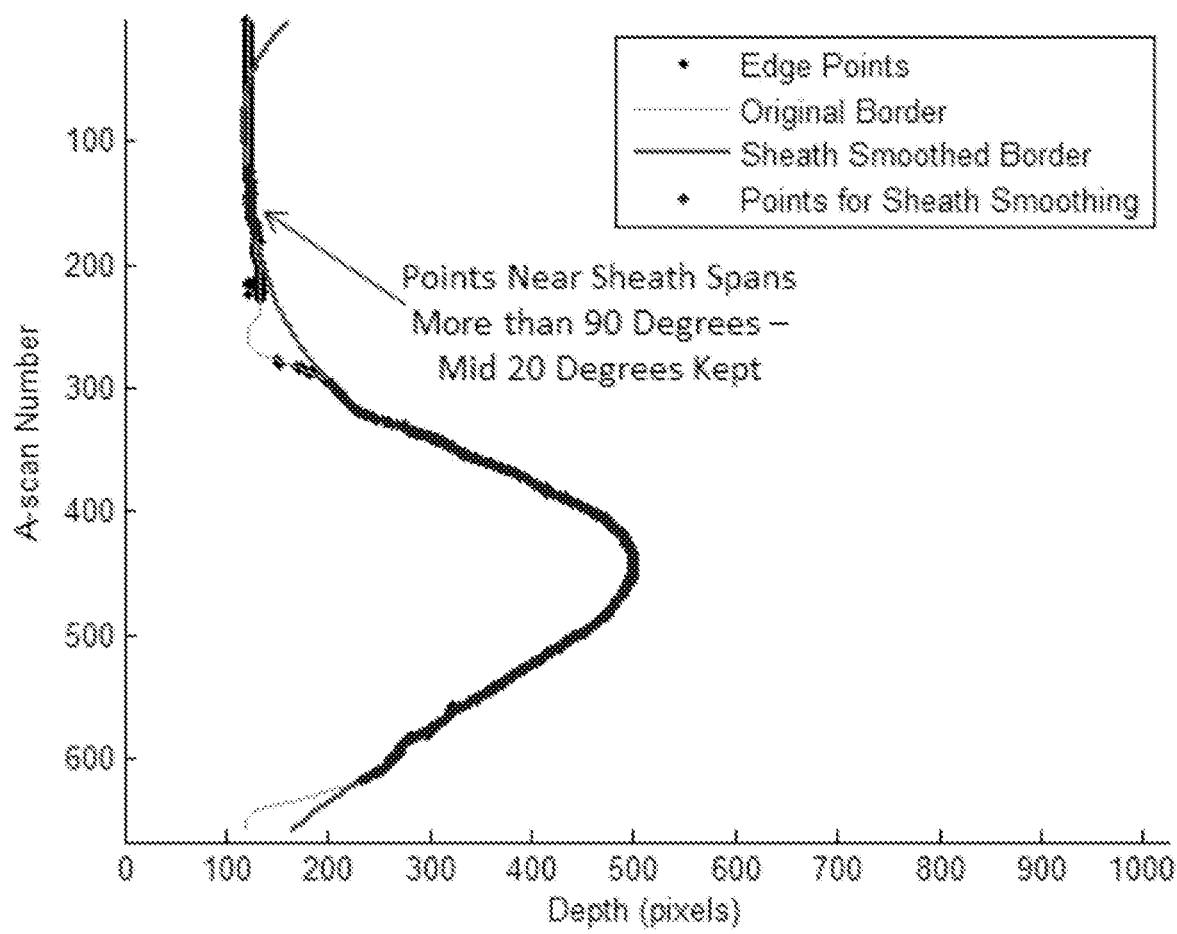
FIG. 56 shows a plot of A-scan data points for the tomographic image of FIG. 55 with sheath smoothed border and points used to generate a sheath-smoothed border.
Figure 57:
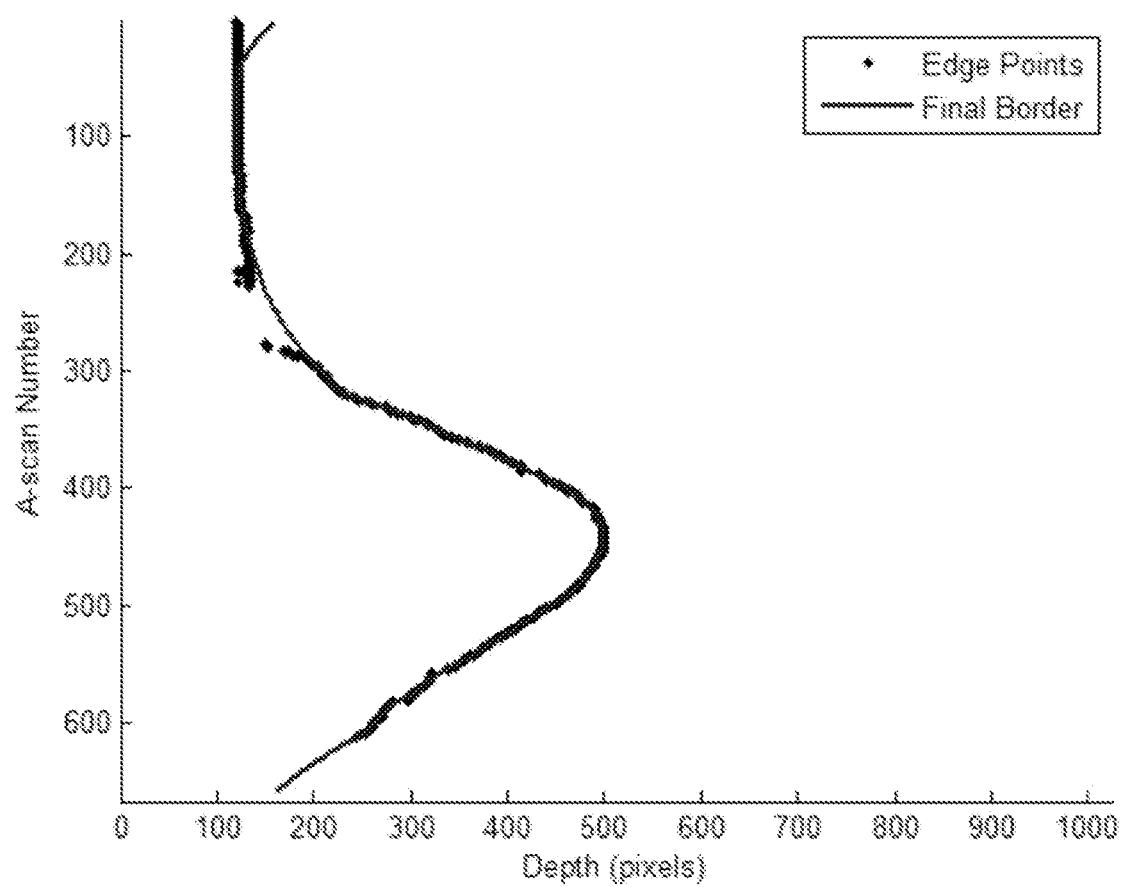
FIG. 57 shows a plot of final lumen border edge points after artifact points are removed and sheath smooth is complete.
Figure 58:
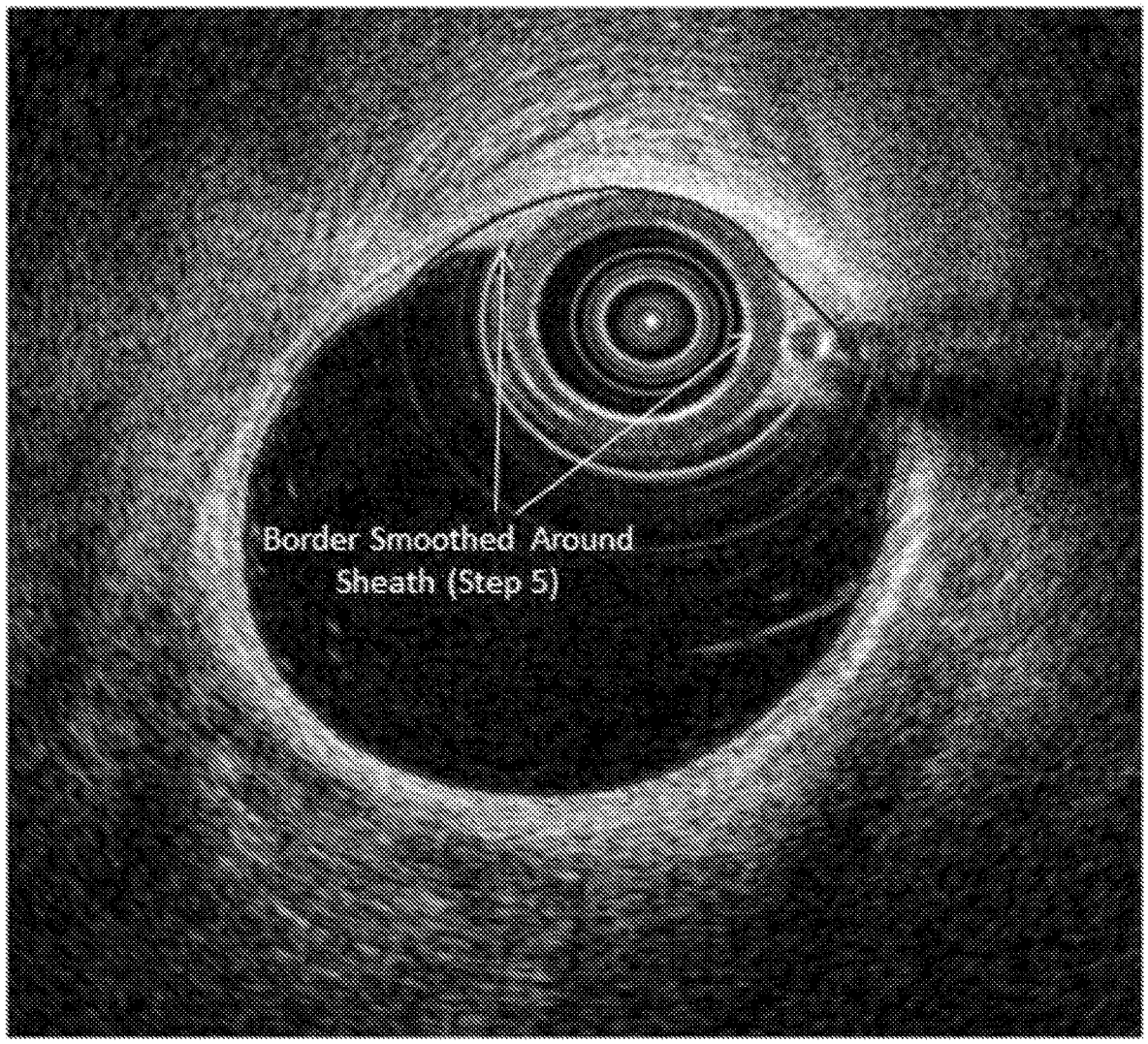
FIG. 58 shows a tomographic image of the final converted border for example shown in FIG. 55 after sheath soothing step had been applied.

Another example is provided in FIGS. 55-58. FIG. 55 shows a tomographic image of a catheter located against a lumen wall and with blood artifacts in contact; the sheath caught segment covers more than 90° but less than 270°. FIG. 56 shows a plot of A-scan data points for the B-scan of FIG. 55. FIG. 57 shows the plot of FIG. 56, having removed A-scan data points. Because the sheath segments cover more than "Xmin" degrees but less than "Xmax" degrees, the sheath segment mid-points are not kept when generating the intermediate interpolated contour. All points outside this contour are kept and the final border is properly smoothed across points where the sheath, vessel and blood meet. A final tomographic image of a sheath that has been smoothed is shown in FIG. 58.

The systems and methods of use described herein may be embodied in many different forms and should not be construed as limited to the embodiments set forth herein. Accordingly, the systems and methods of use described herein may take the form of an entirely hardware based embodiment, an entirely software based embodiment, or an embodiment combining software and hardware aspects. The systems and methods of use described herein can be performed using any type of computing device, such as a computer, that includes a processor or any combination of computing devices where each device performs at least part of the process or method.

Suitable computing devices typically include non-transitory memory coupled to a processor and an input-output device. Memory generally includes tangible storage media such as solid-state drives, flash drives, USB drives, RAM, ROM, EEPROM, flash memory, or other memory technology, CD-ROM, digital versatile disks (DVD) or other optical storage, magnetic cassettes, magnetic tape, or others. A processor generally includes a chip such as one made by INTEL or AMD, or a specially programmed chip such as an application specific integrated circuit or a field-programmable gate array. Exemplary input-output devices include a monitor, keyboard, mouse, touchpad, touchscreen, modem, Wi-Fi card, network interface card, Ethernet jack, USB port, disk drive, pointing device, joystick, etc. A system generally includes one or more of a computing device, a medical imaging instrument (e.g., for OCT or IVUS), others, or a combination thereof. A medical imaging instrument will generally include any or all of the components of a computing device as well as one or more structures such as those discussed herein for gathering images of a body.

The foregoing and other features and advantages of the invention are apparent from the following detailed description of exemplary embodiments, read in conjunction with the accompanying drawing. The systems and methods of use described herein may be embodied in many different forms and should not be construed as limited to the embodiments set forth herein. Accordingly, the systems and methods of use described herein may take the form of an entirely hardware embodiment, an entirely software embodiment, or an embodiment combining software and hardware aspects. The systems and methods of use described herein can be performed using any type of computing device, such as a computer, that includes a processor or any combination of computing devices where each device performs at least part of the process or method.

Methods of communication between devices or components of a system can include both wired and wireless (e.g., radiofrequency, optical or infrared, optics including fiber-optics and or lens systems) communications methods and such methods provide any other type of computer readable communications media. Such communications media typically embodies computer-readable instructions, data structures, program modules, or other data in a modulated data signal such as a carrier wave, data signal, or other transport mechanism and include any information delivery media.

As used herein, the word "or" means "and or or", sometimes seen or referred to as "and/or", unless indicated otherwise.

INCORPORATION BY REFERENCE

References and citations to other documents, such as patents, patent applications, patent publications, journals, books, papers, web contents, have been made throughout this disclosure. All such documents are hereby incorporated herein by reference in their entirety for all purposes.

EQUIVALENTS

Various modifications of the invention and many further embodiments thereof, in addition to those shown and described herein, will become apparent to those skilled in the art from the full contents of this document, including references to the scientific and patent literature cited herein. The subject matter herein contains important information, exemplification and guidance that can be adapted to the practice of this invention in its various embodiments and equivalents thereof.

What is claimed is:

1. A system comprising:
    an imaging catheter comprising an image capture device at a distal portion of the imaging catheter, wherein the imaging catheter is configured to capture, via the image capture device, imaging data associated with a vessel of a patient while the imaging catheter, including the image capture device, is positioned within the vessel, wherein the vessel comprises a vessel wall comprising a luminal border and a medial-adventitial border; and
    a processing system operably coupled to the imaging catheter, the processing system comprising a processor coupled to a memory and a display device in communication with the processor, wherein the processing system is configured to:
        receive, with the processor, the imaging data;
        generate, with the processor, a plurality of cross-sectional image frames of the vessel based on the imaging data, wherein each of the plurality of cross-sectional image frames is a two-dimensional image frame;
        for each of the plurality of cross-sectional image frames:
            automatically detect, with the processor, a location of a vessel wall border of the vessel wall, wherein the vessel wall border comprises at least one of the luminal border or the medial-adventitial border;
            determine an outline of the vessel wall border based on the detected location of the vessel wall border; and
            store the outline of the vessel wall border in the memory;
        receive, at the processor, a navigational input to navigate sequentially through the plurality of cross-sectional image frames;
        sequentially display, with the display device, the plurality of cross-sectional image frames in a manner representing motion through the vessel, while the navigational input is received; and
        in response to a cessation of the navigational input:
            stop the sequential display of the plurality of cross-sectional image frames at a target cross-sectional image frame, wherein the target cross-sectional image frame is a cross-sectional image frame, of the sequentially displayed plurality of cross-sectional image frames, that was being displayed at the time of the cessation of the navigational input;
            retrieve, from the memory, the outline of the vessel wall border for the target cross-sectional image frame; and
            display, with the display device, the target cross-sectional image frame and the outline of the vessel wall border overlaid on the vessel in the target cross-sectional image frame.

2. The system of claim 1,
    wherein the processing system further comprises a computer pointing device, and
    wherein, to receive the navigational input, the processing system is configured to:
        receive a user input from a user via the computer pointing device; and
        communicate the user input, as the navigational input, from the computer pointing device to the processor.

3. The system of claim 1, wherein, to detect the location of the vessel wall border, the processing system is configured to:
    perform, with the processor, a detection algorithm.

4. The system of claim 3, wherein, to detect the location of the vessel wall border, the processing system is further configured to:
    determine, with the processor, an occlusion of the vessel.

5. The system of claim 4, wherein to determine the occlusion, the processing system is configured to:
    compare the luminal border of the vessel to the medial-adventitial border of the vessel.

6. The system of claim 1, wherein, to detect the location of the vessel wall border, the processing system is configured to:

approximate the vessel wall border within a first cross-sectional image frame;

identify at least one control point on the vessel wall border;

extrapolate the at least one control point to approximate a second vessel wall border in a second cross-sectional image frame; and adjust the second vessel wall border in accordance with a frequency factor.

7. The system of claim 1, wherein the processing system is further configured to:

select, with the processor, a cross-sectional image frame from the plurality of cross-sectional image frames.

8. The system of claim 7, wherein the processing system is further configured to:

display, with the display device, the outline of the vessel wall border in the selected cross-sectional image frame.

9. The system of claim 1, wherein the processing system is operably coupled to a proximal portion of the imaging catheter.

10. The system of claim 1, wherein the image capture device comprises an optical coherence tomography (OCT) device or an intravascular ultrasound (IVUS) device.

* * * * *